(12) United States Patent
Tokuda et al.

(10) Patent No.: US 11,605,780 B2
(45) Date of Patent: Mar. 14, 2023

(54) COMPOUND, LIGHT-EMITTING ELEMENT CONTAINING THE SAME, DISPLAY DEVICE, AND LIGHTING DEVICE

(71) Applicant: Toray Industries, Inc., Tokyo (JP)

(72) Inventors: Takashi Tokuda, Otsu (JP); Daisaku Tanaka, Otsu (JP)

(73) Assignee: TORAY INDUSTRIES, INC., Tokyo (JP)

( * ) Notice: Subject to any disclaimer, the term of this patent is extended or adjusted under 35 U.S.C. 154(b) by 422 days.

(21) Appl. No.: 16/636,994

(22) PCT Filed: Aug. 17, 2018

(86) PCT No.: PCT/JP2018/030513
§ 371 (c)(1),
(2) Date: Feb. 6, 2020

(87) PCT Pub. No.: WO2019/044542
PCT Pub. Date: Mar. 7, 2019

(65) Prior Publication Data
US 2020/0185612 A1    Jun. 11, 2020

(30) Foreign Application Priority Data
Aug. 28, 2017 (JP) .............................. JP2017-162992

(51) Int. Cl.
| H01L 51/50 | (2006.01) |
| H01L 51/00 | (2006.01) |
| C07C 211/54 | (2006.01) |
| C09K 11/06 | (2006.01) |

(52) U.S. Cl.
CPC ........ H01L 51/0059 (2013.01); C07C 211/54 (2013.01); C09K 11/06 (2013.01); H01L 51/0077 (2013.01); *C09K 2211/1018* (2013.01); *H01L 51/5016* (2013.01); *H01L 51/5064* (2013.01); *H01L 51/5096* (2013.01)

(58) Field of Classification Search
None
See application file for complete search history.

(56) References Cited

U.S. PATENT DOCUMENTS

| 6,602,618 | B2 * | 8/2003 | Watanabe et al. ..... H05B 33/12 |
| | | | 428/690 |
| 10,424,739 | B2 | 9/2019 | Stoessel et al. |
| 10,497,877 | B2 | 12/2019 | Mujica-Fernaud et al. |
| 2011/0198581 | A1 | 8/2011 | Yabunouchi et al. |
| 2015/0236261 | A1 | 8/2015 | Stoessel et al. |
| 2016/0141510 | A1 | 5/2016 | Sasaki et al. |
| 2016/0149140 | A1* | 5/2016 | Kang ................ H01L 51/0061 |
| | | | 548/440 |
| 2016/0190469 | A1 | 6/2016 | Ogiwara et al. |
| 2017/0179398 | A1 | 6/2017 | Yokoyama et al. |
| 2018/0090688 | A1 | 5/2018 | Cha et al. |
| 2018/0175301 | A1 | 6/2018 | Ookuma et al. |
| 2018/0315941 | A1* | 11/2018 | Park ................ H01L 51/5072 |

FOREIGN PATENT DOCUMENTS

| CN | 104640958 A | 5/2015 | |
| CN | 105684180 A | 6/2016 | |
| JP | 2001196183 A | 7/2001 | |
| JP | 2008291011 A | 12/2008 | |
| JP | 2010222268 | * 10/2010 | ............ H01L 51/50 |
| JP | 2015502960 A | 1/2015 | |
| JP | 2016100376 A | 5/2016 | |
| KR | 20160091198 A | 8/2016 | |
| KR | 20170022438 A | 3/2017 | |
| WO | 2010044130 A1 | 4/2010 | |
| WO | 2014015938 A1 | 1/2014 | |
| WO | 2016006629 A1 | 1/2016 | |
| WO | 2016009823 A1 | 1/2016 | |
| WO | 2016199743 A1 | 12/2016 | |
| WO | 2017052261 | 3/2017 | |

OTHER PUBLICATIONS

International Search Report and Written Opinion for International Application No. PCT/JP2018/030513, dated Oct. 23, 2018, 6 pages.
Taiwan Office Action for Taiwan Application No. 107129533, dated Oct. 8, 2021, 5 pages.
Chinese Office Action for Chinese Application No. 201880054258. 6, dated Jul. 13, 2022, with translation, 24 pages.

\* cited by examiner

*Primary Examiner* — Gregory D Clark
(74) *Attorney, Agent, or Firm* — RatnerPrestia

(57) ABSTRACT

The present invention provides an organic thin film light-emitting element having improved light-emitting efficiency and durable service life. The compound of the present invention has the structure represented by general formula (1) below. In general formula (1), $Ar^1$ is an aromatic group having a specific structure, and $Ar^2$ is a separate aromatic group having a specific structure. n is an integer of 1 or 2, and p is an integer of 1 or 2. However, n+p=3. When n is 2, each $Ar^1$ may be the same or different, and when p is 2, each $Ar^2$ may be the same or different. However, $Ar^1$ and $Ar^2$ are not the same group.

[Chemical Formula 1]

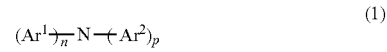

(1)

19 Claims, No Drawings

COMPOUND, LIGHT-EMITTING ELEMENT CONTAINING THE SAME, DISPLAY DEVICE, AND LIGHTING DEVICE

CROSS REFERENCE TO RELATED APPLICATIONS

This is the U.S. National Phase application of PCT/JP2018/030513, filed Aug. 17, 2018, which claims priority to Japanese Patent Application No. 2017-162992, filed Aug. 28, 2017, the disclosures of these applications being incorporated herein by reference in their entireties for all purposes.

FIELD OF THE INVENTION

The present invention relates to a compound, a light-emitting element containing the compound, a display device, and a lighting device.

BACKGROUND OF THE INVENTION

In recent years, organic thin-film light-emitting elements are actively studied. The organic thin-film light-emitting elements emit light when electrons injected from a negative electrode and holes injected from a positive electrode are recombined in an organic phosphor sandwiched between both the electrodes. Organic thin-film light-emitting elements have characteristics that they are thin, they can emit light with high luminance at low driving voltage, and they can emit multicolor light by selection of appropriate light-emitting materials such as fluorescent light-emitting materials and phosphorescent light-emitting materials.

In recent years, organic thin-film light-emitting elements have been steadily put into practical use, such as being used in main displays of mobile phones. However, existing organic thin-film light-emitting elements still have many technical problems. In particular, achieving both high-efficiency light emission and longer life of organic thin-film light-emitting elements is a major object.

Luminous efficiency of organic thin-film light-emitting elements is greatly influenced by carrier transport materials that transport carriers such as holes and electrons to a light-emitting layer. Among the carrier transport materials, as a material that transports holes (hole transport material), a material having a monoamine skeleton is known (see, for example, Patent Documents 1 to 5).

PATENT DOCUMENTS

Patent Document 1: Published Japanese Translation No. 2015-502960
Patent Document 2: International Publication No. 2016/006629
Patent Document 3: International Publication No. 2016/199743
Patent Document 4: International Publication No. 2014/015938
Patent Document 5: International Publication No. 2016/009823

SUMMARY OF THE INVENTION

It has been difficult, however, with the conventional techniques to improve the durable life of organic thin-film light-emitting elements while improving the luminous efficiency of the organic thin-film light-emitting elements. Moreover, even if the driving voltage can be lowered, it has been difficult to sufficiently achieve both the luminous efficiency and the durable life of the organic thin-film light-emitting elements. Thus, there has not yet been found a technique that achieves both high luminous efficiency and durable life.

An object of the present invention is to solve the above-mentioned problems of the conventional techniques, and to provide an organic thin-film light-emitting element that has improved luminous efficiency and improved durable life.

The compound according to the present invention is a compound represented by a general formula (1) shown below.

[Chemical Formula 1]

In the general formula (1), $Ar^1$ is a group represented by a general formula (2) shown below, $Ar^2$ is a group represented by a general formula (3) shown below, n is an integer of 1 or 2, p is an integer of 1 or 2, where n+p=3, and when n is 2, the groups $Ar^1$ may be identical or different, when p is 2, the groups $Ar^2$ may be identical or different, and $Ar^1$ and $Ar^2$ are not an identical group.

[Chemical Formula 2]

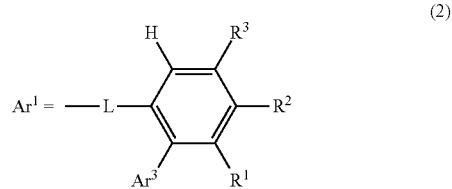

In the general formula (2), H represents a hydrogen atom, $Ar^3$ represents a substituted or unsubstituted aryl group or a substituted or unsubstituted heteroaryl group, L represents a linking group, and represents an unsubstituted arylene group or a heteroarylene group, $R^1$ to $R^3$ may be identical or different, and are each a hydrogen atom, a substituted or unsubstituted alkyl group, a substituted or unsubstituted alkoxy group, a substituted or unsubstituted phenyl group, a substituted or unsubstituted biphenyl group, or a substituted or unsubstituted terphenyl group, and substituents when the groups $R^1$ to $R^3$ are substituted are each an alkyl group or an alkoxy group.

[Chemical Formula 3]

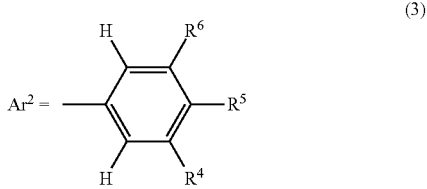

In the general formula (3), H represents a hydrogen atom, $R^4$ to $R^6$ may be identical or different, and are each a hydrogen atom, a substituted or unsubstituted phenyl group, a substituted or unsubstituted biphenyl group, a substituted or unsubstituted terphenyl group, or a substituted or unsubstituted quaterphenyl group, and substituents when the groups $R^4$ to $R^6$ are substituted are each an alkyl group or an alkoxy group.

According to the present invention, it is possible to provide an organic thin-film light-emitting element having high luminous efficiency and further having sufficient durable life.

DETAILED DESCRIPTION OF EMBODIMENTS OF THE INVENTION

In the following, suitable embodiments of the compound according to the present invention, a light-emitting element containing the compound, a display device, and a lighting device will be described in detail. However, the present invention is not limited to the following embodiments, and can be implemented with various modifications according to purpose and application. In this description, a light-emitting element is sometimes simply referred to as an element.

(Compound represented by general formula (1)) The compound according to the present invention is represented by a general formula (1).

[Chemical Formula 4]

(1)

In the general formula (1), $Ar^1$ is a group represented by a general formula (2) shown below, and $Ar^2$ is a group represented by a general formula (3) shown below. n is an integer of 1 or 2, p is an integer of 1 or 2, where n+p=3. When n is 2, the groups $Ar^1$ may be identical or different, and when p is 2, the groups $Ar^2$ may be identical or different. $Ar^1$ and $Ar^2$ are not an identical group.

[Chemical Formula 5]

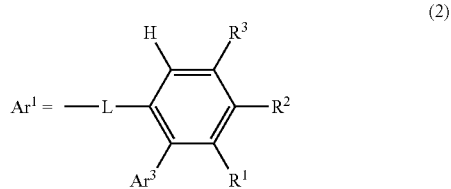

(2)

In the general formula (2), H represents a hydrogen atom. $Ar^3$ represents a substituted or unsubstituted aryl group or a substituted or unsubstituted heteroaryl group. L represents a linking group, and represents an unsubstituted arylene group or a heteroarylene group. $R^1$ to $R^3$ may be identical or different, and are each a hydrogen atom, a substituted or unsubstituted alkyl group, a substituted or unsubstituted alkoxy group, a substituted or unsubstituted phenyl group, a substituted or unsubstituted biphenyl group, or a substituted or unsubstituted terphenyl group. Substituents when the groups $R^1$ to $R^3$ are substituted are each an alkyl group or an alkoxy group.

[Chemical Formula 6]

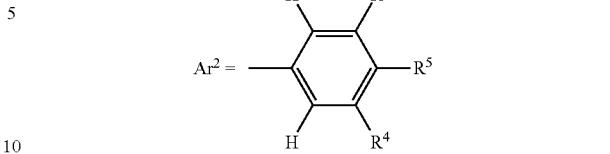

(3)

In the general formula (3), H represents a hydrogen atom. $R^4$ to $R^6$ may be identical or different, and are each a hydrogen atom, a substituted or unsubstituted phenyl group, a substituted or unsubstituted biphenyl group, a substituted or unsubstituted terphenyl group, or a substituted or unsubstituted quaterphenyl group. Substituents when the groups $R^4$ to $R^6$ are substituted are each an alkyl group or an alkoxy group.

An "aryl group" means an aromatic hydrocarbon group such as a phenyl group, a biphenyl group, a fluorenyl group, a phenanthryl group, a triphenylenyl group, and a terphenyl group. The aryl group may or may not have a substituent. The number of carbon atoms of the aryl group is not particularly limited, but is usually in the range of 6 or more and 40 or less.

An "arylene group" means a divalent group derived from an aryl group, and examples thereof include a phenylene group, a naphthylene group, a biphenylene group, a fluorenylene group, a phenanthrylene group, a terphenylene group, an anthracenylene group, and a pyrenylene group. The number of carbon atoms of the arylene group is not particularly limited, but is usually in the range of 6 or more and 40 or less. Further, when the arylene group has a substituent, the number of carbon atoms including that of the substituent is preferably in the range of 6 or more and 60 or less.

A "heteroarylene group" means a divalent or higher-valent group derived from an aromatic group having, in the ring, one or more atoms other than a carbon atom, and examples of the aromatic group include pyridine, quinoline, pyrimidine, pyrazine, triazine, quinoxaline, quinazoline, dibenzofuran, and dibenzothiophene. The heteroarylene group may or may not have a substituent. A preferable heteroarylene group is a divalent or trivalent heteroarylene group. The number of carbon atoms of the heteroarylene group is not particularly limited, but is usually in the range of 2 or more and 30 or less.

An "alkyl group" means a saturated aliphatic hydrocarbon group such as a methyl group, an ethyl group, an n-propyl group, an isopropyl group, an n-butyl group, a sec-butyl group, and a tert-butyl group, and may or may not have a substituent. The number of carbon atoms of the alkyl group is not particularly limited, but is usually in the range of 1 or more and 20 or less, more preferably in the range of 1 or more and 8 or less, from the viewpoint of availability and cost.

An "alkoxy group" means a substituent such as a methoxy group, an ethoxy group, an n-propoxy group, an isopropoxy group, an n-butoxy group, a sec-butoxy group, and a tert-butoxy group, and may or may not have a substituent. The number of carbon atoms of the alkoxy group is not particularly limited, but is usually in the range of 1 or more and 20 or less, more preferably in the range of 1 or more and 8 or less, from the viewpoint of availability and cost.

Conventional compounds having a monoamine skeleton do not necessarily have adequate performance as a light-emitting element material. For example, Patent Documents 1 to 5 disclose compounds A to E having a monoamine skeleton represented by formulae shown below.

[Chemical Formula 7]

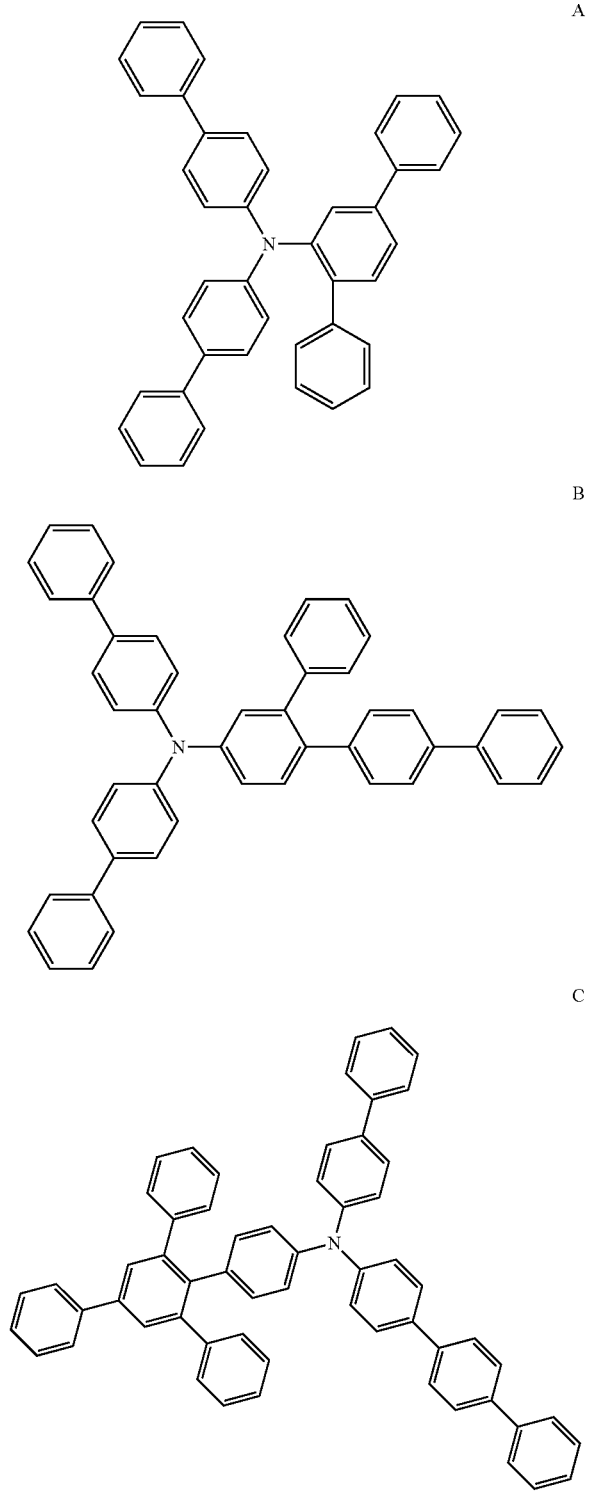

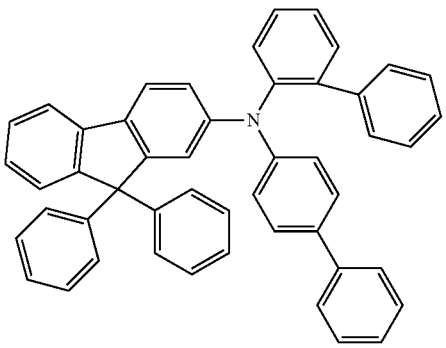

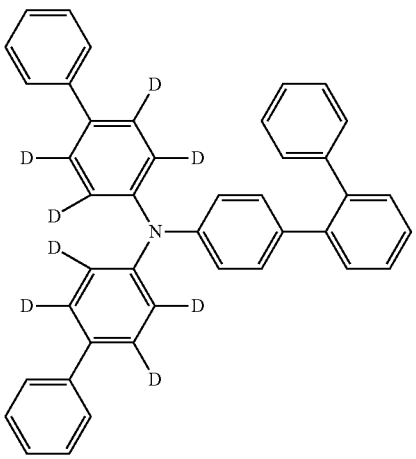

In elements containing these compounds in a hole injection layer or a hole transport layer, however, adequate performance has not yet been obtained, and creation of a compound capable of further improving the characteristics in terms of luminous efficiency and durable life is desired.

In the study of such improvement, the present inventors paid attention to an effect of a substituent linked to a nitrogen atom. In general, in a compound having a monoamine skeleton, substitution of a substituent on a nitrogen atom with an aryl group increases the fluorescence quantum yield. Under high fluorescence quantum yield, when a molecule comes into an excited state, the molecule emits light immediately in the excited state and is deactivated, so that the molecule is hardly decomposed in the excited state.

In the compound represented by the general formula (1), introducing, into an ortho position of the aryl group directly linked to the nitrogen atom, another aryl group reduces the planarity of the molecule to reduce the molecular interaction. The reduced molecular interaction leads to a larger energy gap and a shallower LUMO level. That is, since the electron-blocking properties are improved, the luminous efficiency and the durable life can be improved. Furthermore, since the molecular interaction is reduced, the fluorescence quantum yield in an amorphous state is increased. Therefore, in an organic thin-film light-emitting element, decomposition of the compound represented by the general formula (1) in an excited state can be suppressed, and the element has a long durable life.

Meanwhile, in structures such as the compounds A and D, for example, an aryl group in which an ortho position is substituted with a phenyl group is directly bonded to the nitrogen atom. In such a structure, the molecular interaction is reduced too much, the hole mobility is low, and the driving voltage is high. Therefore, the structure as represented by the general formula (2), in which $Ar^1$ has the linking group L, can maintain the hole mobility and lower the driving voltage.

In the general formula (2), one of ortho positions of the aryl group bonded to L always has a substituent represented by Ara. In a compound having a substituent at both ortho positions of an aryl group bonded to L, such as the compound C, the molecular twist is too large, the carbon-carbon bond energy at the ortho positions is small, and the compound is easily decomposed.

In the general formula (3), it is preferable that the hydrogen atom of $Ar^2$ be not a deuterium atom. When $Ar^2$ has a deuterium atom as in, for example, the compound E, the twist of the deuterium atom with an adjacent substituent is larger than in the case of a hydrogen atom. Therefore, in the compound represented by the general formula (1), appropriate expansion of the conjugate cannot be maintained, the HOMO orbital distribution is narrowed, and the hole mobility is lowered. In addition, also when an ortho position of $Ar^2$ is substituted with an aryl group or the like, the twist of the compound is excessively large, so that the hole mobility is lowered.

Herein, the phrase "not a deuterium atom" does not exclude the inevitable presence of a naturally occurring deuterium atom. In other words, since deuterium atoms occur naturally, deuterium atoms are contained even in compounds in which no substituent is intentionally substituted with a deuterium atom. However, the abundance of deuterium atoms is sufficiently small compared to that of hydrogen atoms, and thus the hole mobility is not affected unless in a compound in which a substituent is intentionally substituted with a deuterium atom.

In the general formula (1), it is preferable that at least one of $Ar^2$ be a substituted or unsubstituted phenyl group, a substituted or unsubstituted biphenyl group, a substituted or unsubstituted terphenyl group, or a substituted or unsubstituted quaterphenyl group excluding a group represented by a formula (4) shown below.

a substituted or unsubstituted p-biphenyl group or a substituted or unsubstituted p-terphenyl group.

Moreover, from the viewpoint of obtaining a thermally stable compound having a rigid structure, it is particularly preferable that at least one of $Ar^2$ be a substituted or unsubstituted p-terphenyl group.

From the viewpoint of not expanding the conjugate too much, L in the general formula (2) is an unsubstituted arylene group or an unsubstituted heteroarylene group, preferably an unsubstituted phenylene group or an unsubstituted biphenylene group, more preferably a 1,4-phenylene group.

In the general formula (2), $Ar^3$ is not an alkyl group such as a methyl group or an ethyl group, but is preferably a substituted or unsubstituted aryl group or a substituted or unsubstituted heteroaryl group so that $Ar^3$ may impart a moderate twist to the inside of the molecule. $Ar^3$ is more preferably a substituted or unsubstituted aryl group because a heteroaryl group usually lowers the LUMO level of a molecule and impairs the electron-blocking properties. Furthermore, from the viewpoint of maintaining appropriate expansion of the conjugate and maintaining high fluorescence quantum yield, $Ar^3$ is preferably a substituted or unsubstituted phenyl group, a substituted or unsubstituted biphenyl group, a substituted or unsubstituted terphenyl group, a substituted or unsubstituted fluorenyl group, or a substituted or unsubstituted naphthyl group, and is particularly preferably a substituted or unsubstituted phenyl group, a substituted or unsubstituted biphenyl group, or a substituted or unsubstituted terphenyl group.

In the general formula (1), n is an integer of 1 or 2, and p is an integer of 1 or 2 in order to maintain a high glass transition temperature while reducing the molecular interaction to increase the band gap.

The structure represented by the general formula (2) is not particularly limited, and specific examples include the following. The following are examples, and any compound other than those specified in the following is also preferably used as long as the compound is represented by the general formula (2).

[Chemical Formula 8]

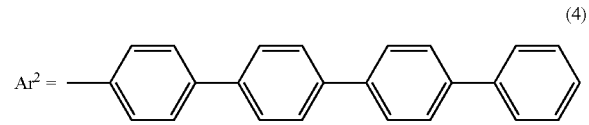

(4)

This is because limiting the number of carbon atoms in the substituent directly linked to the nitrogen atom can prevent the reduction of the energy gap from the LUMO level. Although a compound in which $Ar^2$ is a p-quaterphenyl group, that is, a group represented by the formula (4) has an effect of improving the luminous efficiency and the durable life compared to the compounds A to E, the compound is not so preferable because the conjugate expands too much, and the energy gap from the LUMO level is too small.

In the general formula (1), it is more preferable that at least one of $Ar^2$ be a substituted or unsubstituted biphenyl group or a substituted or unsubstituted terphenyl group.

In addition, from the viewpoint of maintaining a moderately wide energy gap, a shallow LUMO level, and a moderately high triplet level that are required for achieving higher luminous efficiency more easily, and of also maintaining high fluorescence quantum yield indispensable for longer life, it is more preferable that at least one of $Ar^2$ be

[Chemical Formula 9]

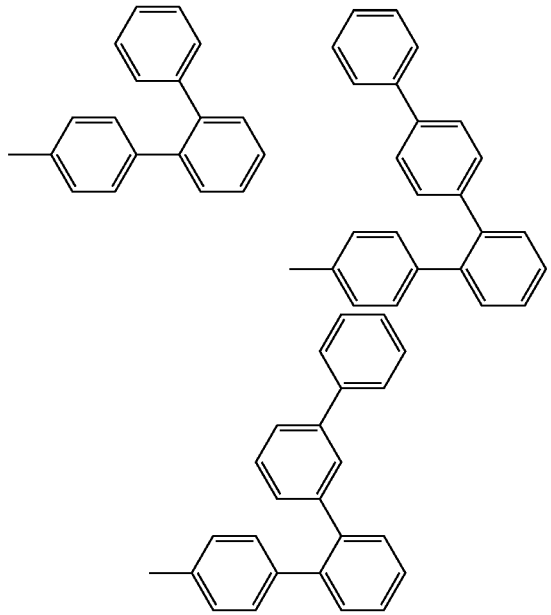

-continued
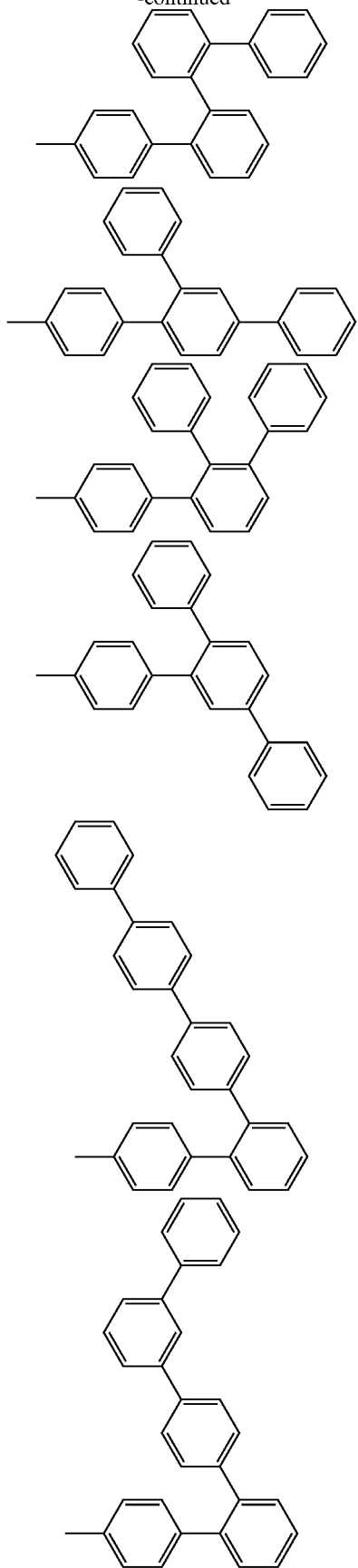
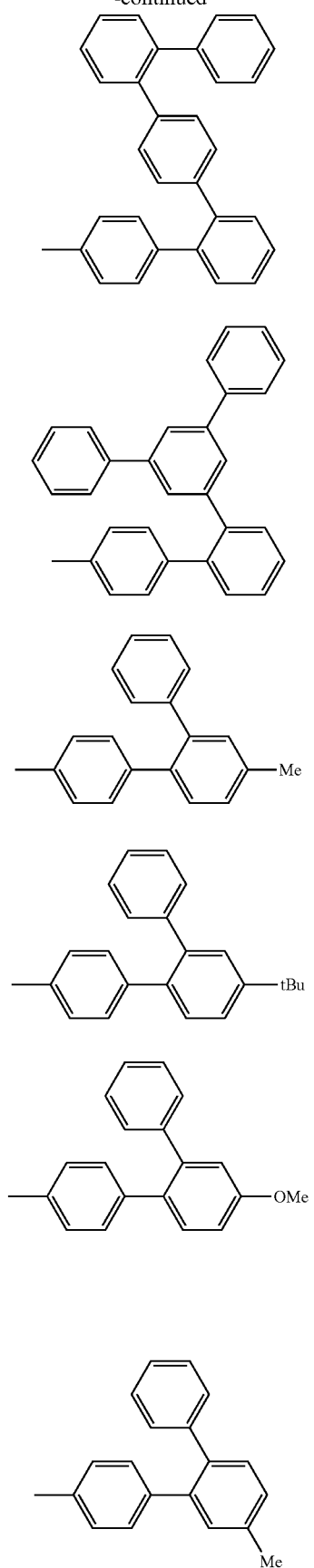

[Chemical Formula 10]
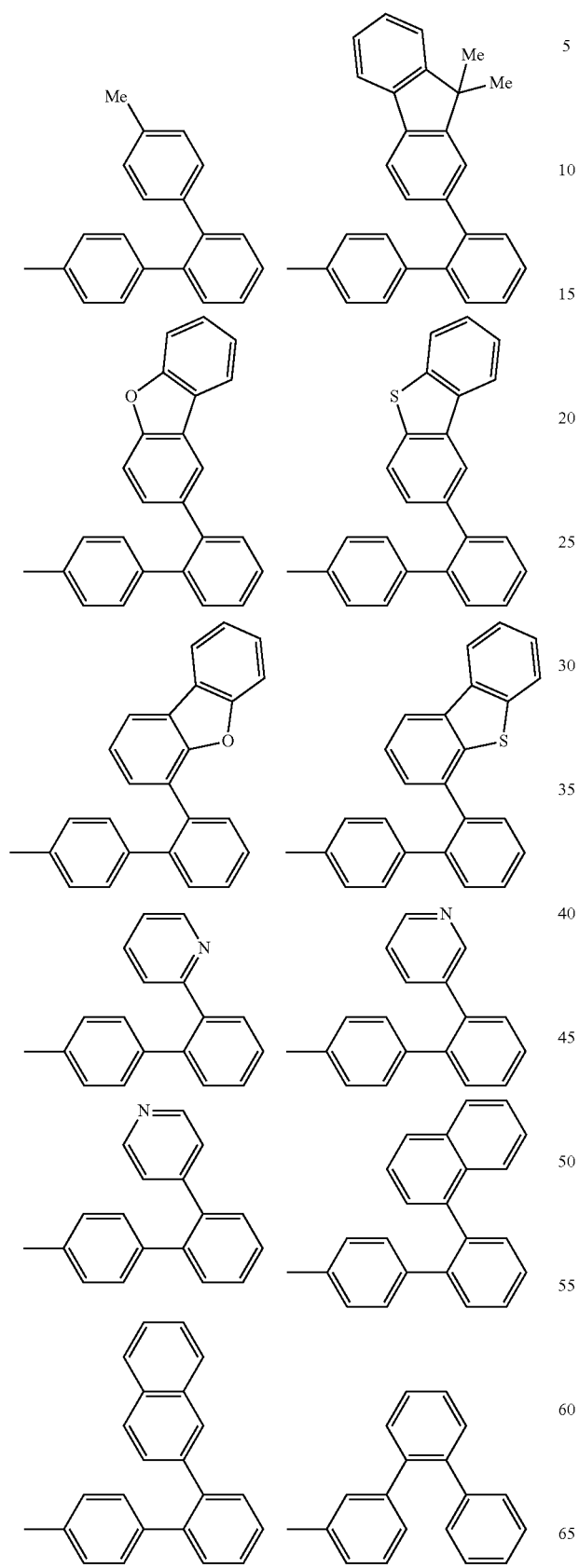
[Chemical Formula 11]
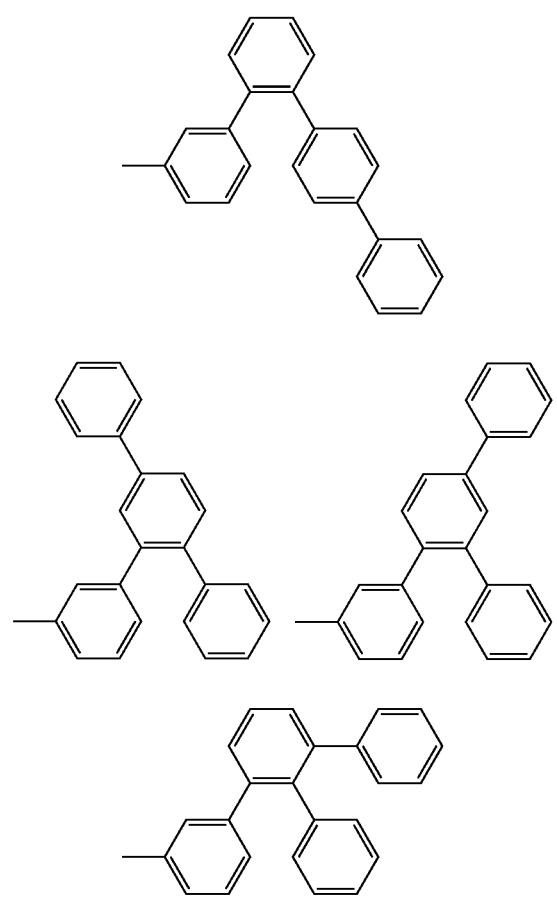

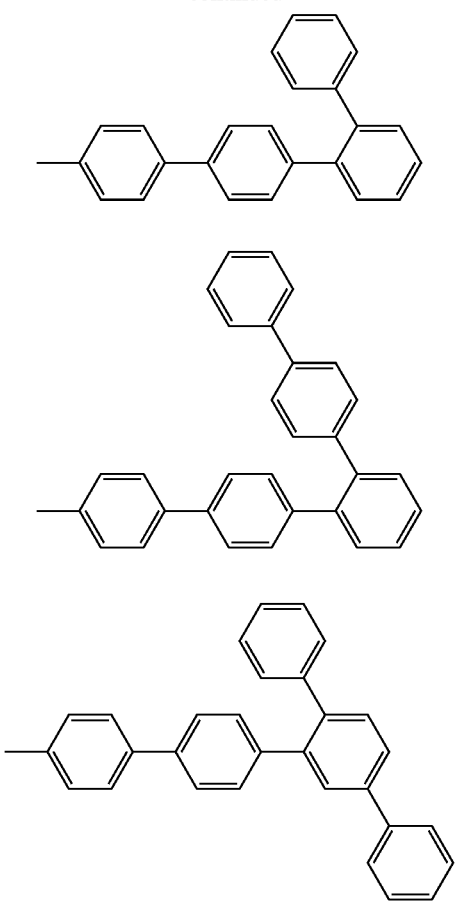
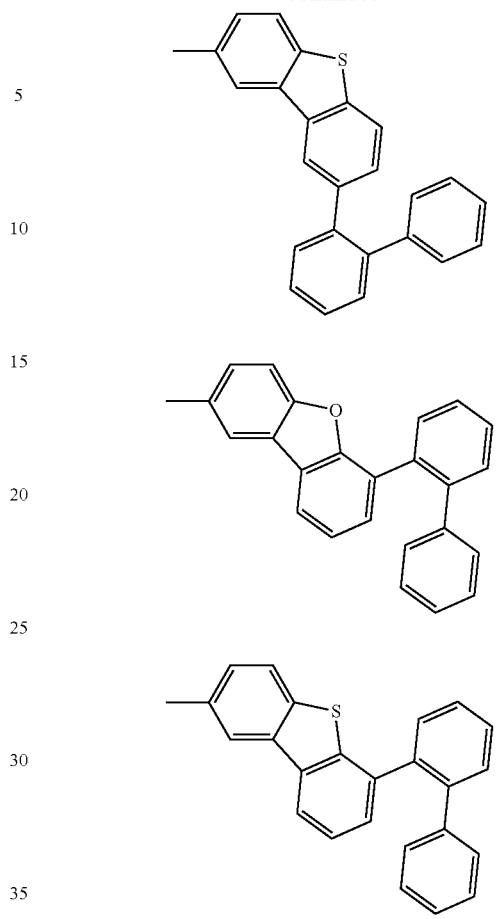
The structure represented by the general formula (3) is not particularly limited, and specific examples include the following. The following are examples, and any compound other than those specified in the following is also preferably used as long as the compound is represented by the general formula (3).
[Chemical Formula 12]
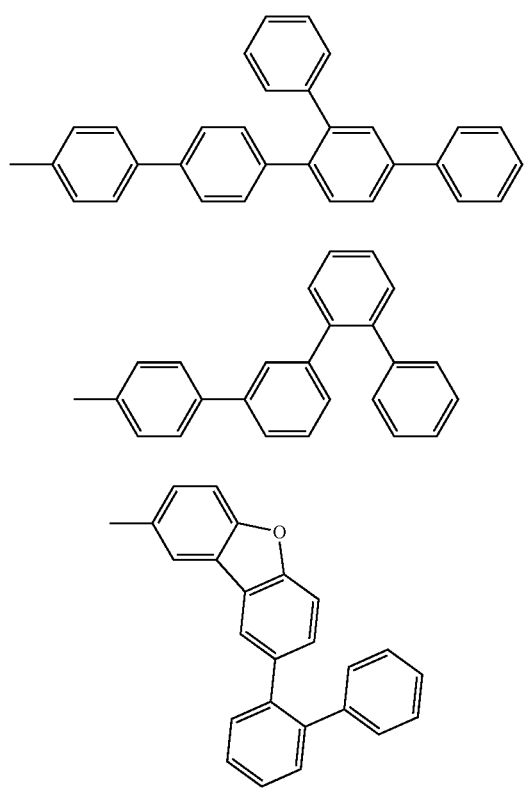
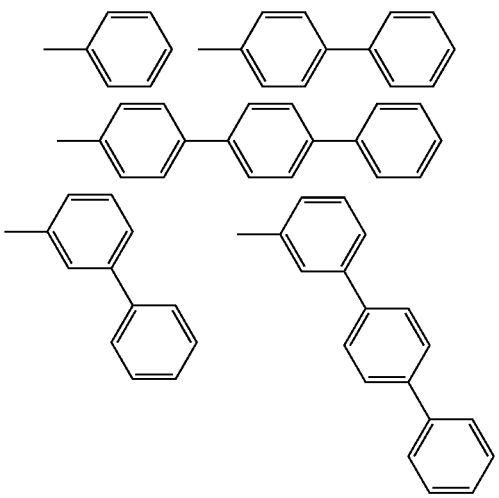

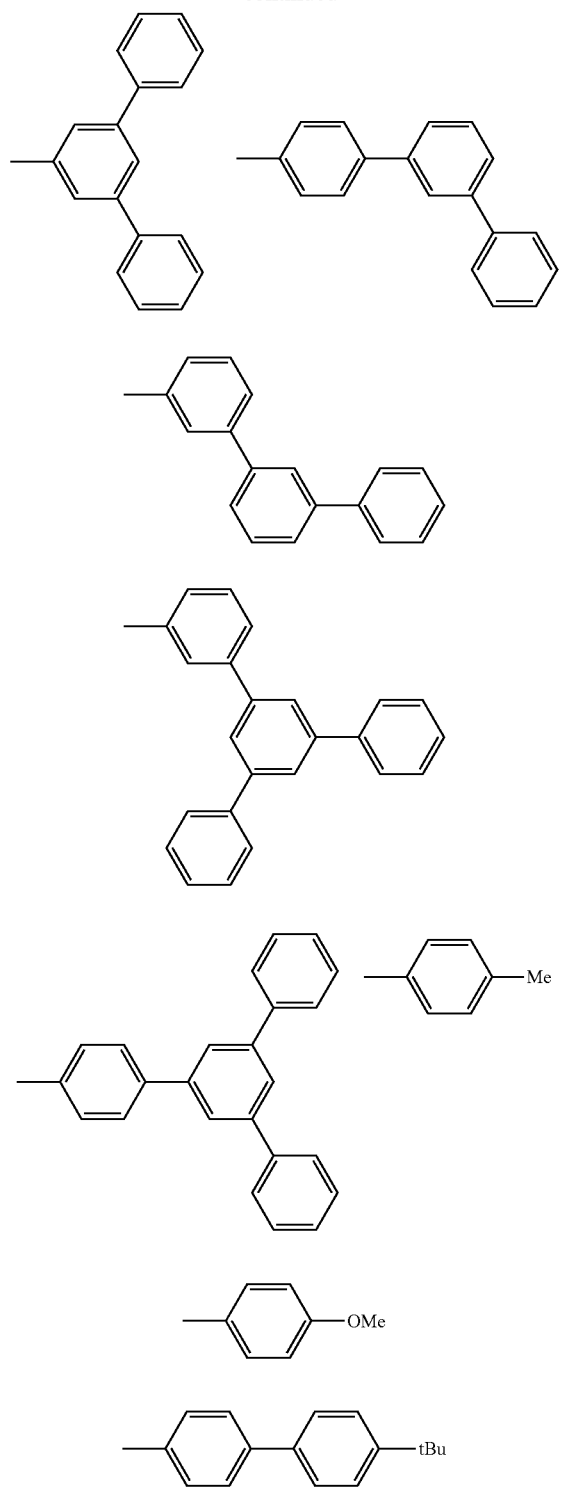
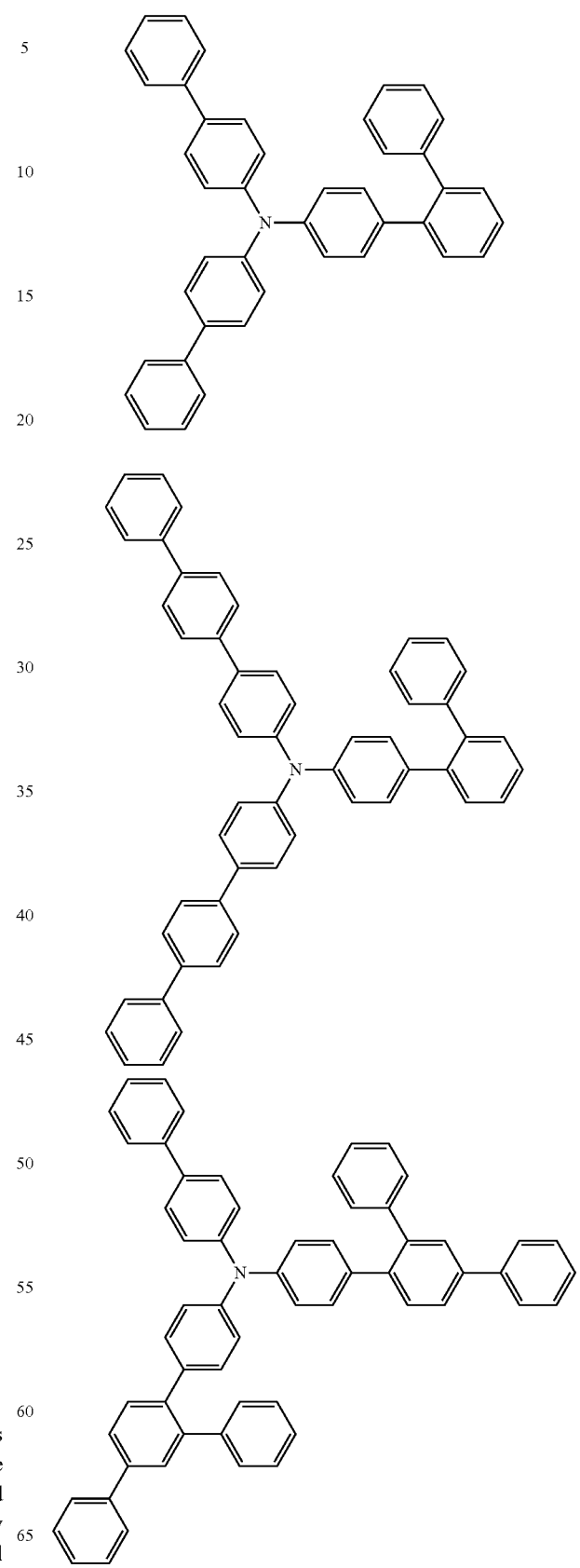
[Chemical Formula 13]
The compound represented by the general formula (1) is not particularly limited, and specific examples include the following. The following are examples, and any compound other than those specified in the following is also preferably used as long as the compound is represented by the general formula (1).

-continued
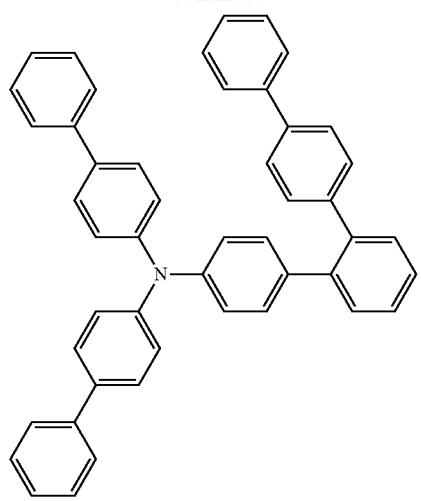
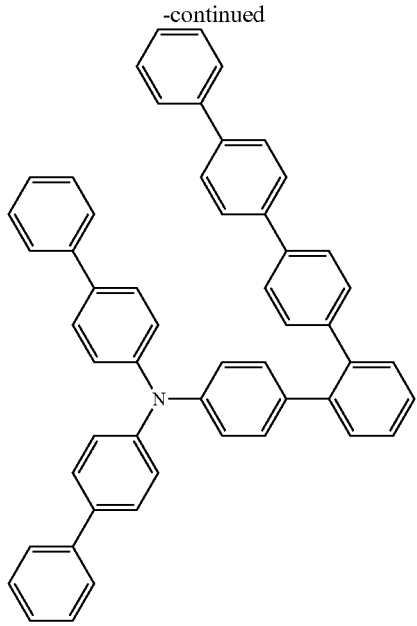
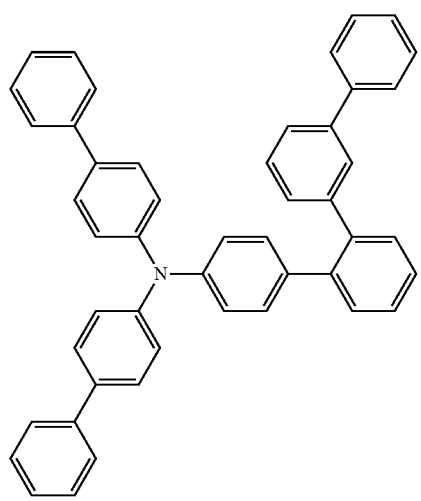
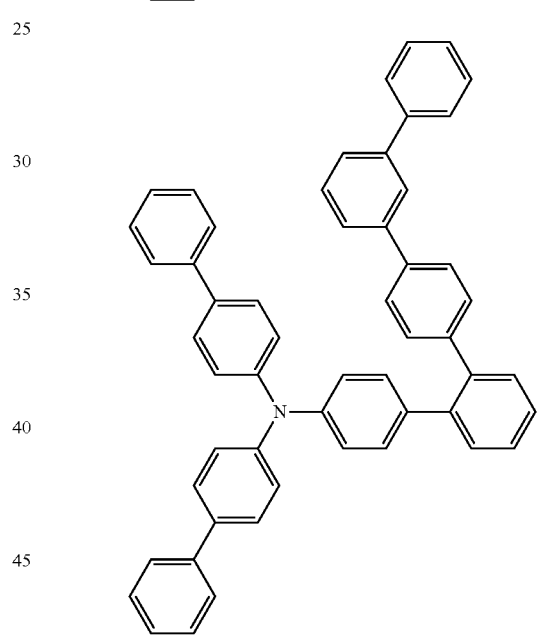
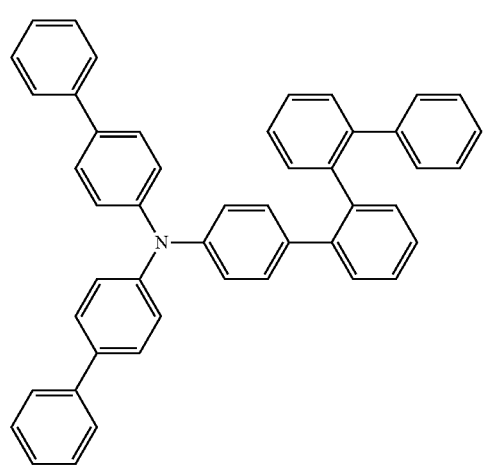
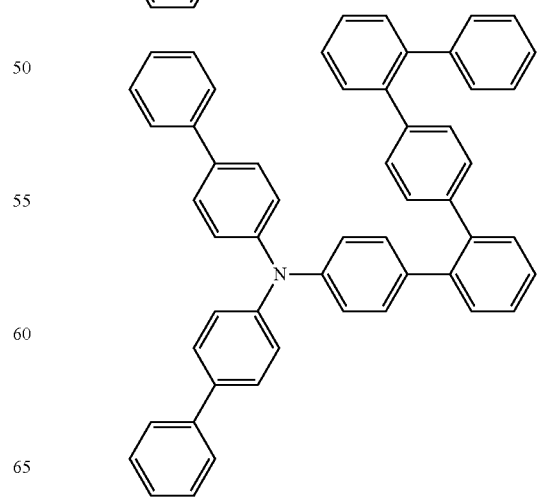

[Chemical Formula 14]
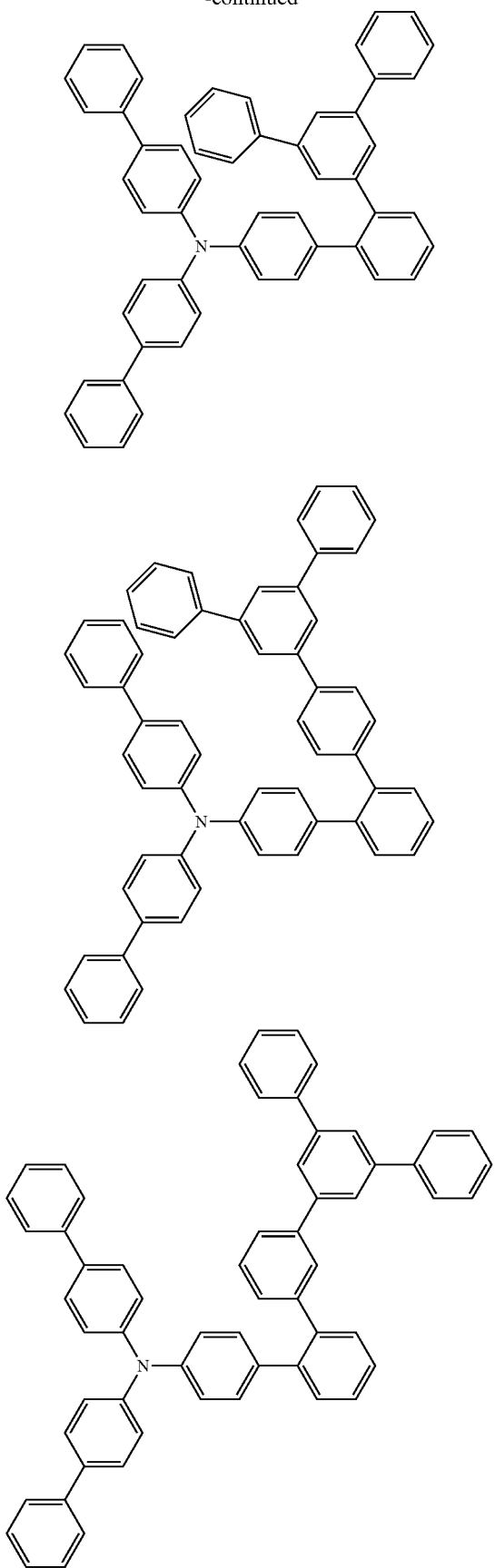
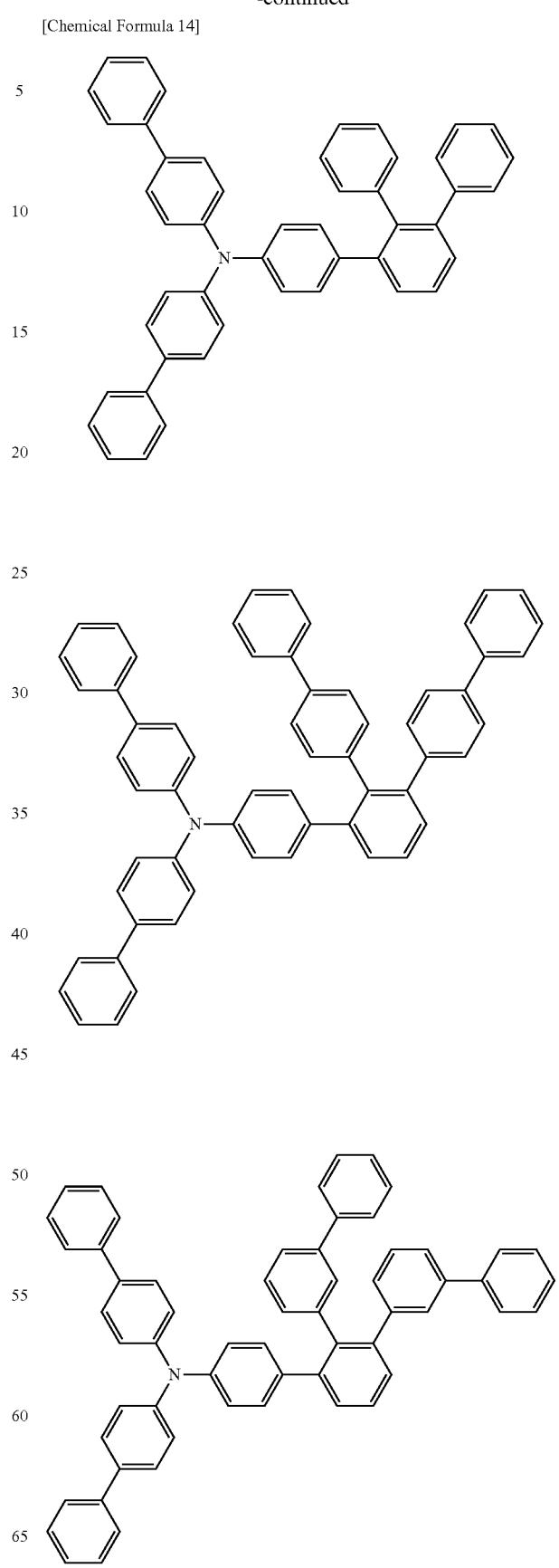

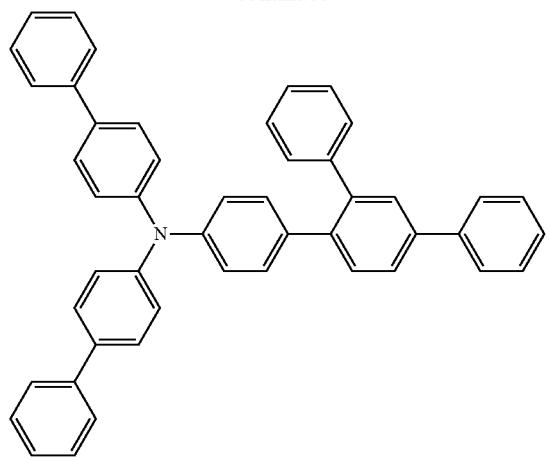
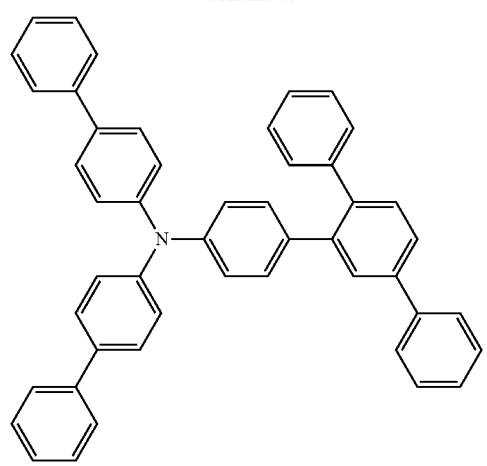
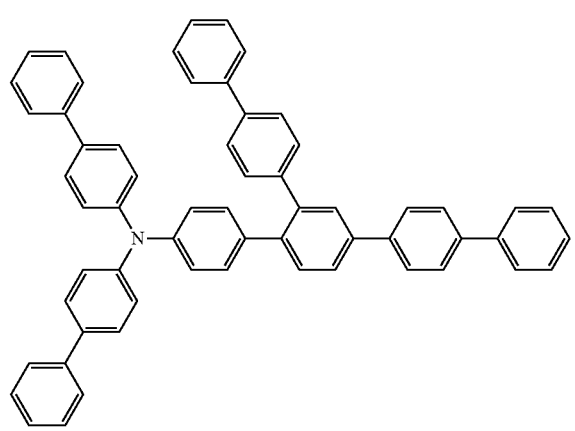
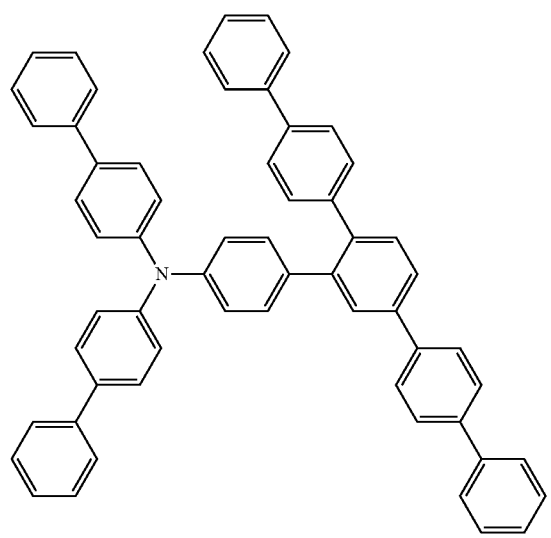
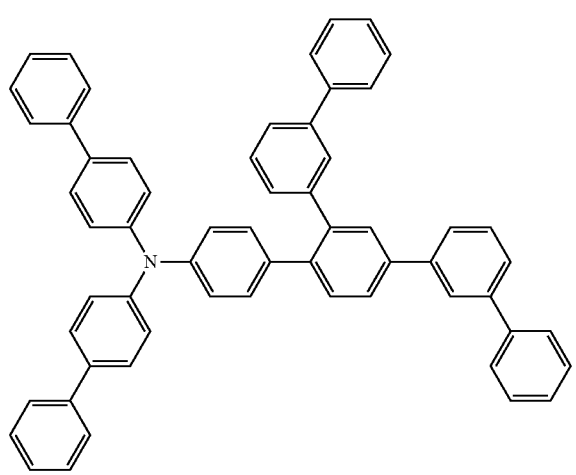
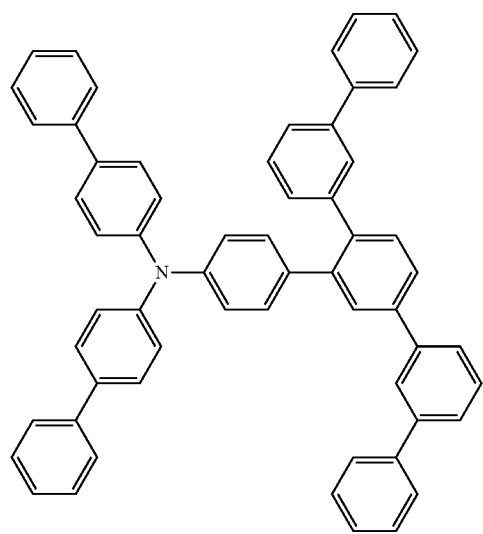

[Chemical Formula 15]
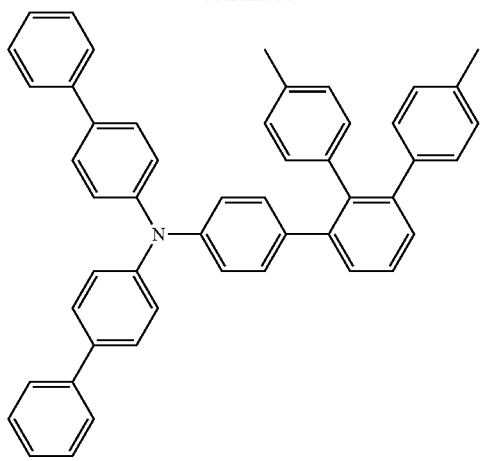
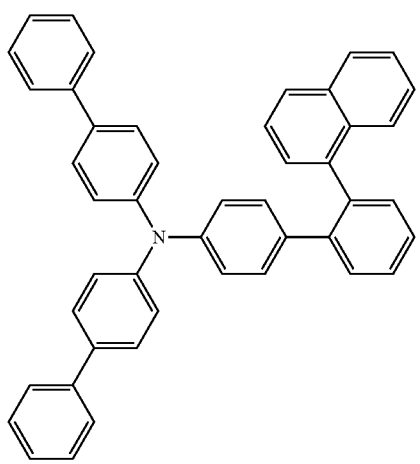
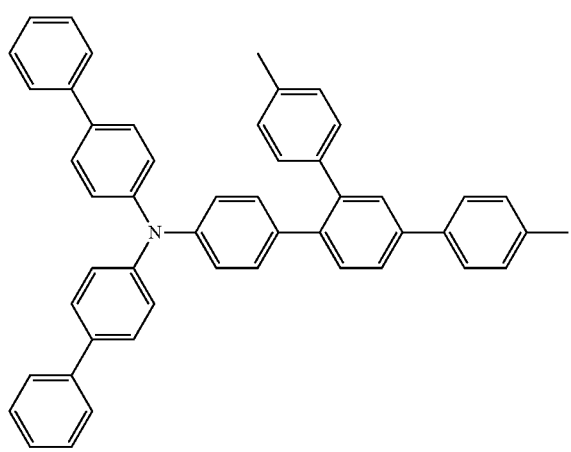
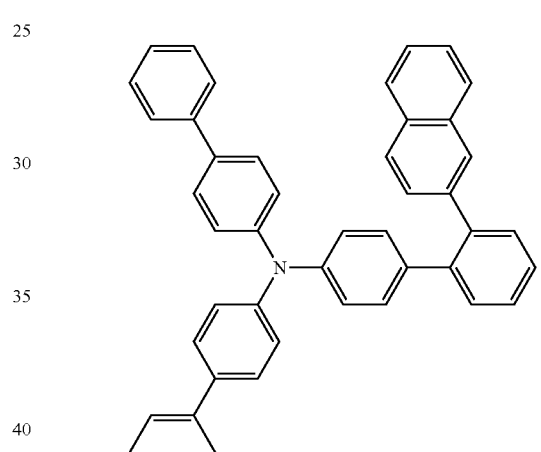
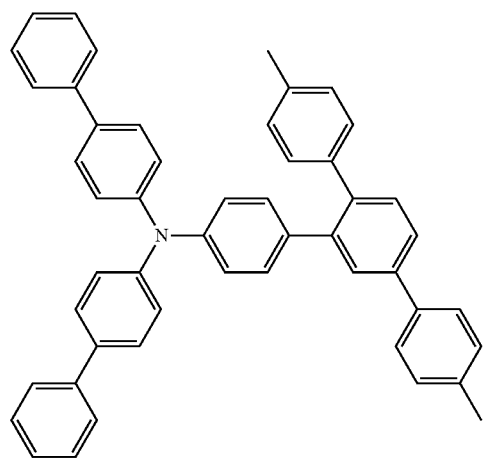
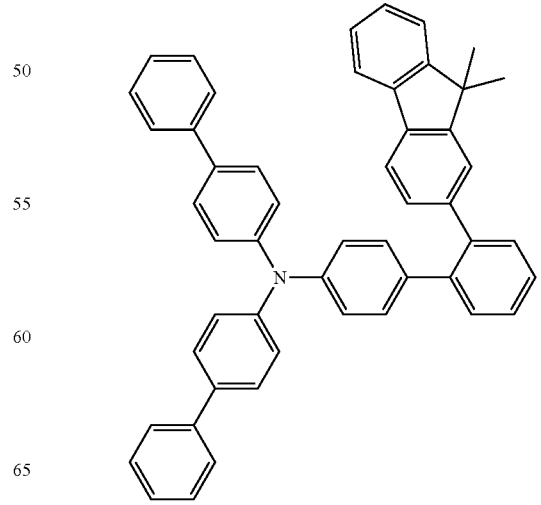

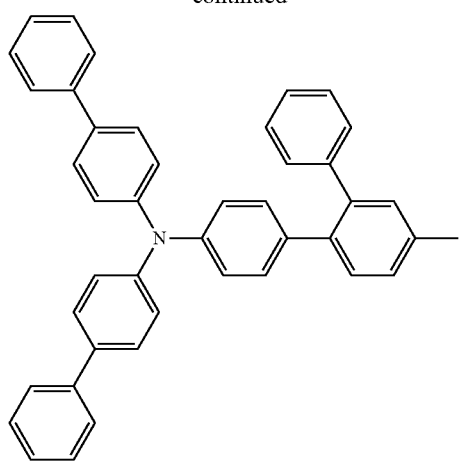
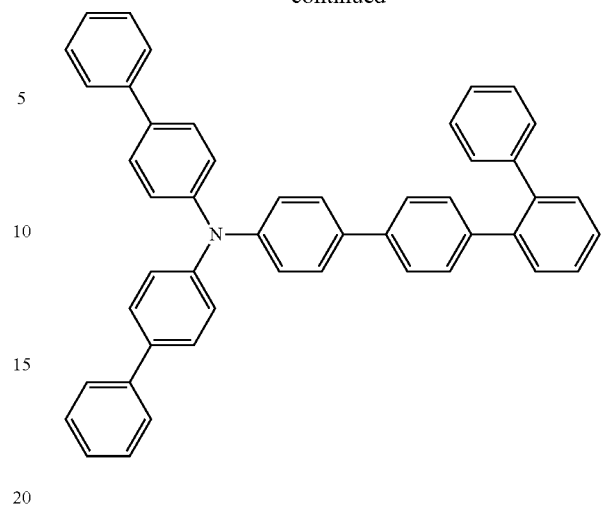
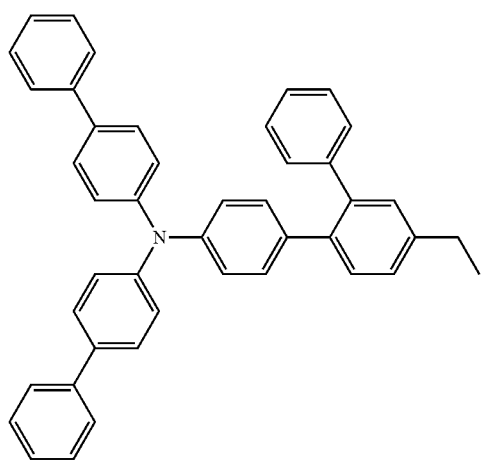
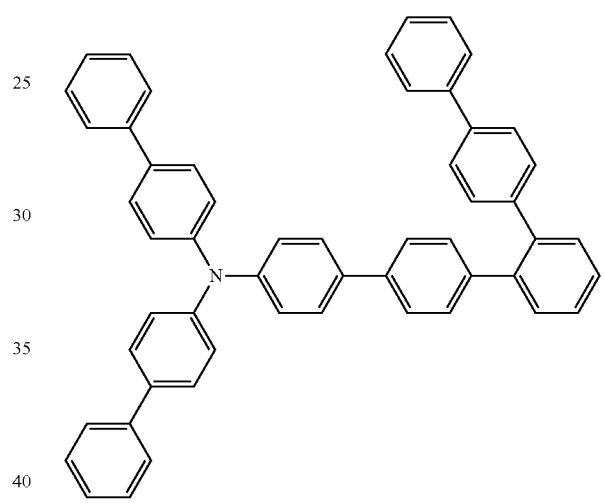
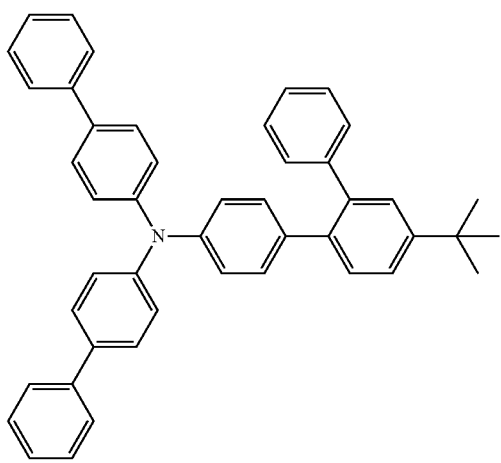
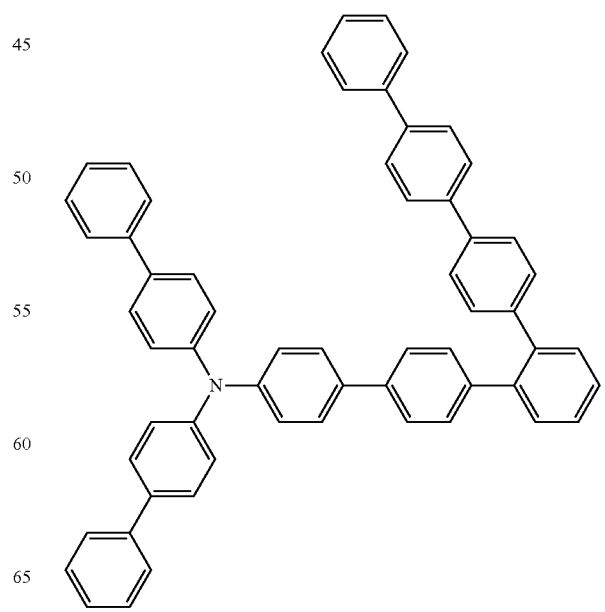

[Chemical Formula 16]
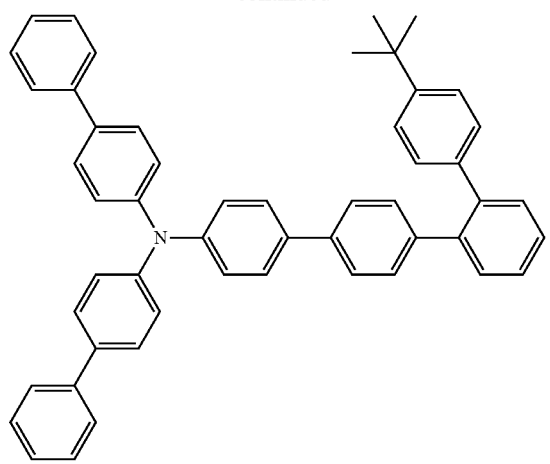
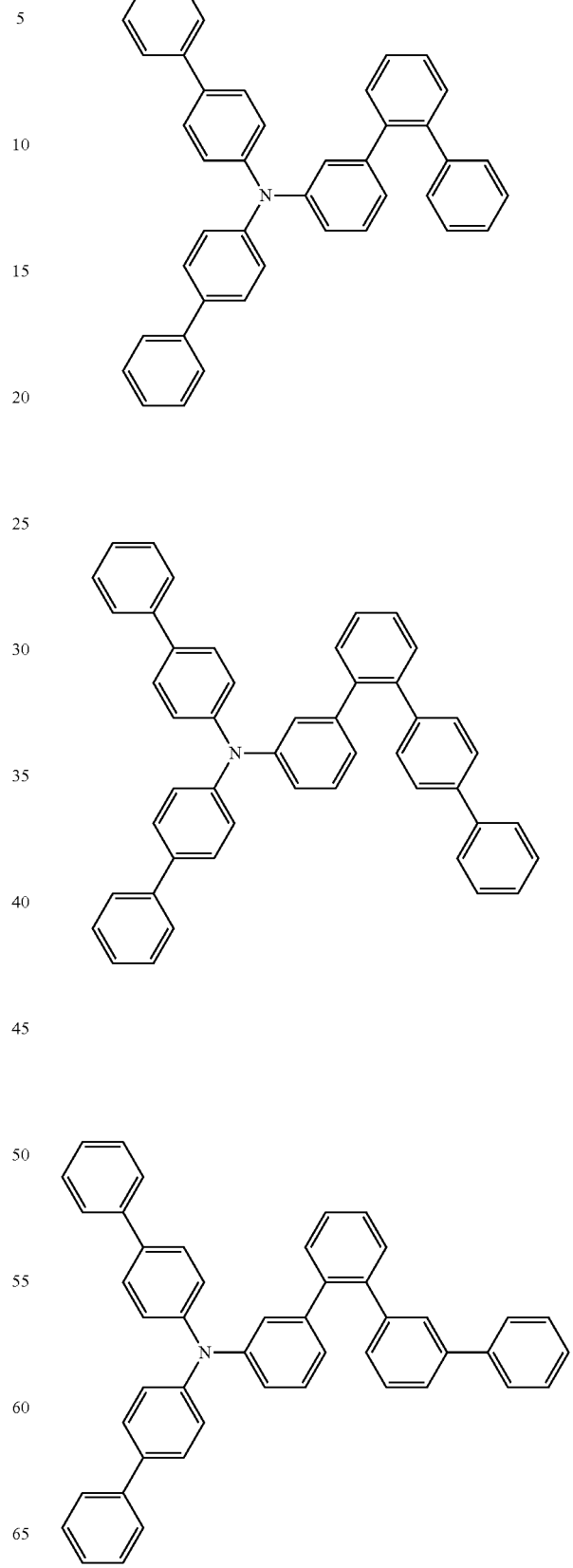

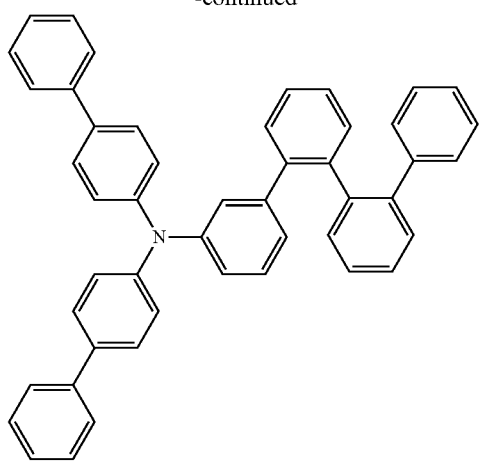
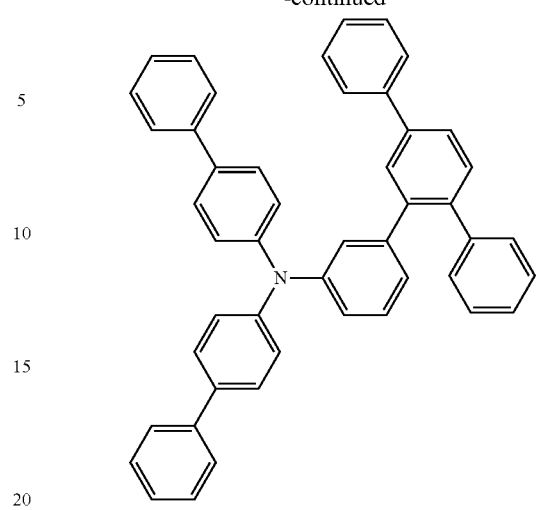
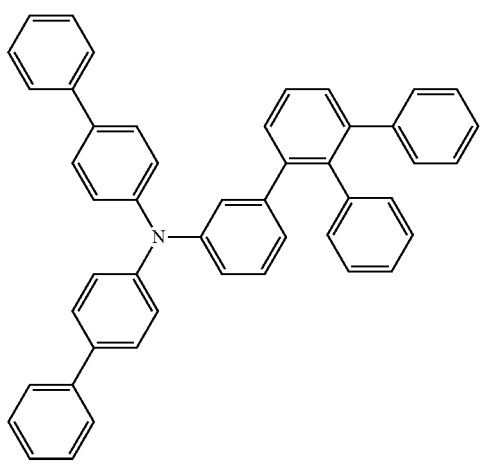
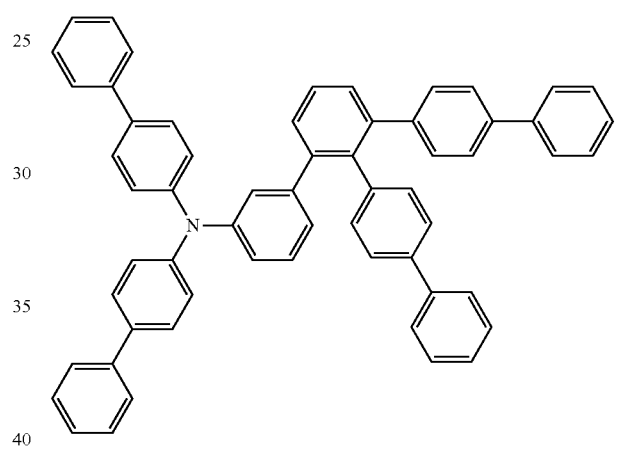
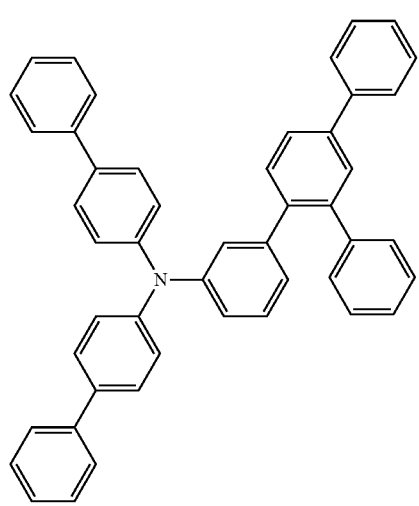
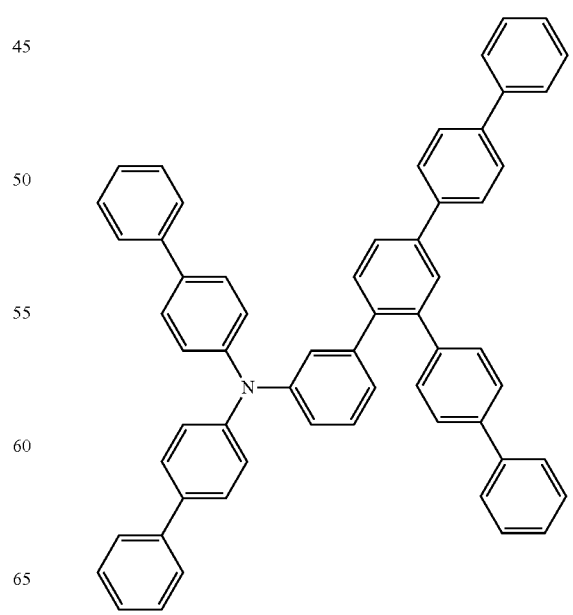

[Chemical Formula 17]
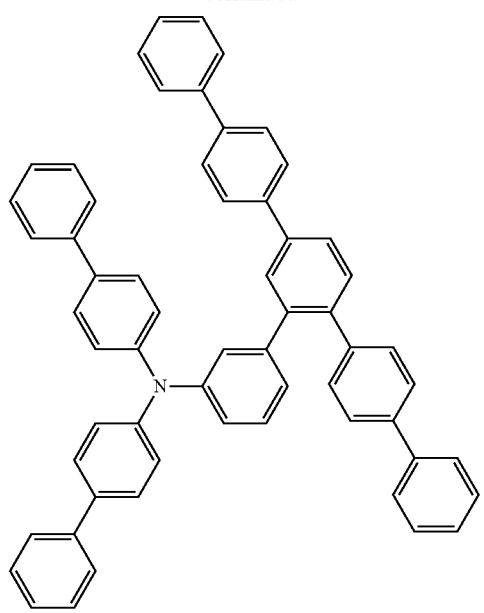
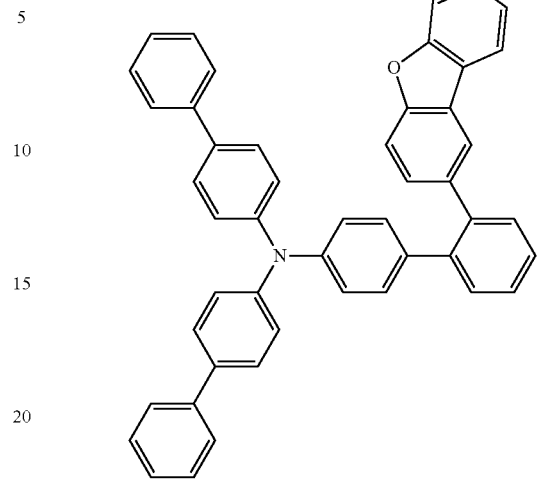
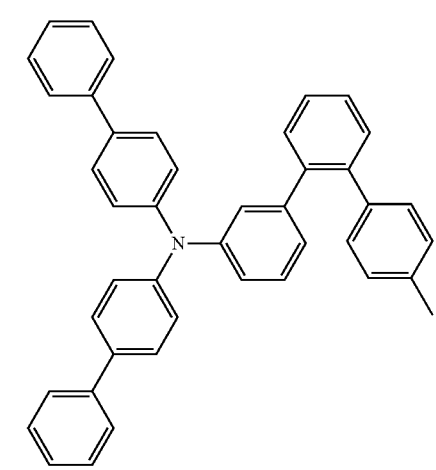
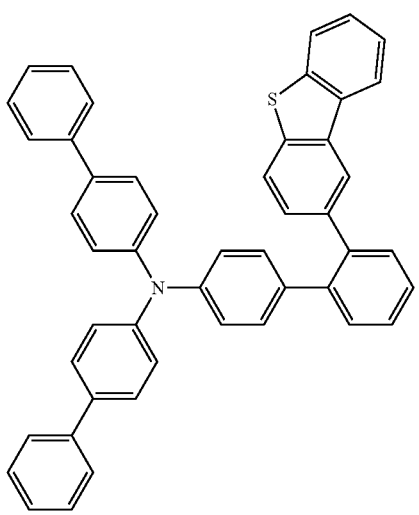
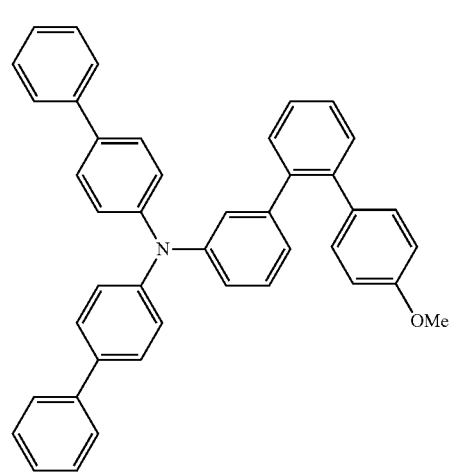
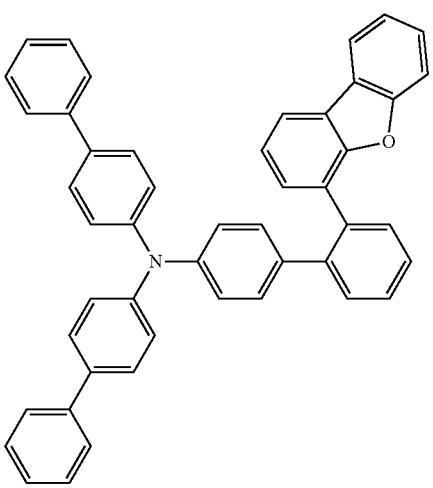

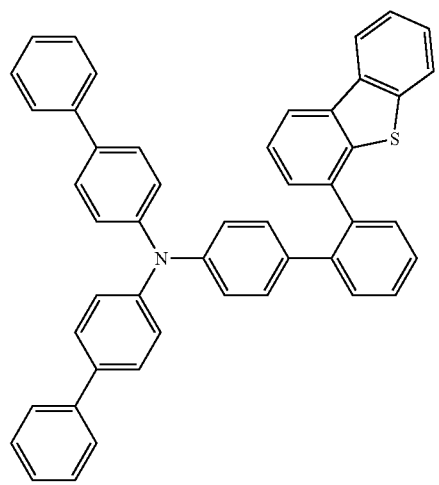
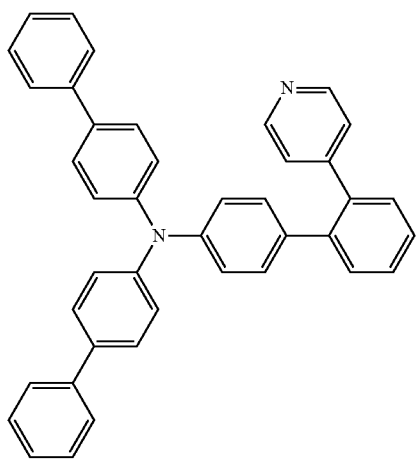
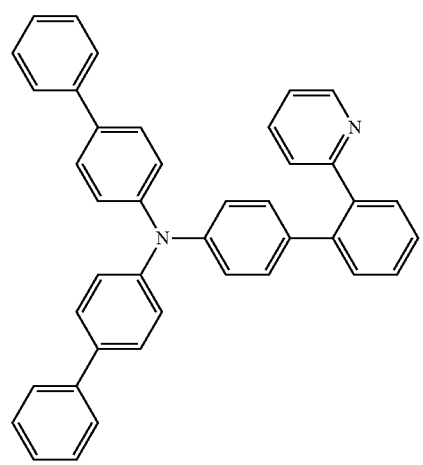
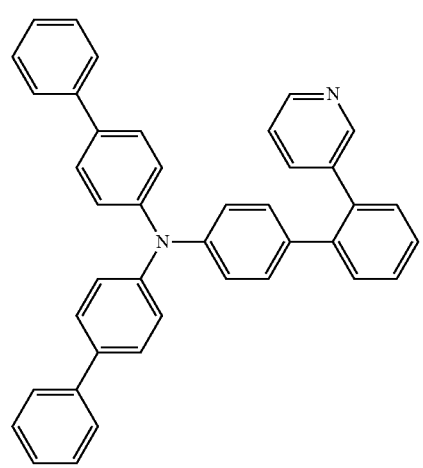
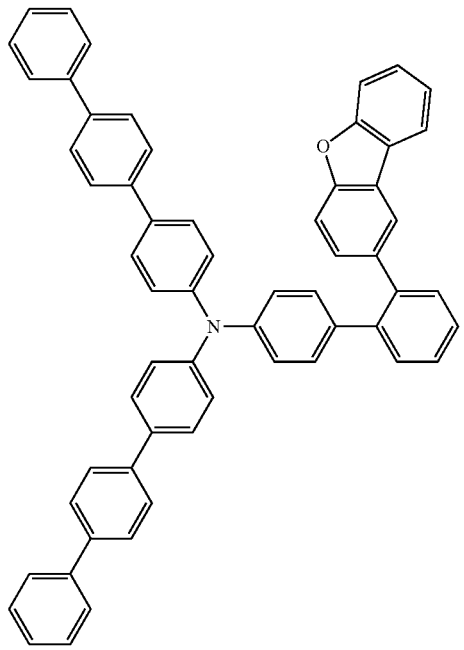

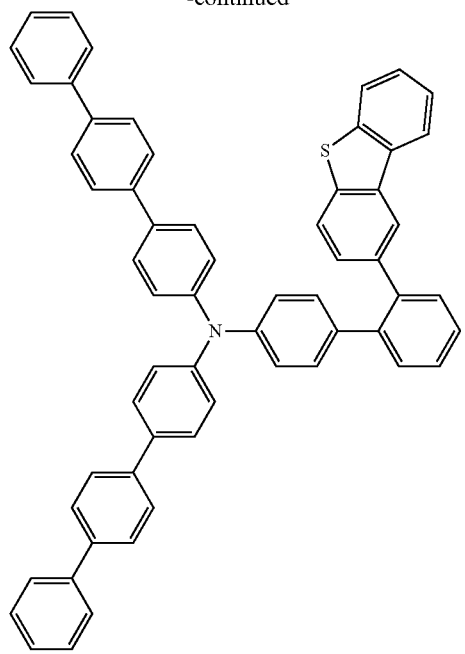
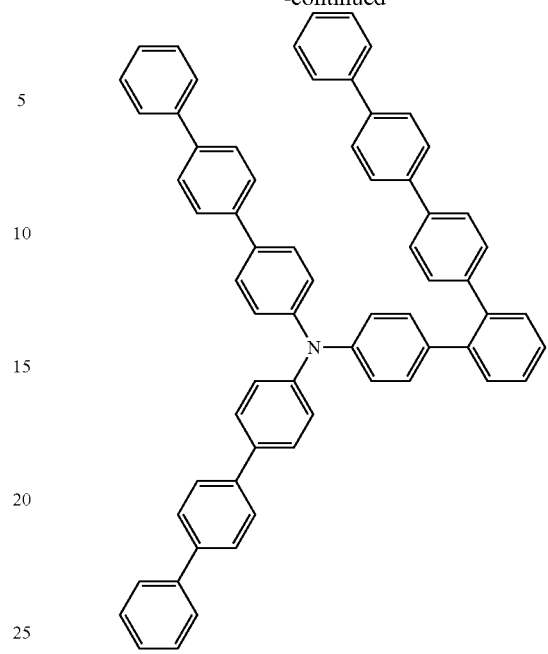
[Chemical Formula 18]
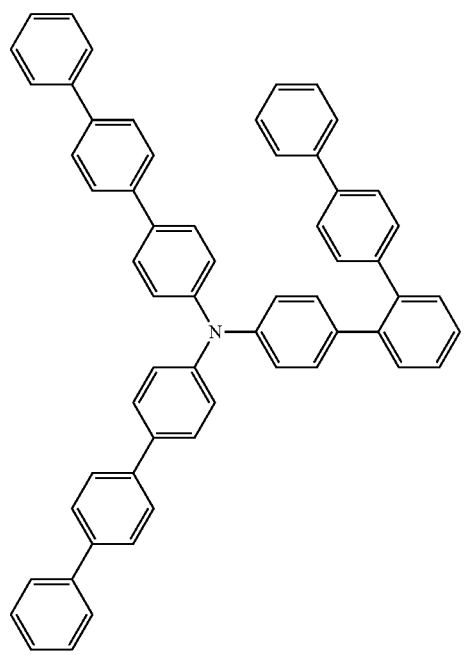
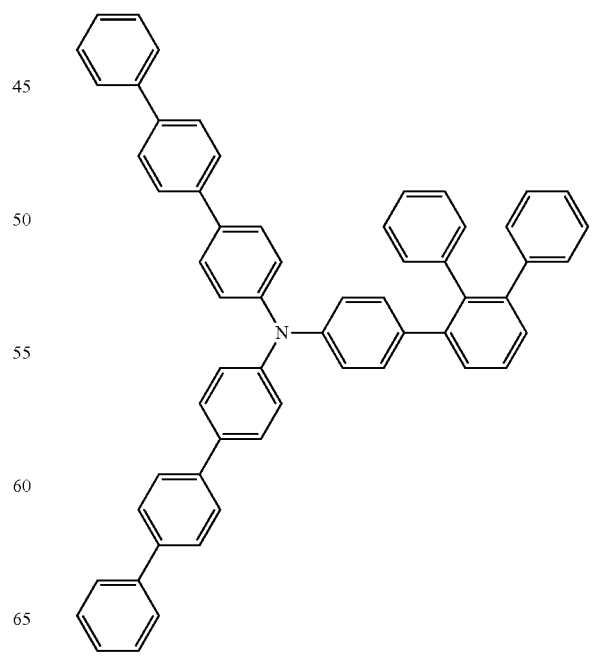

-continued
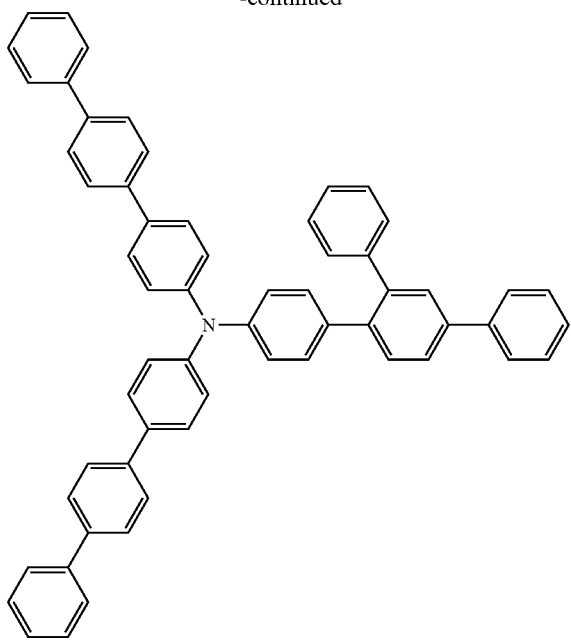
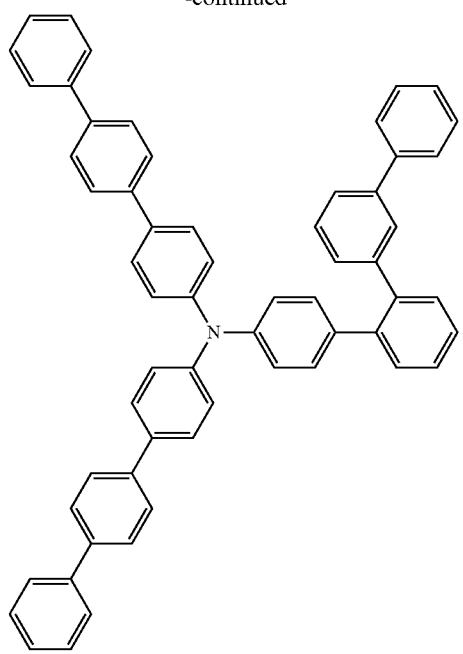
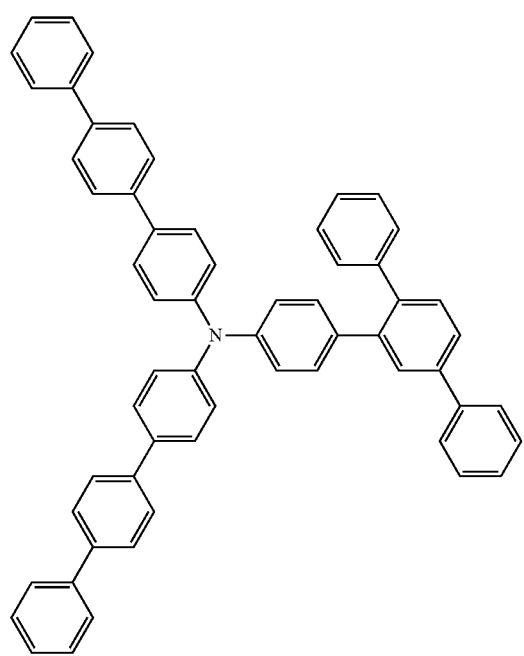
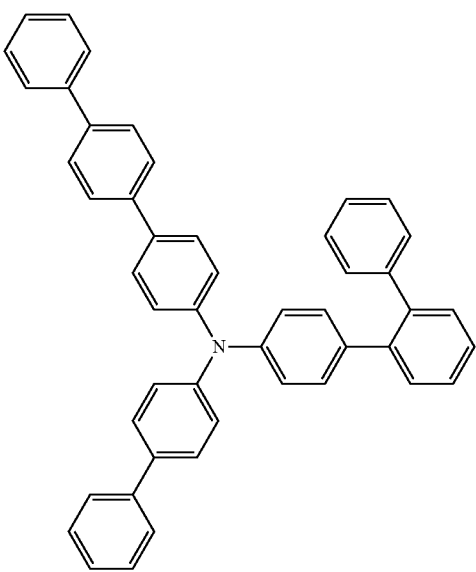

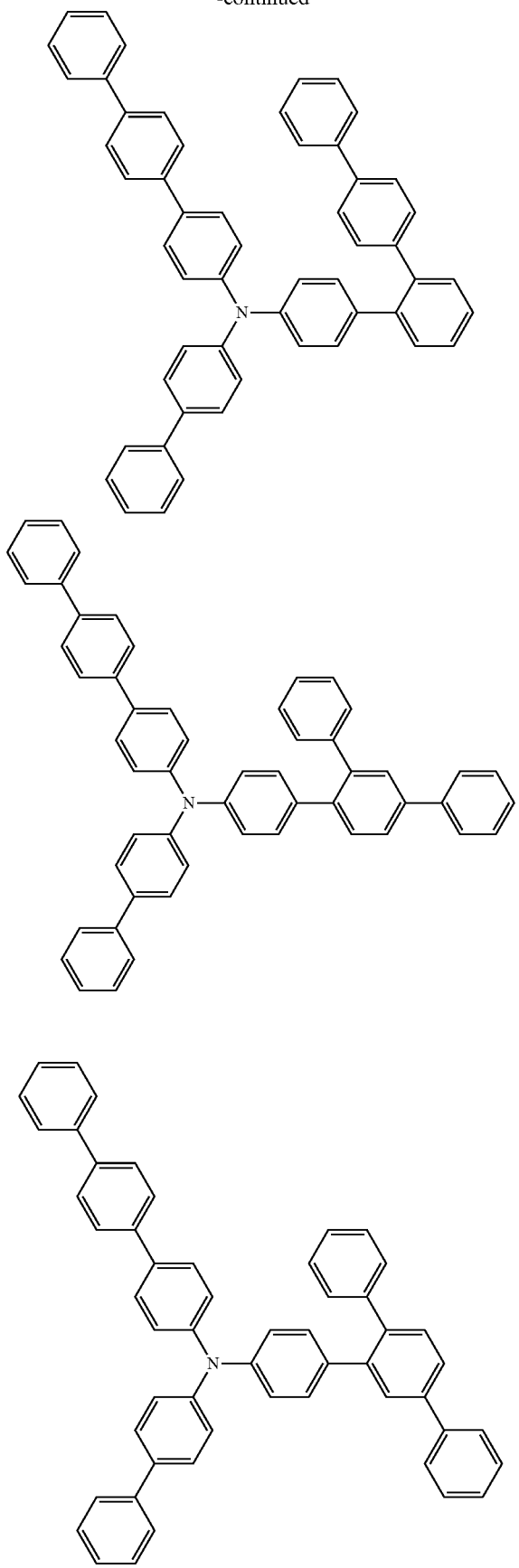
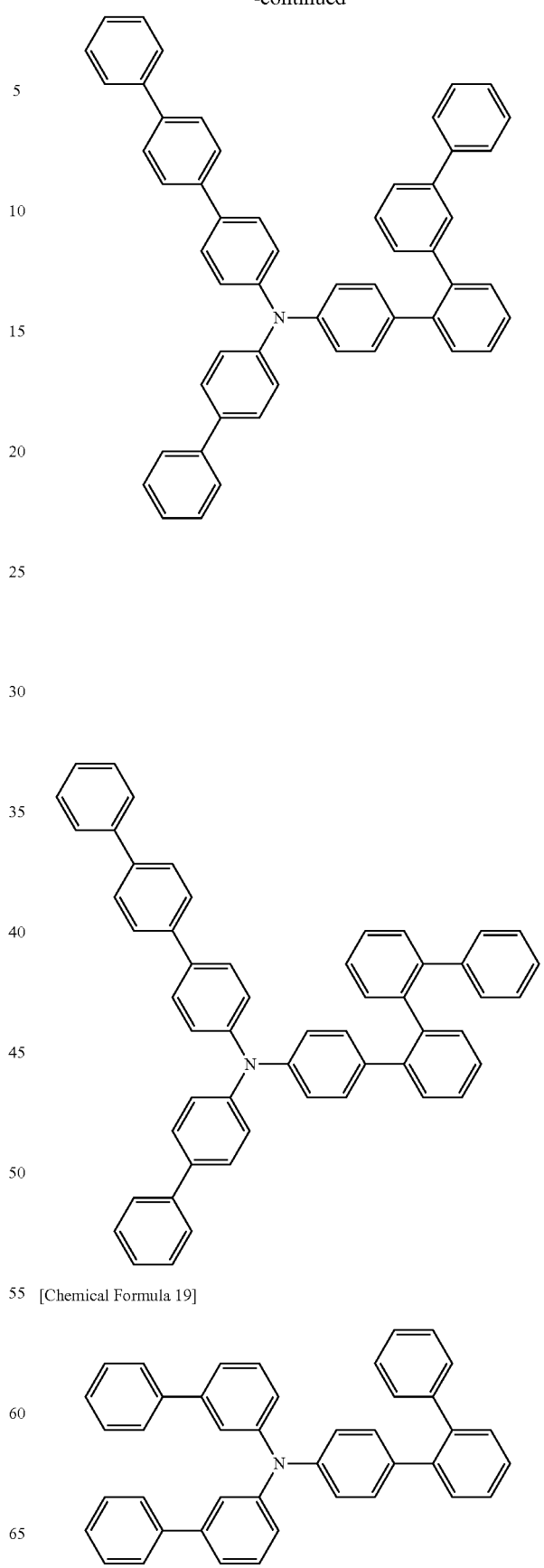
[Chemical Formula 19]

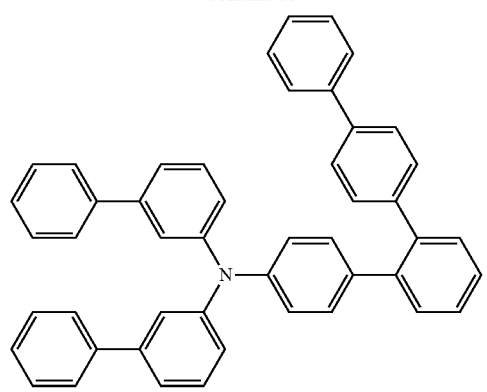
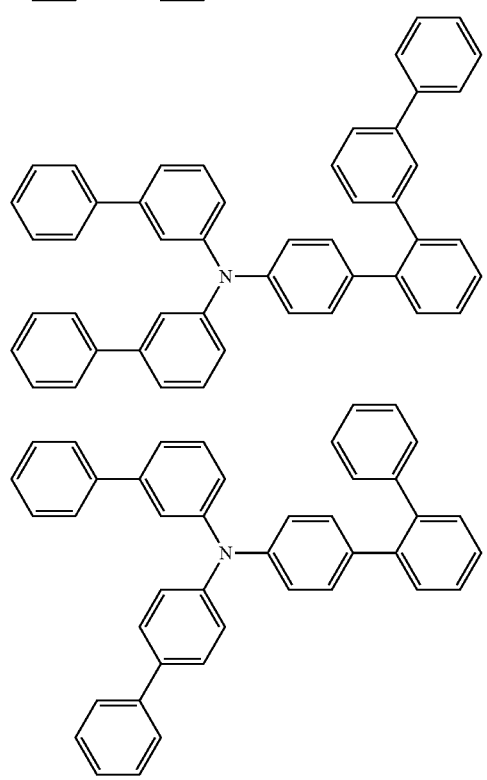
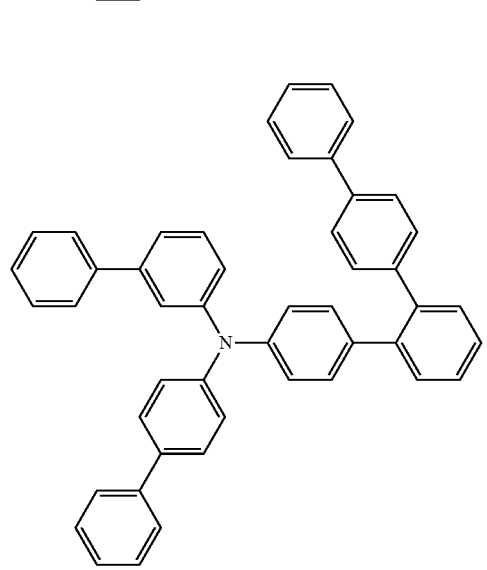
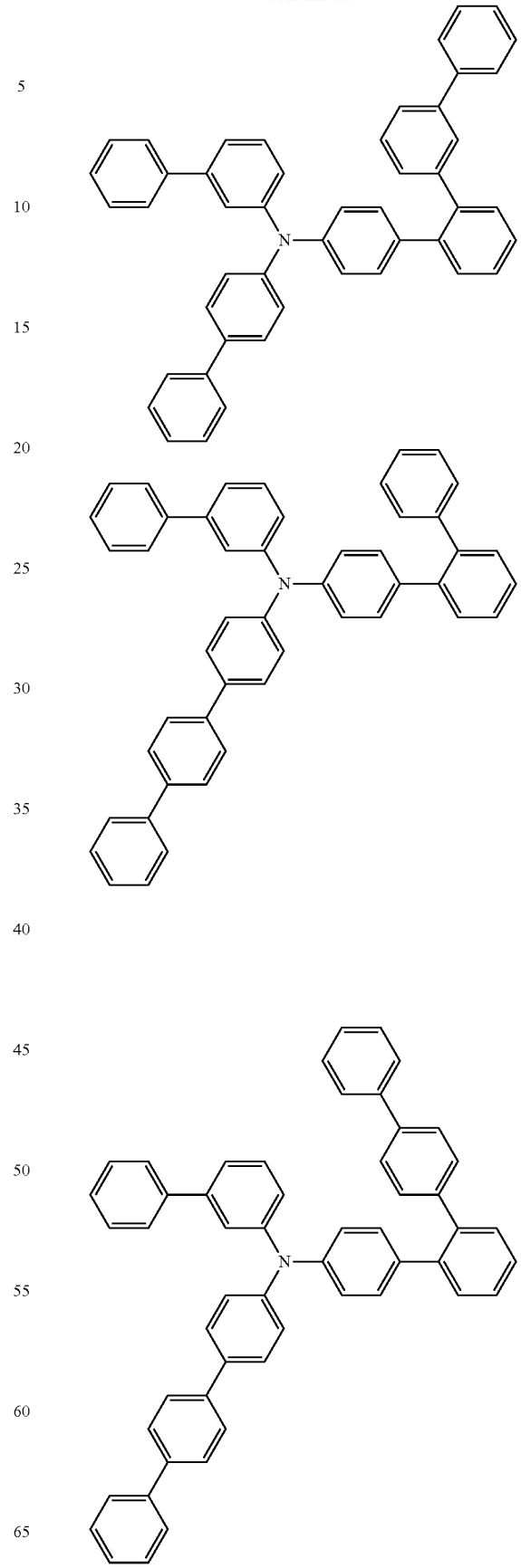

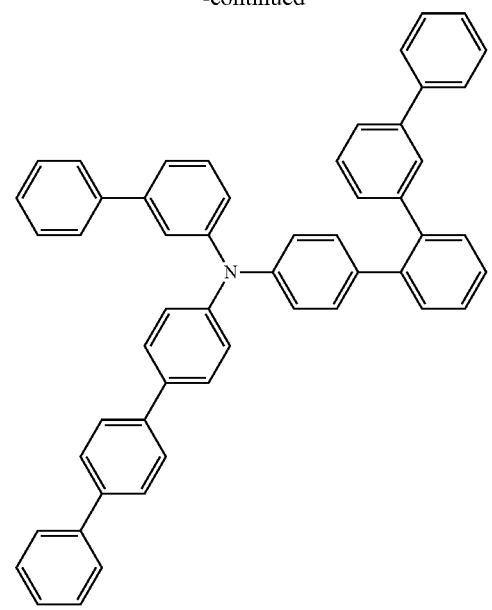
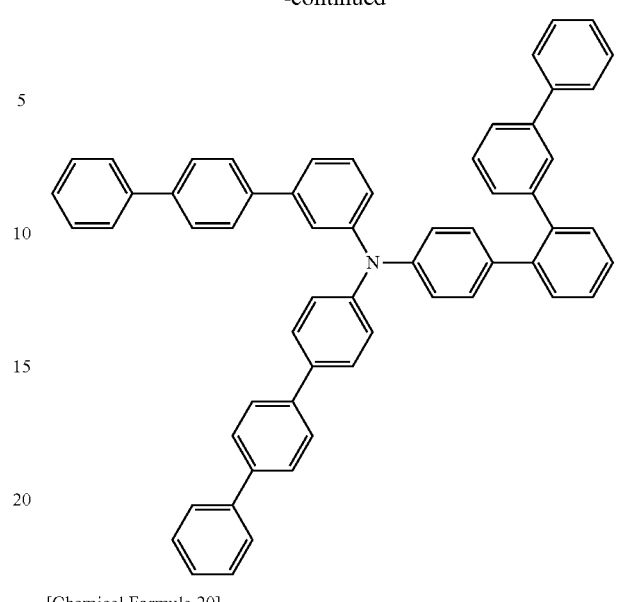
[Chemical Formula 20]
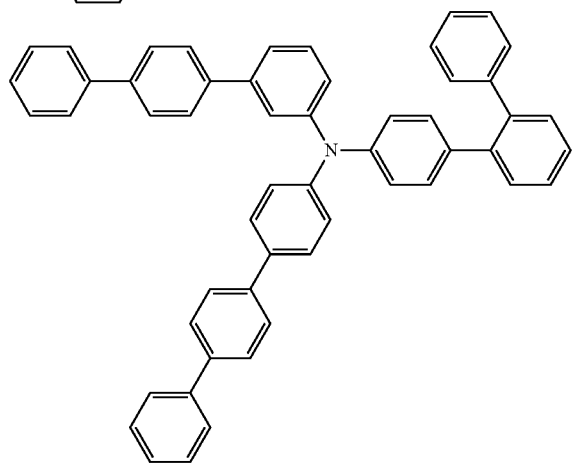
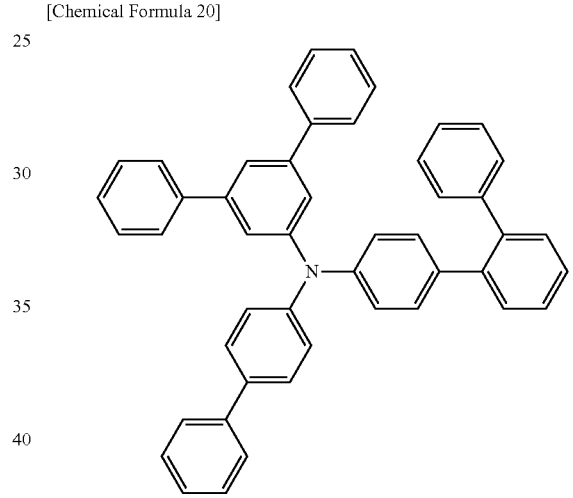
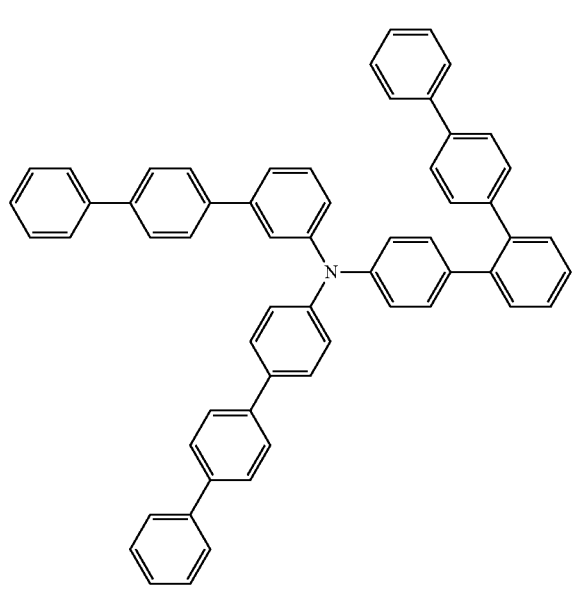
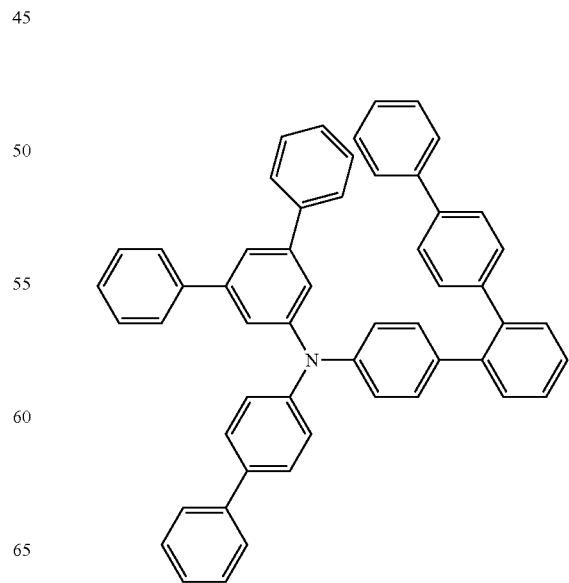

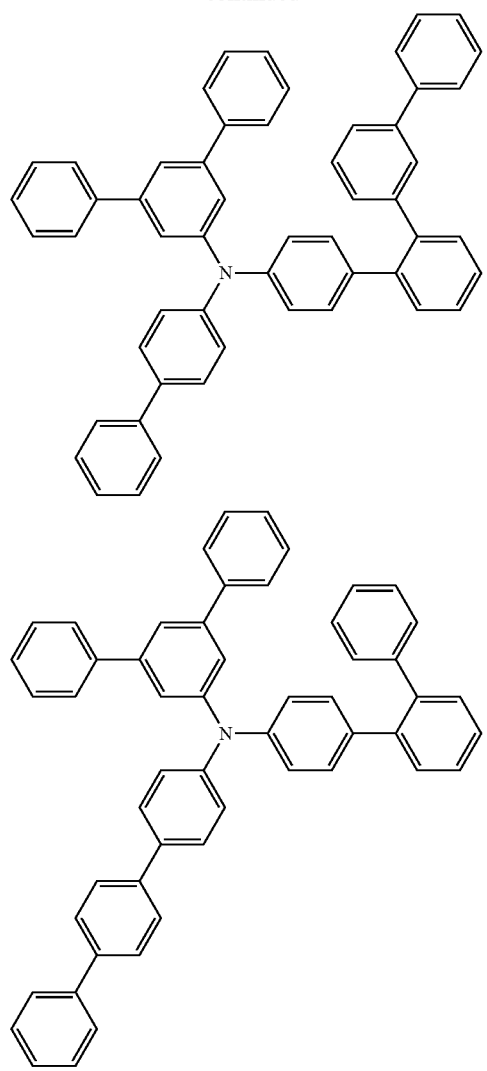
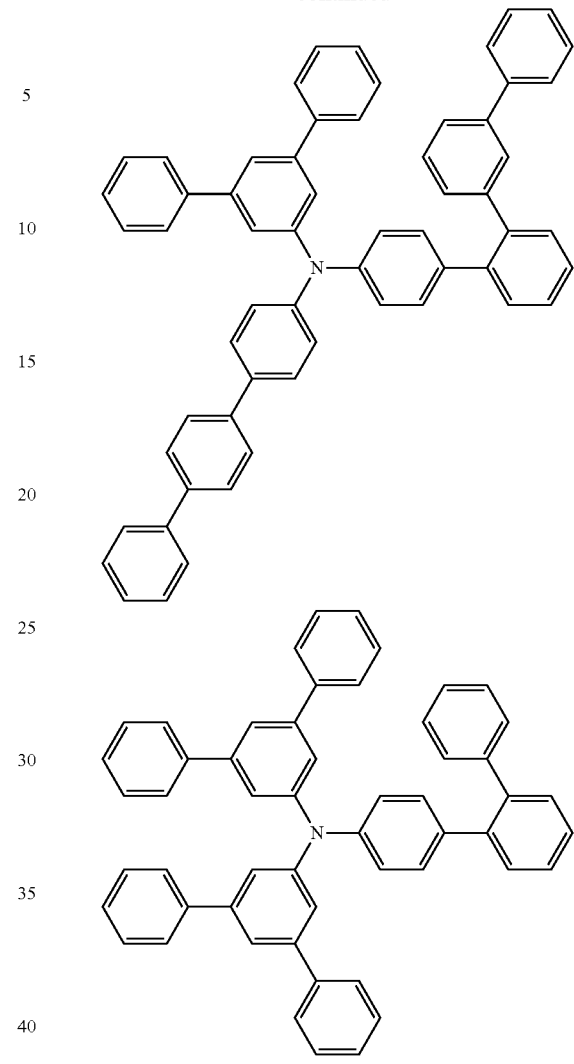
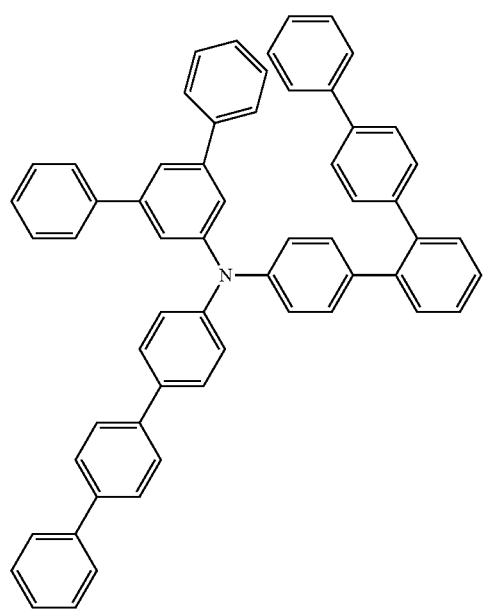
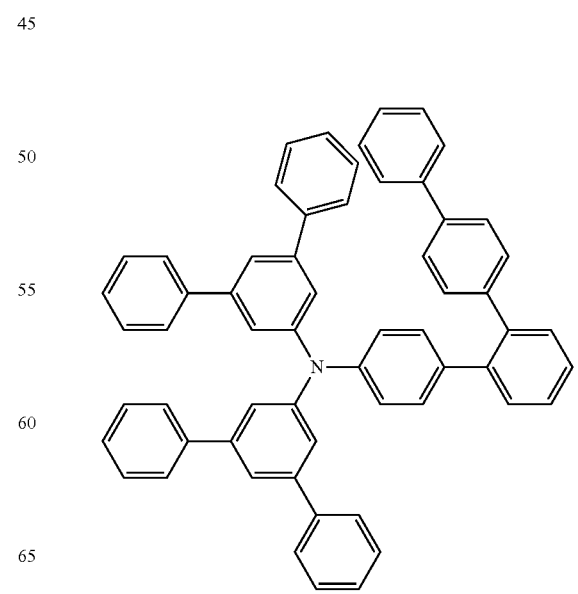

[Chemical Formula 21]
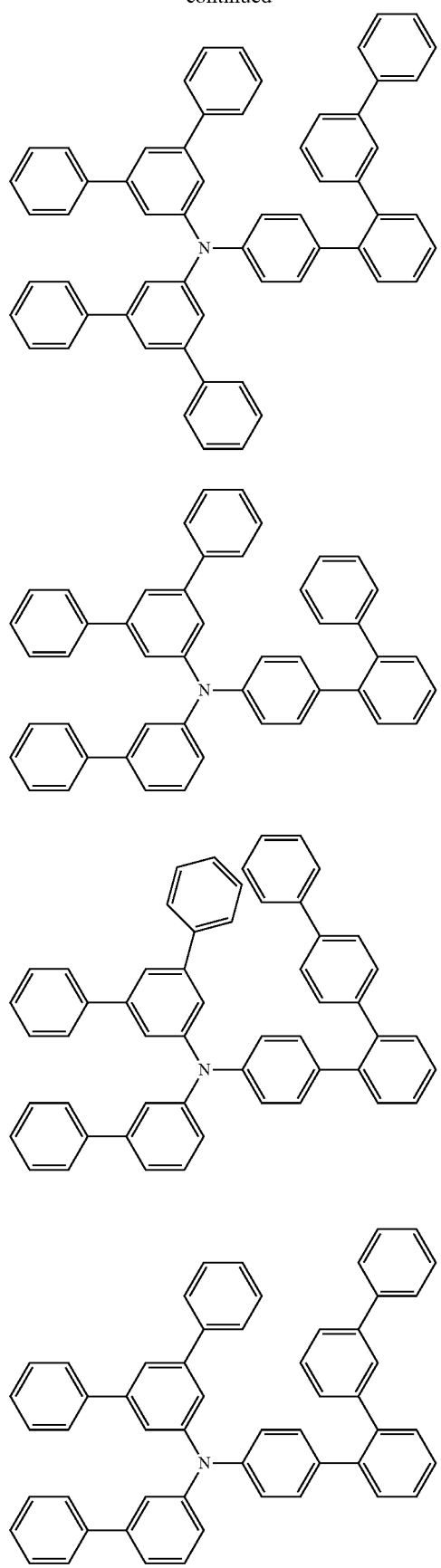
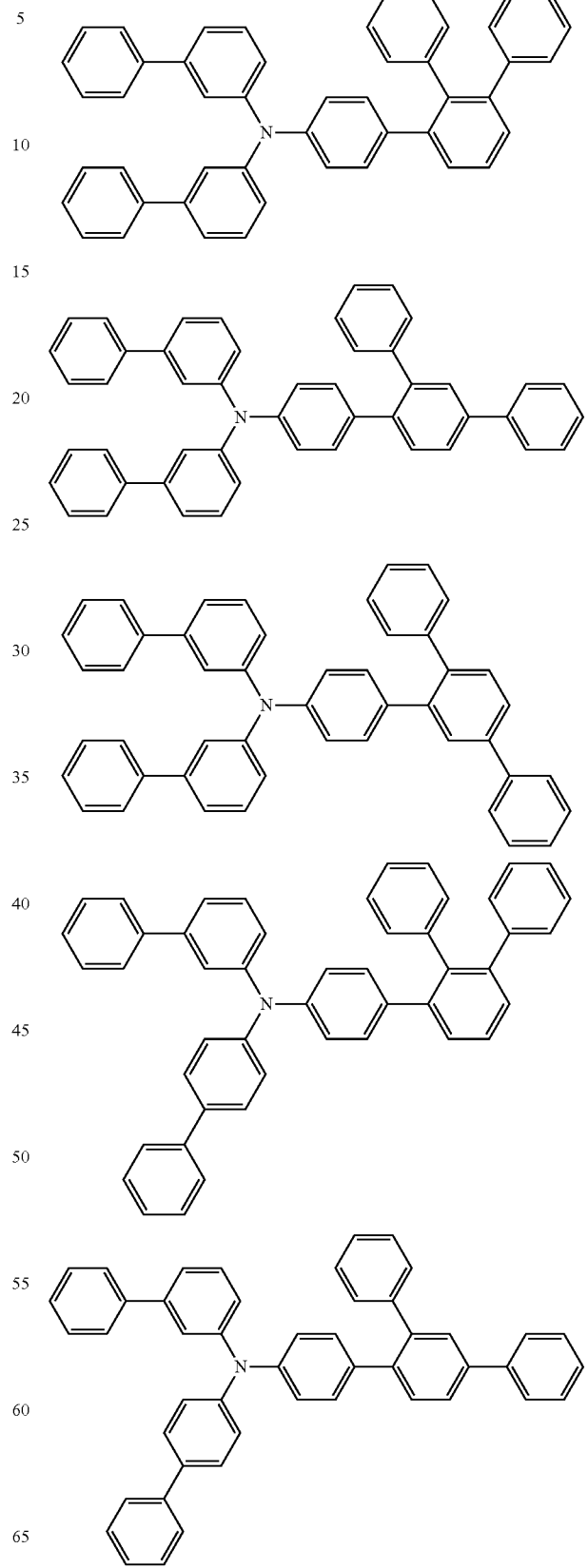

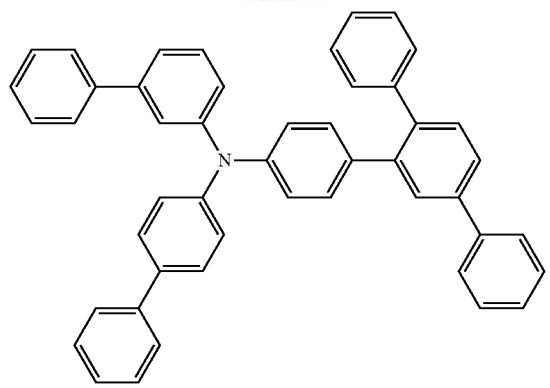
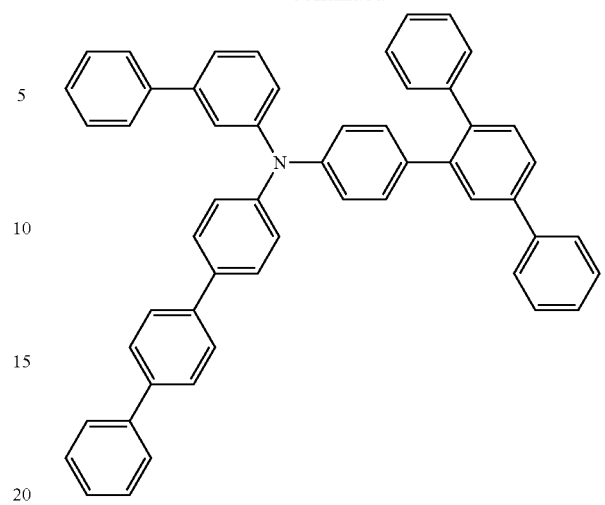
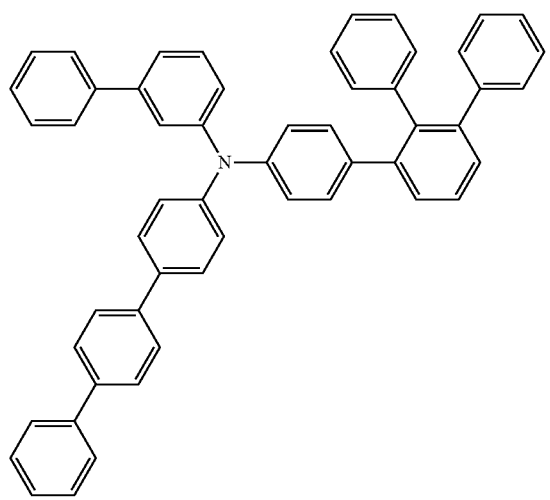
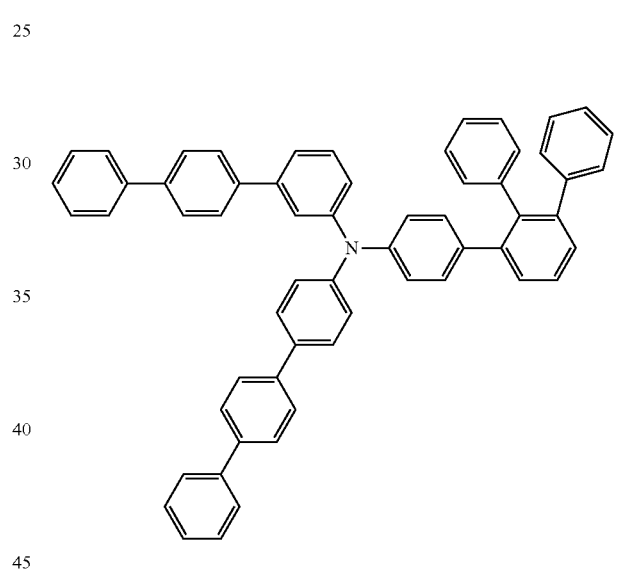
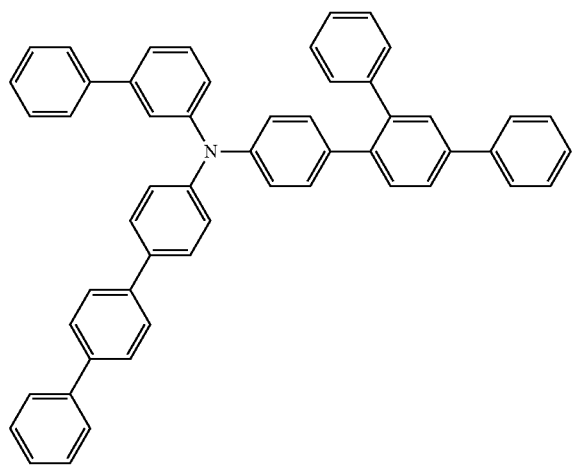
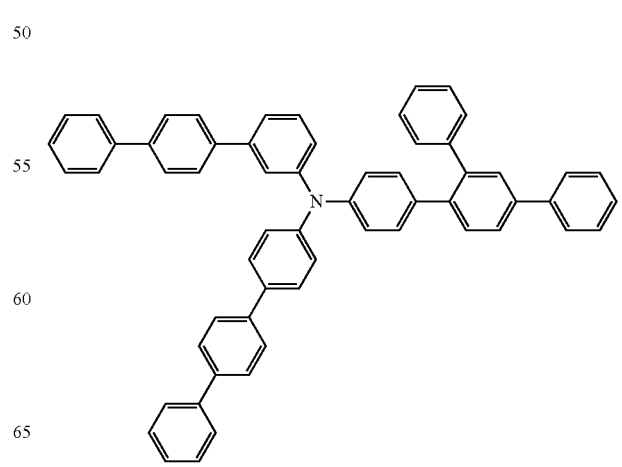

51
-continued
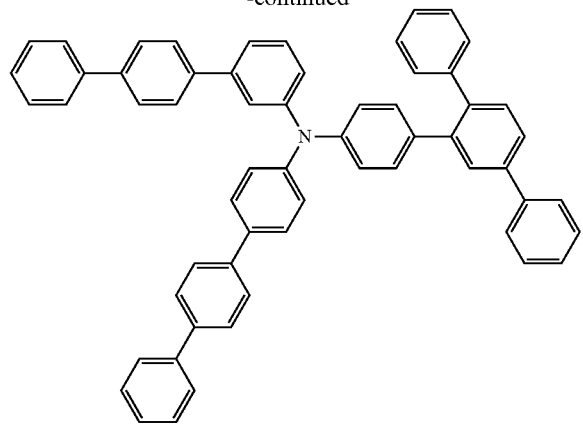
[Chemical Formula 22]
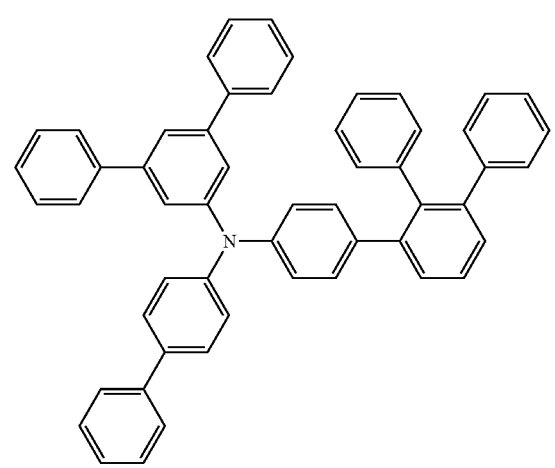
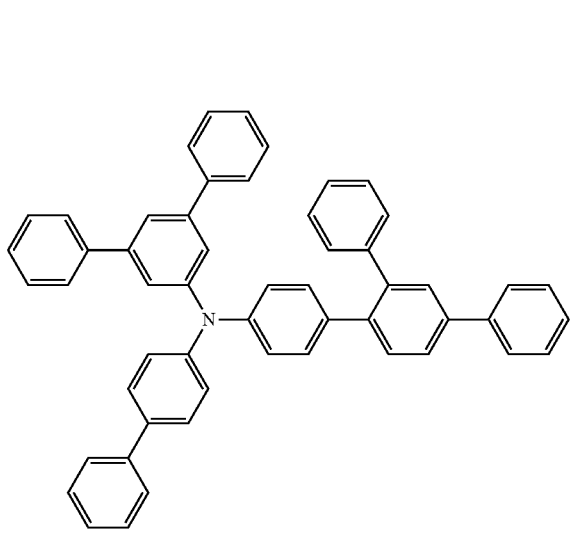
52
-continued
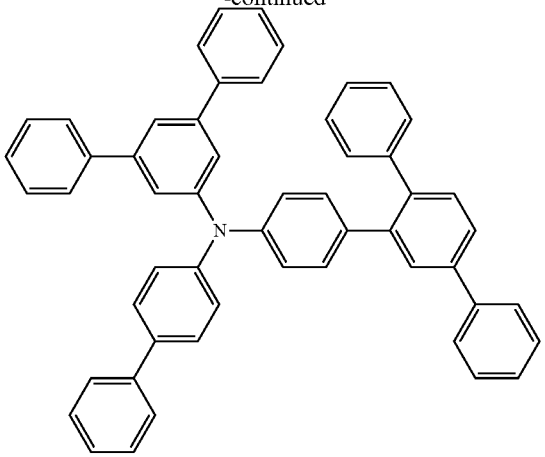
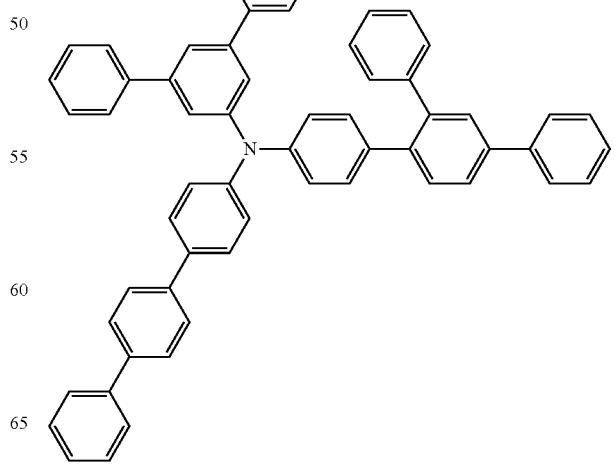

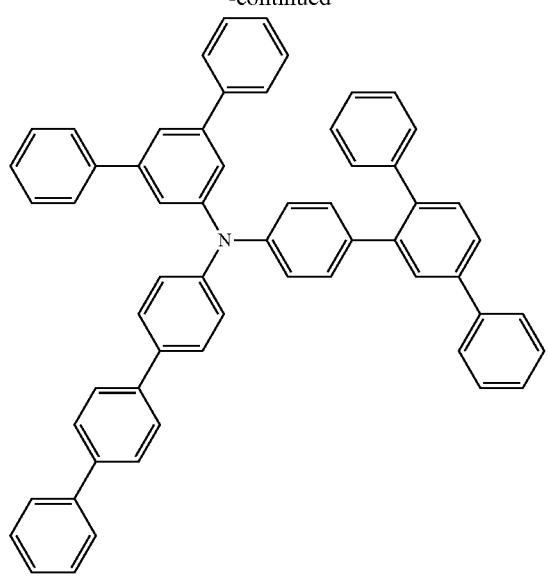
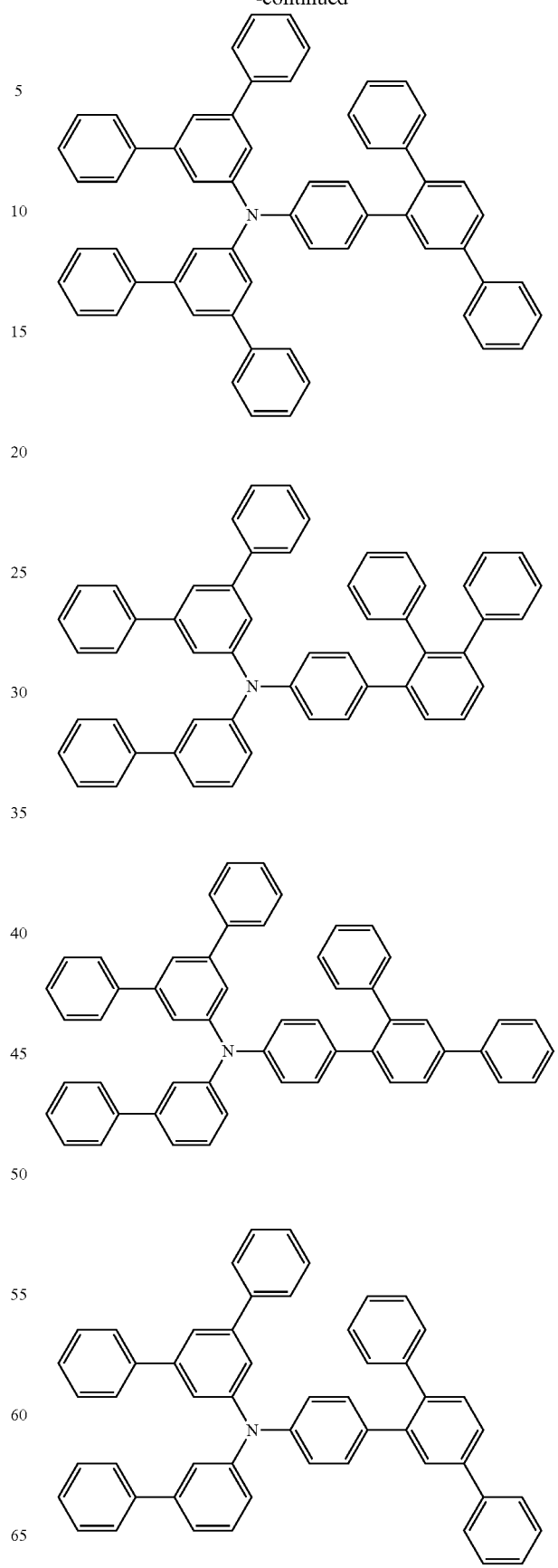

[Chemical Formula 23]
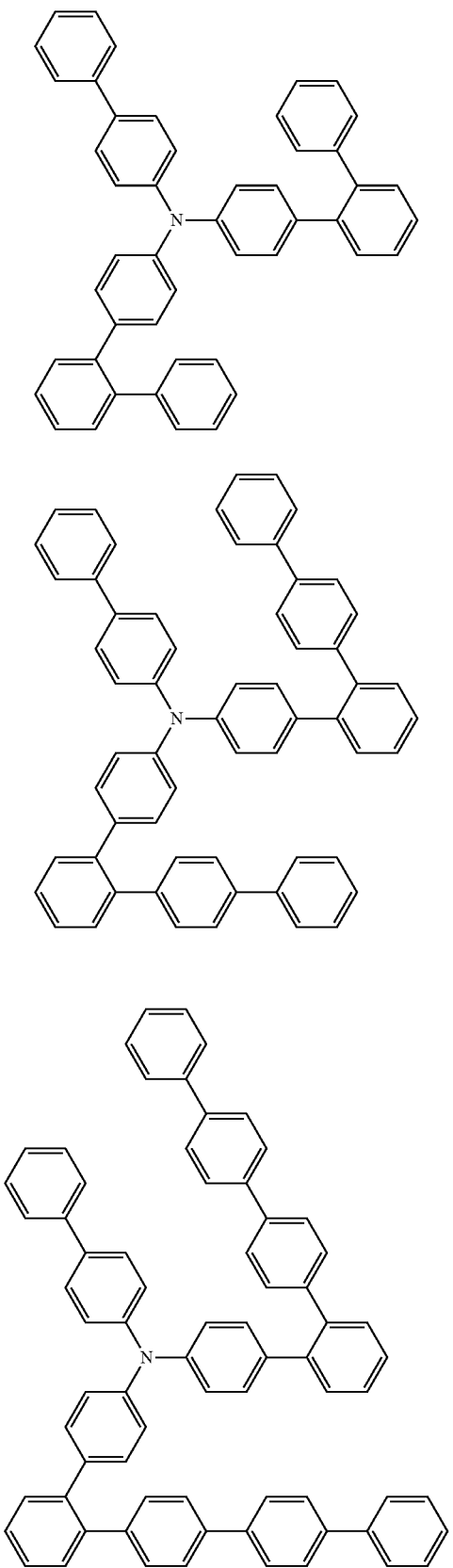
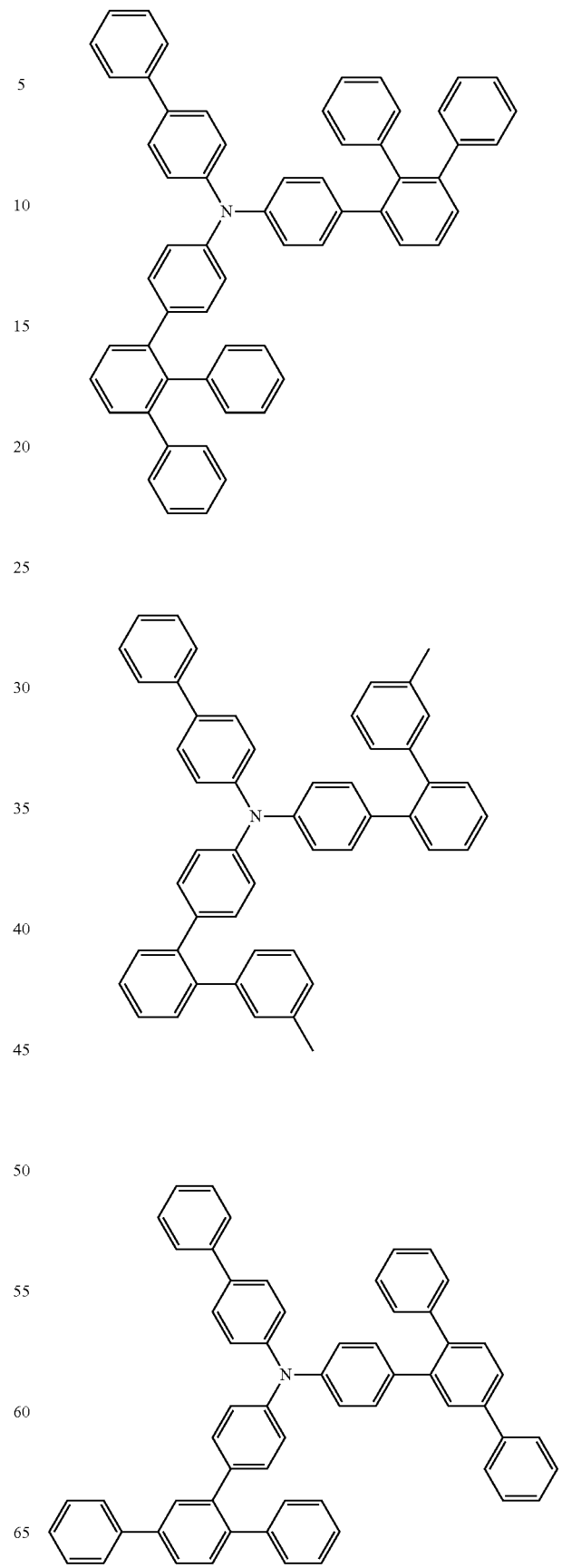

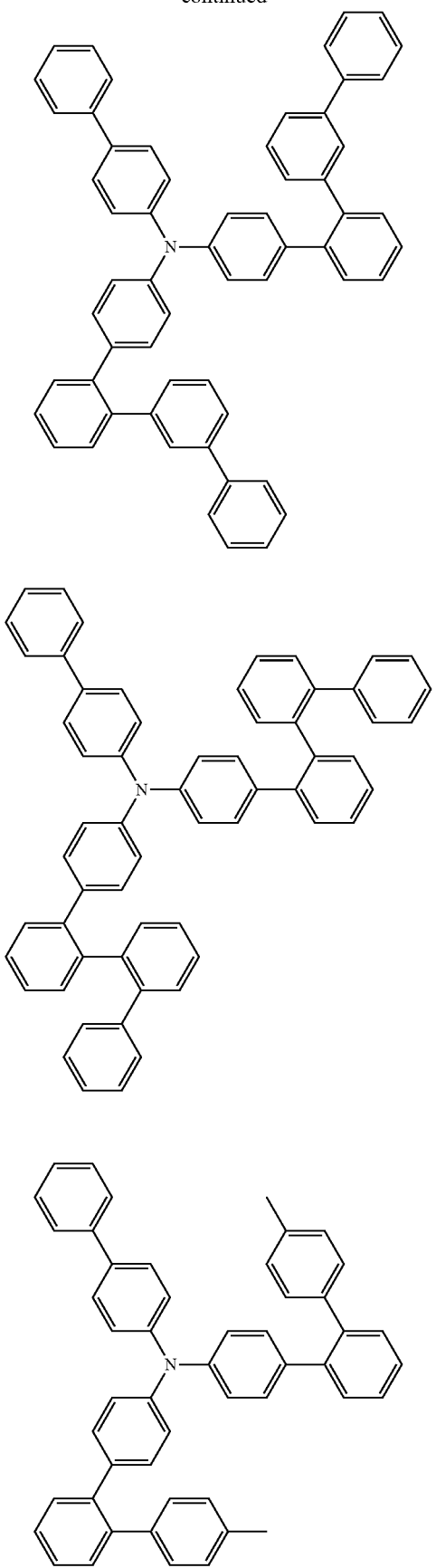
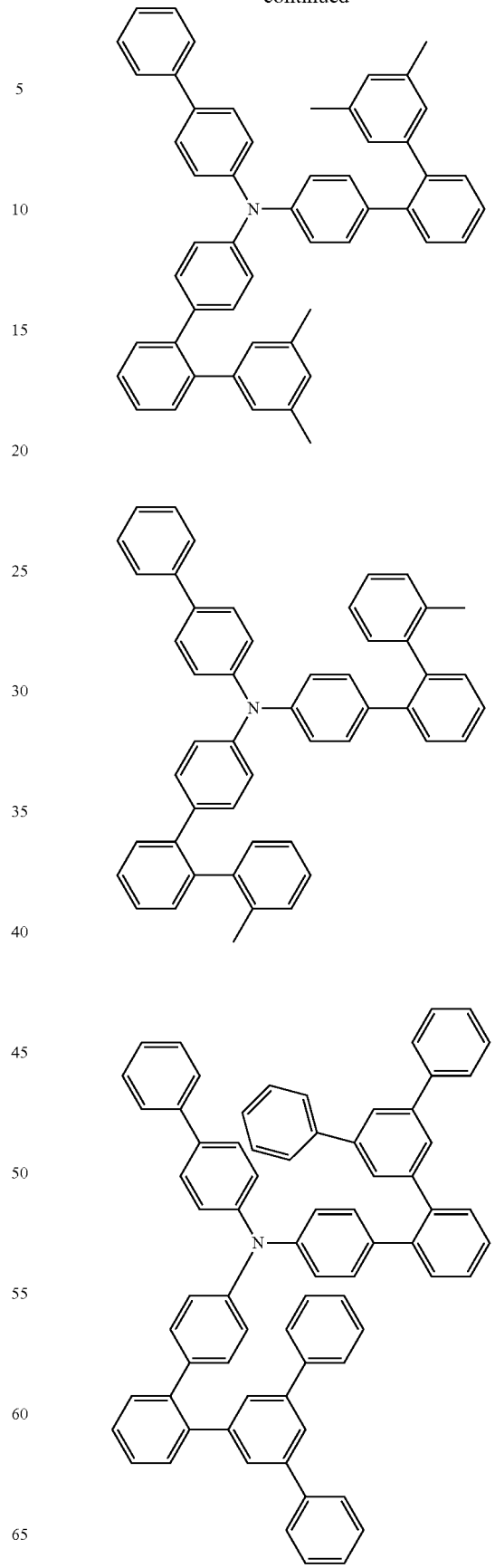

-continued
[Chemical Formula 24]
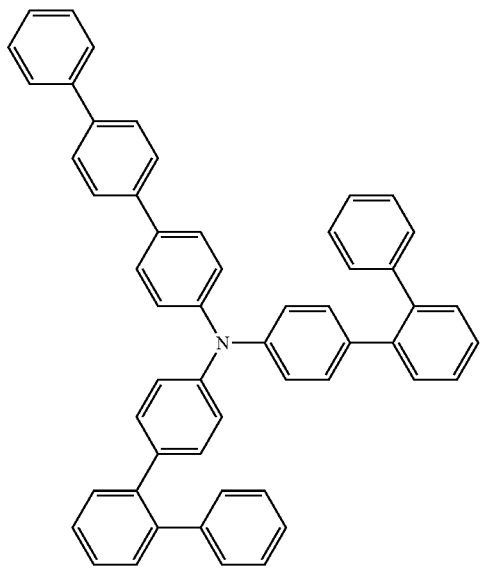
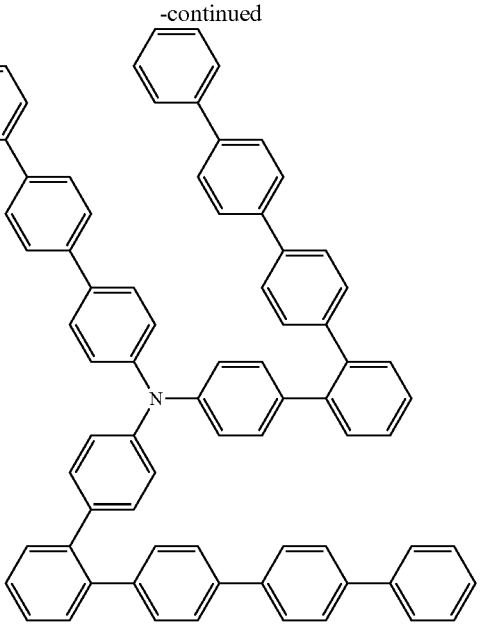
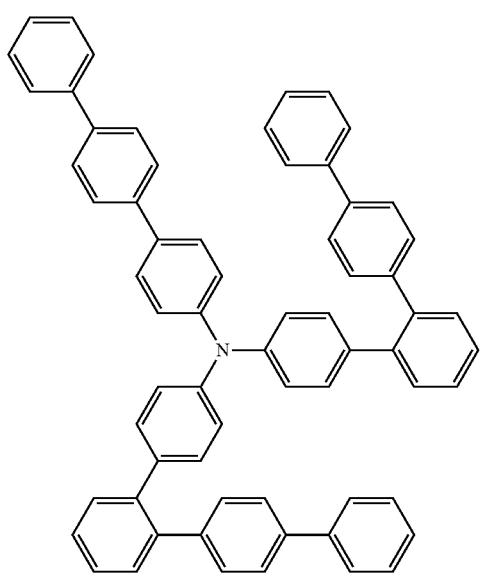
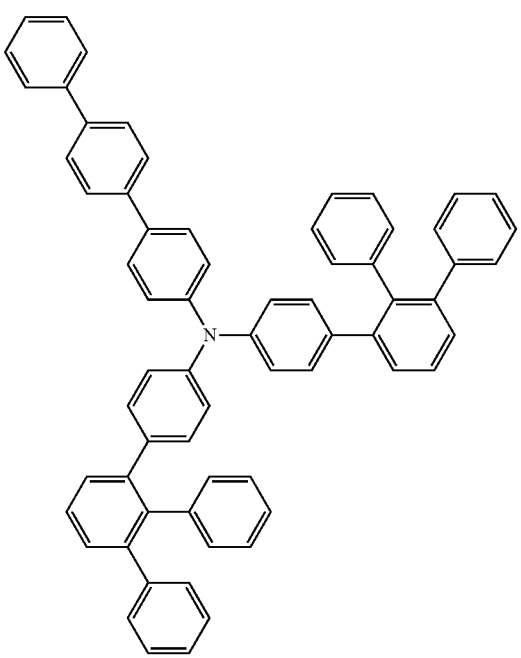

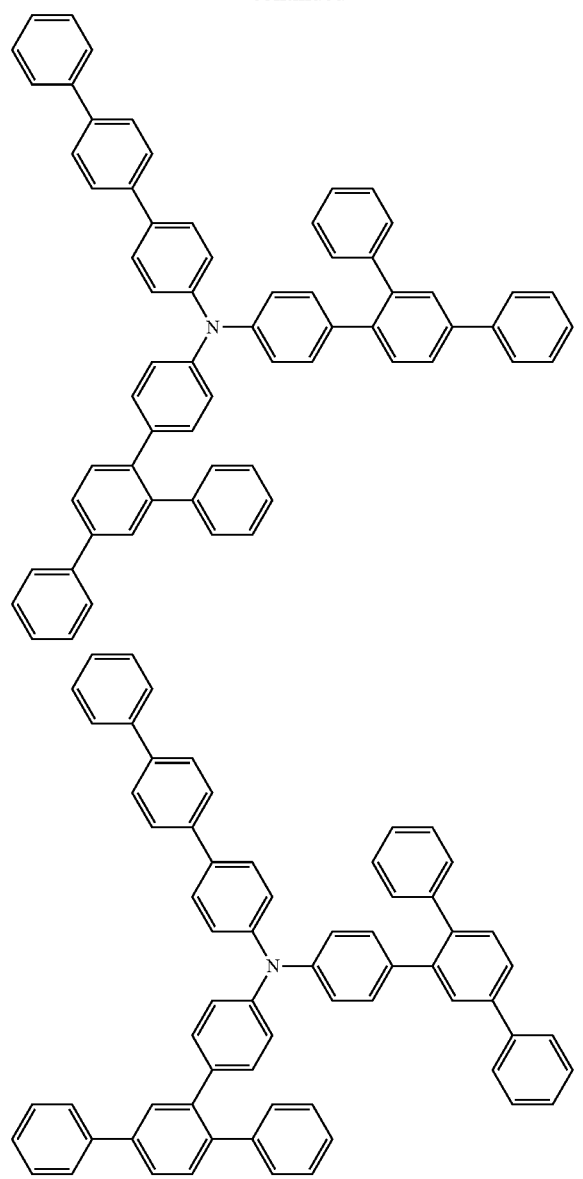
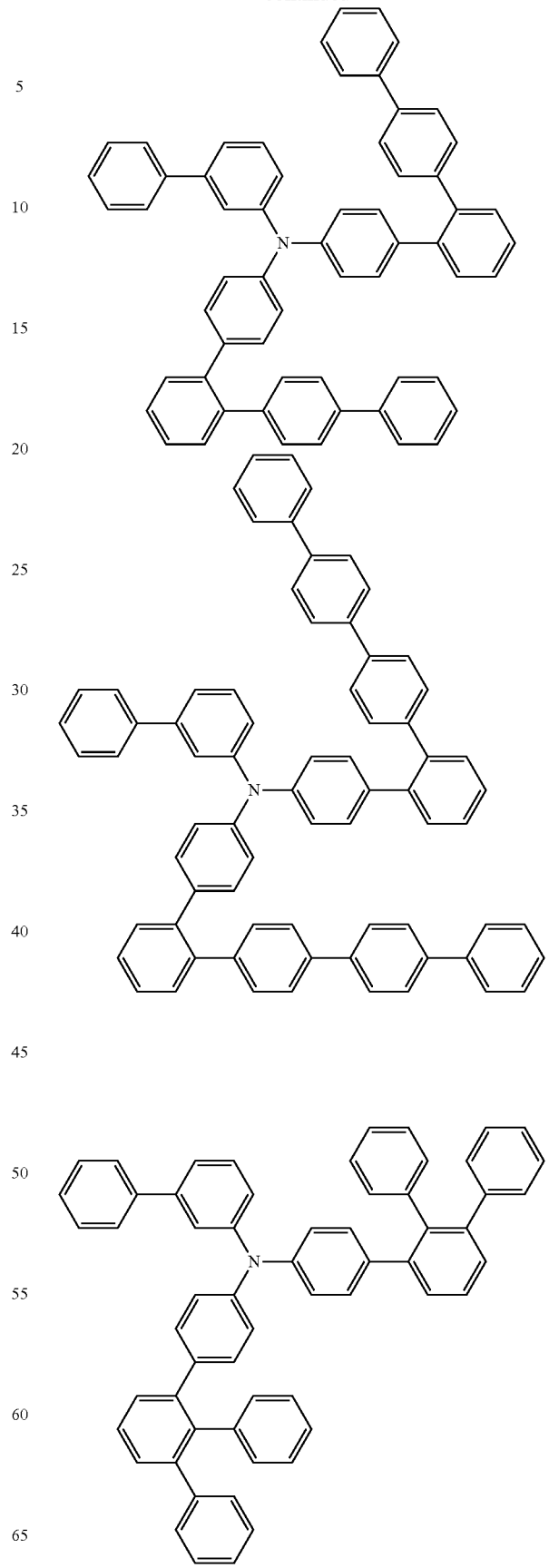

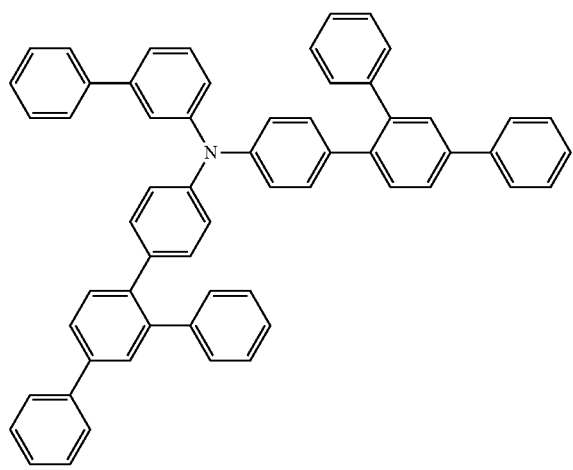
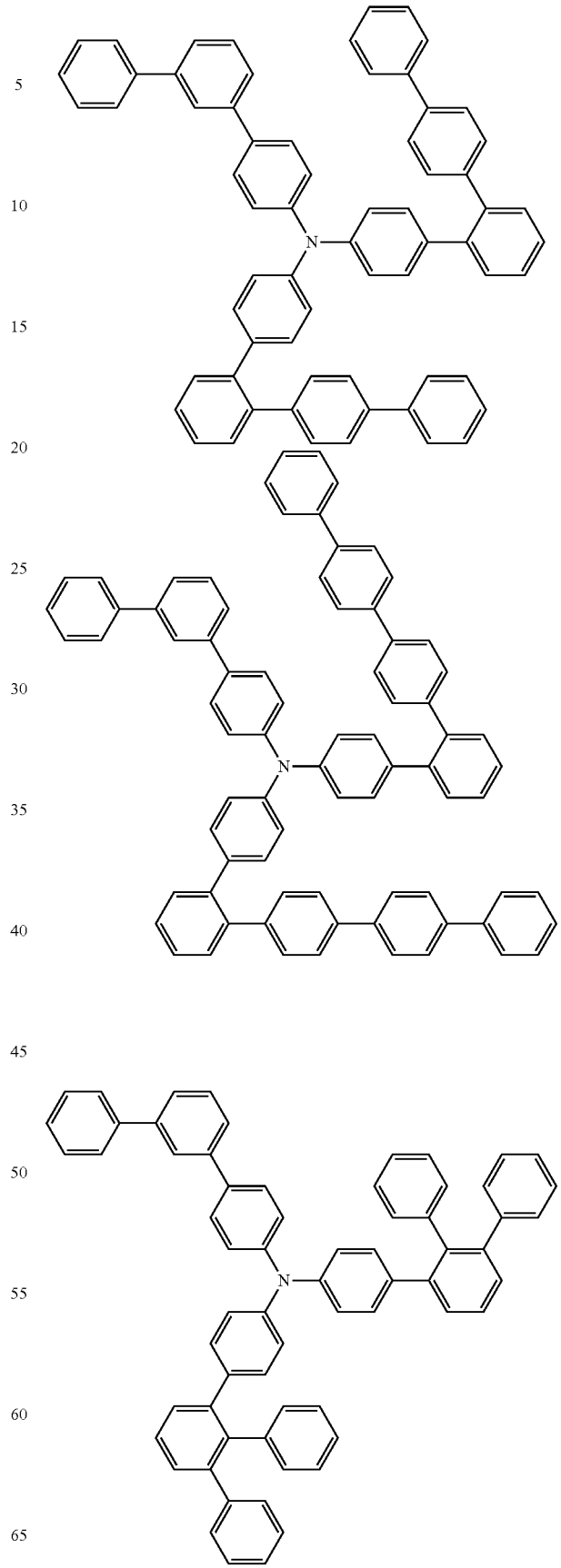

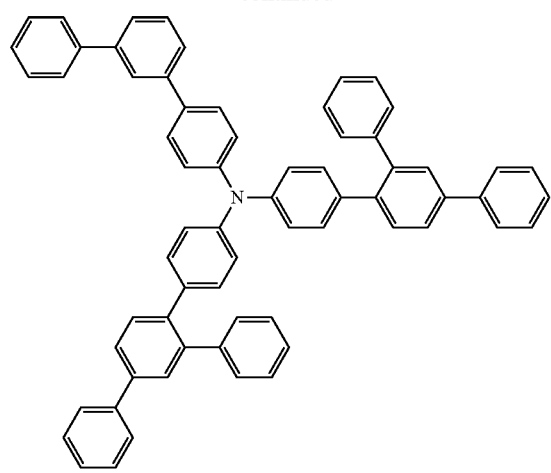
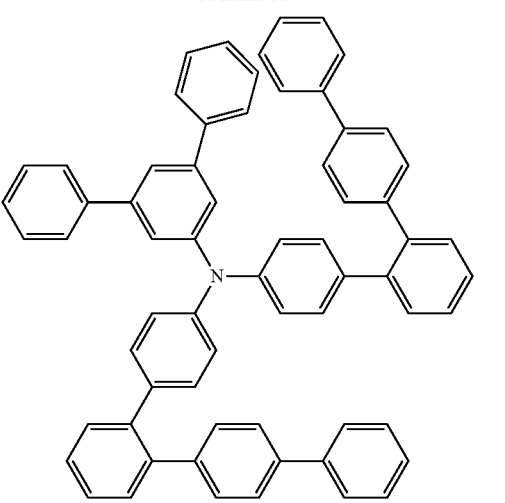
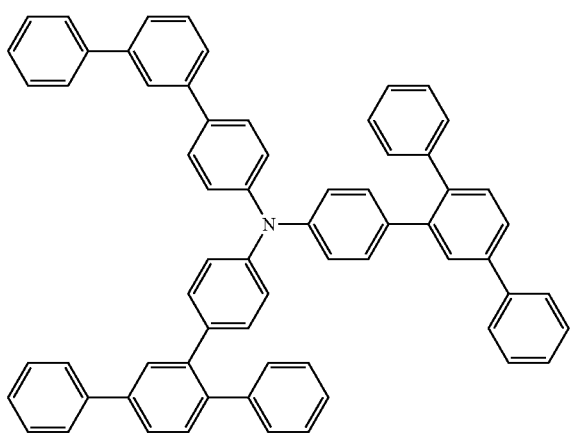
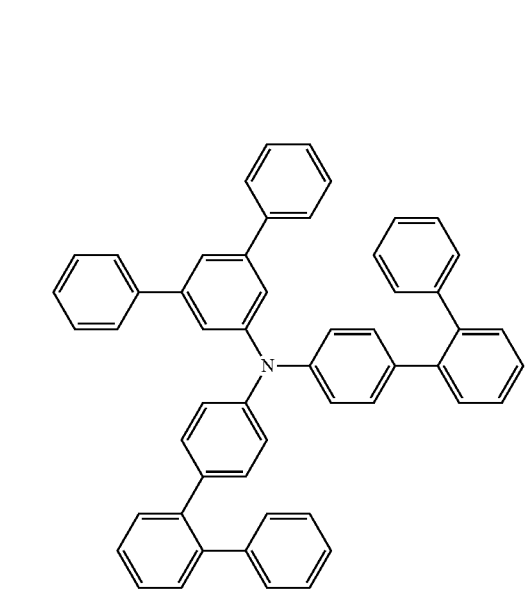
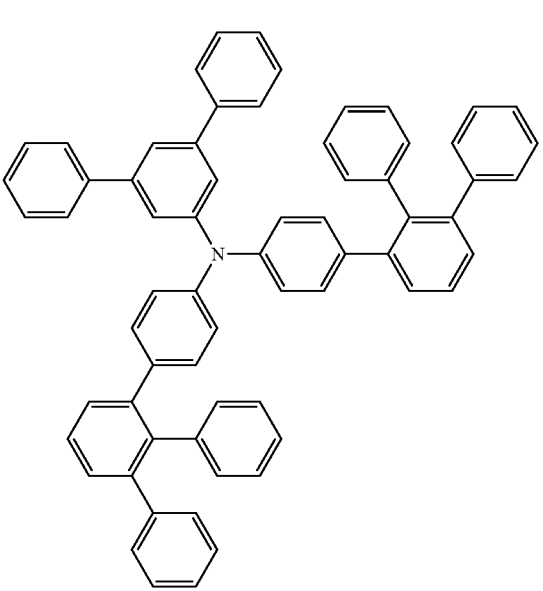

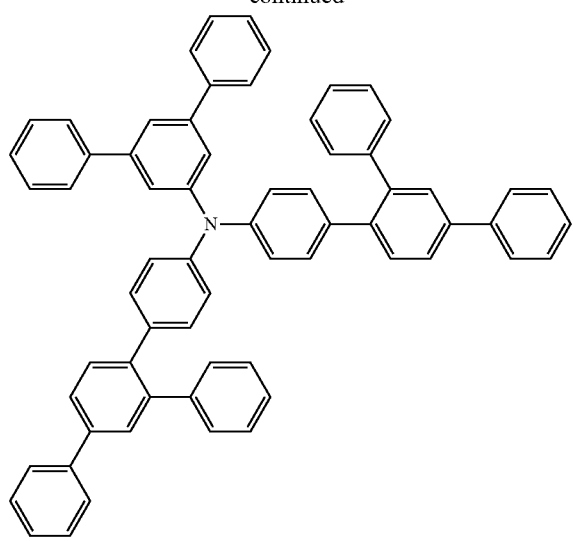
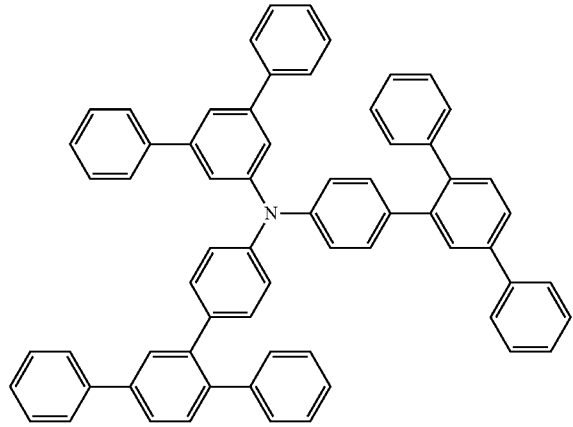
[Chemical Formula 26]
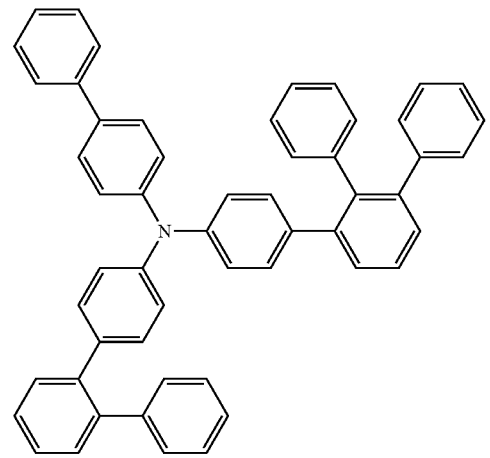
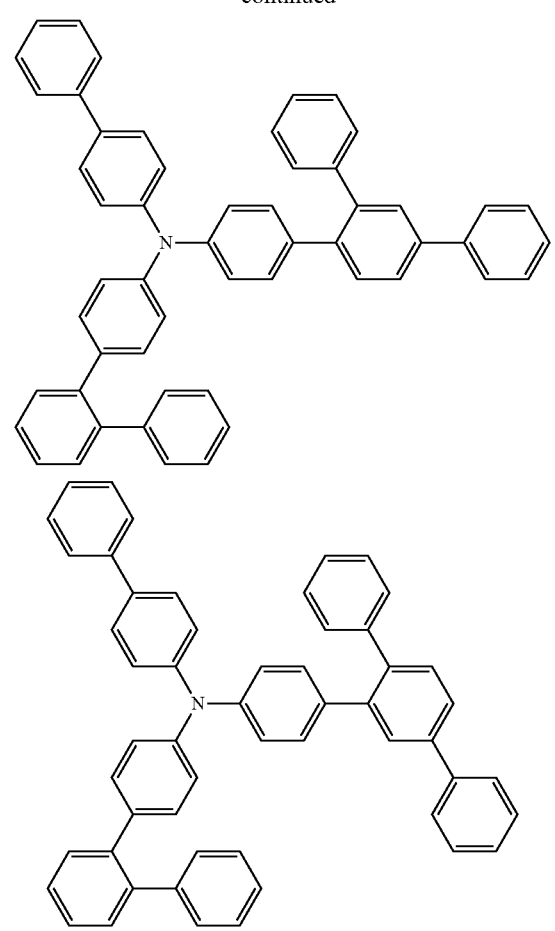
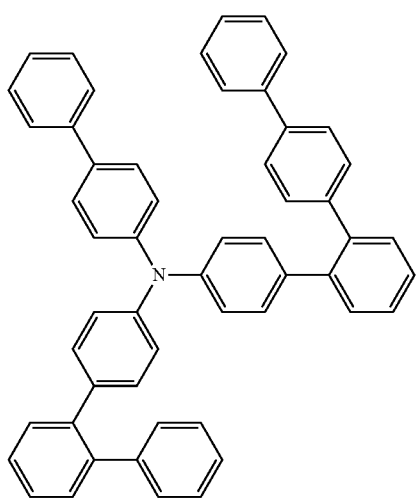

69
-continued
70
-continued
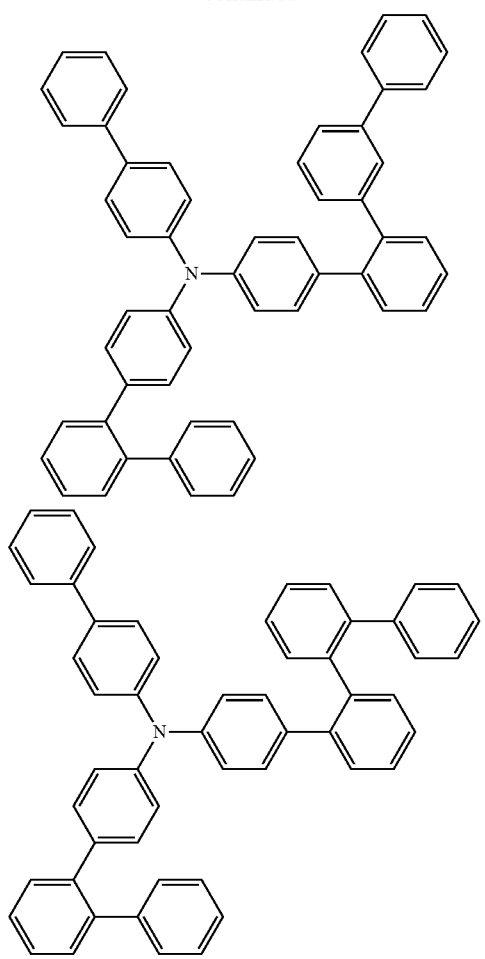
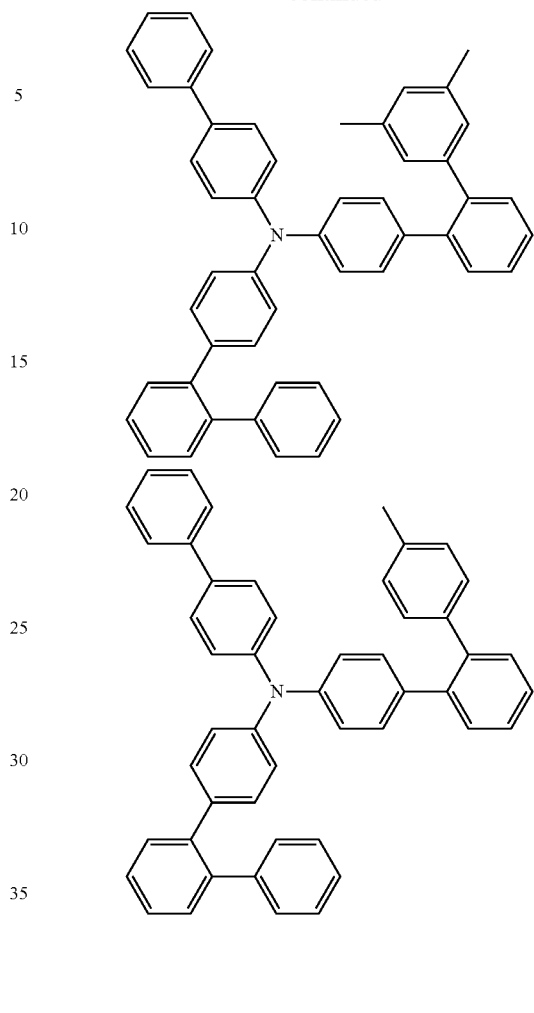
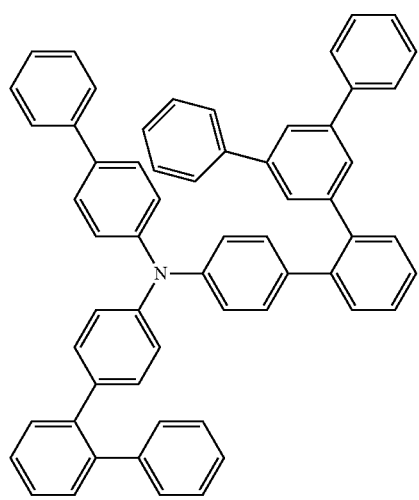
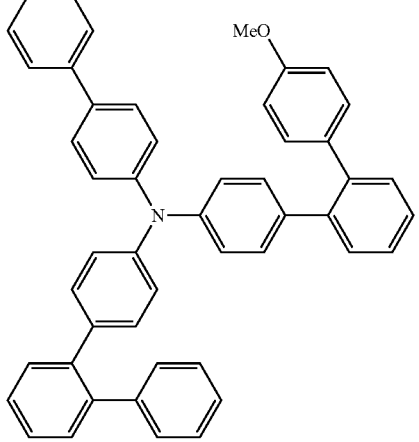

71
-continued
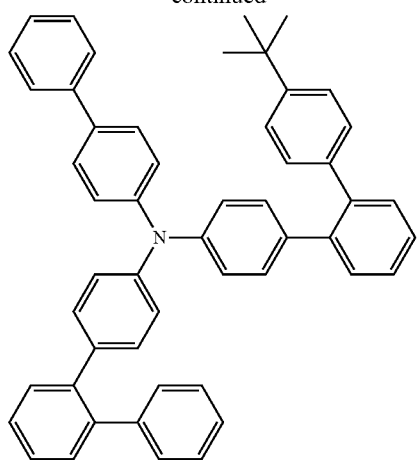
[Chemical Formula 27]
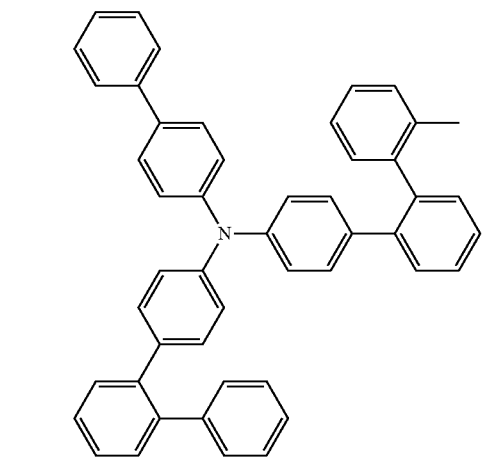
72
-continued
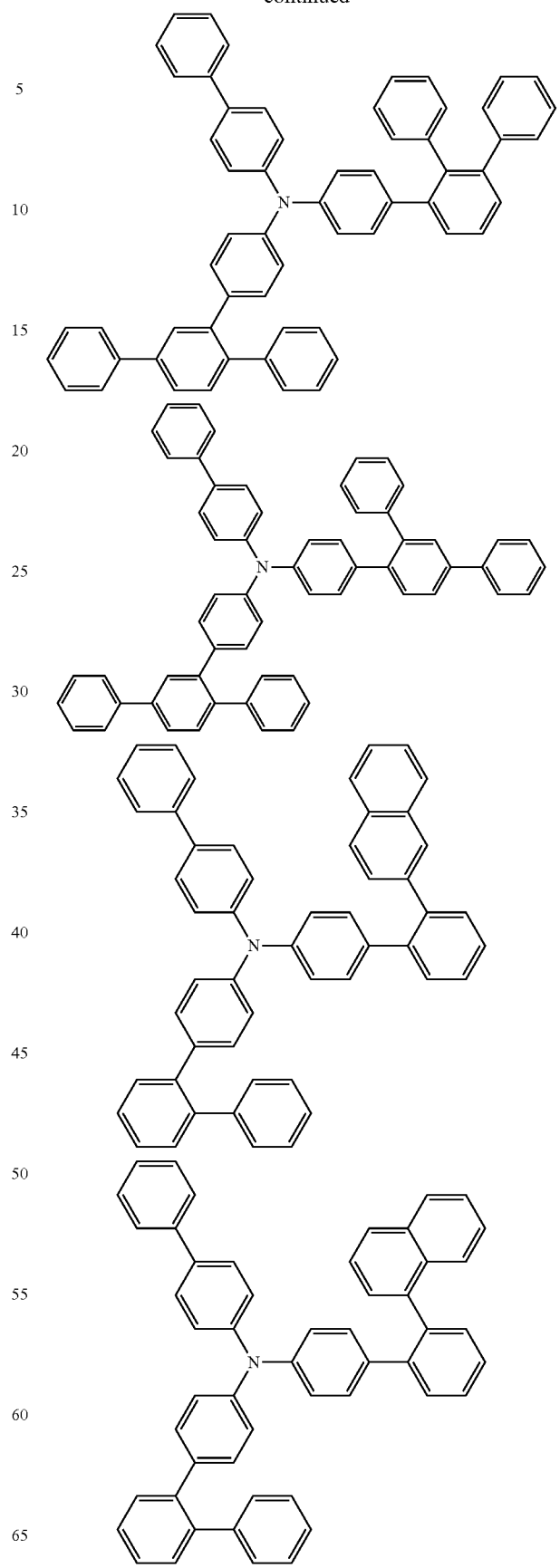
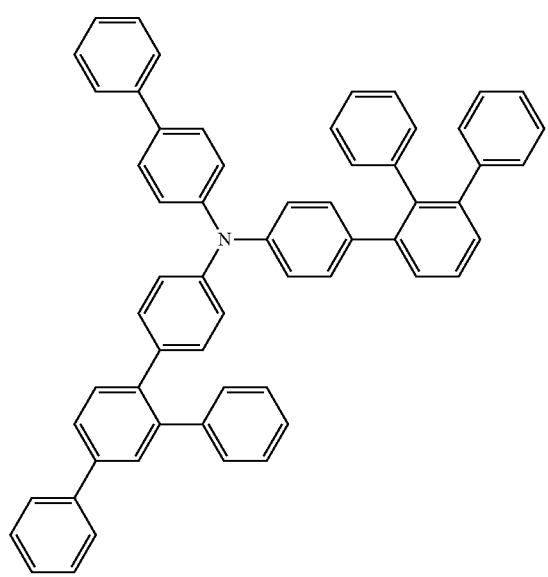

-continued
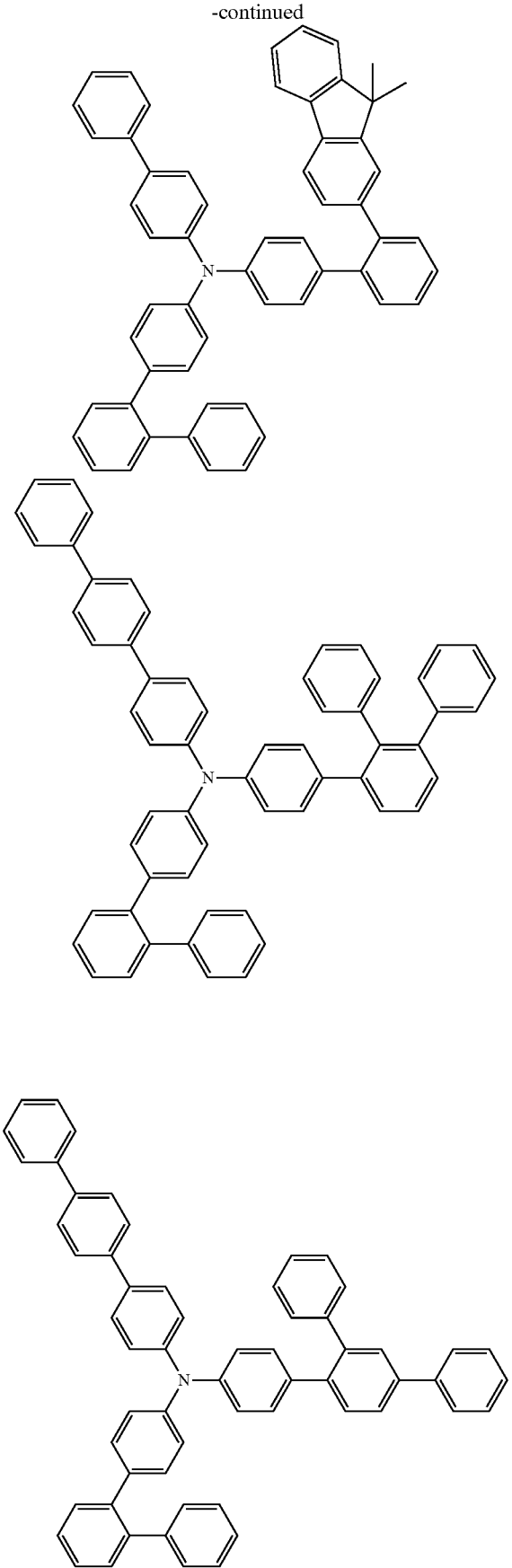
-continued
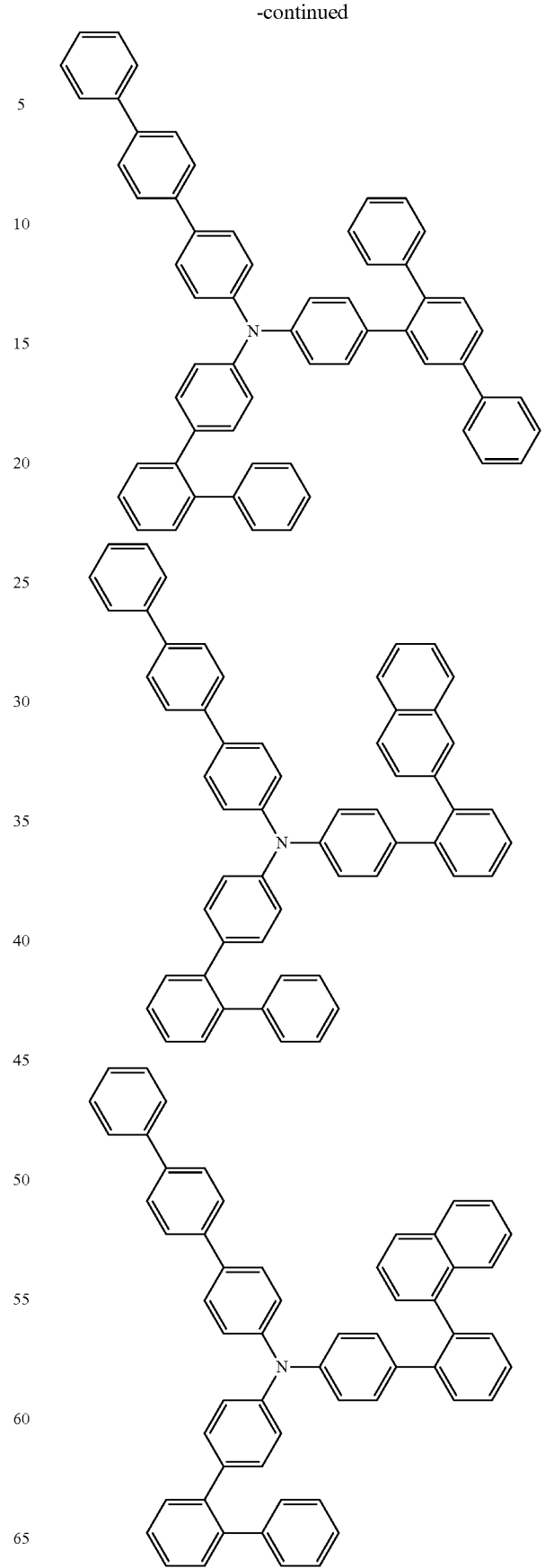

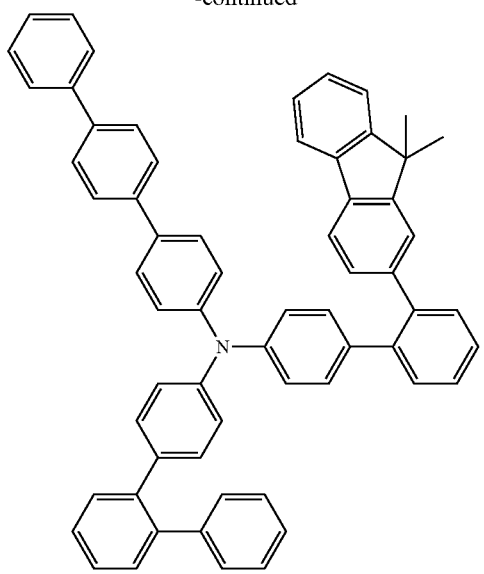
[Chemical Formula 28]
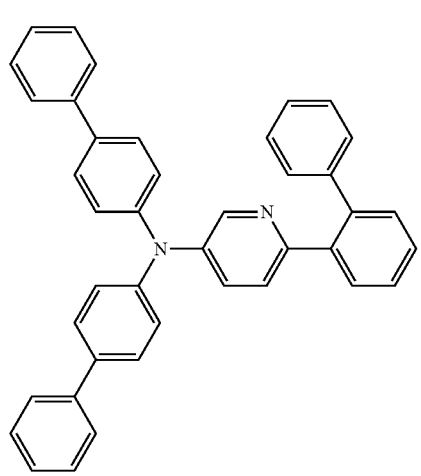
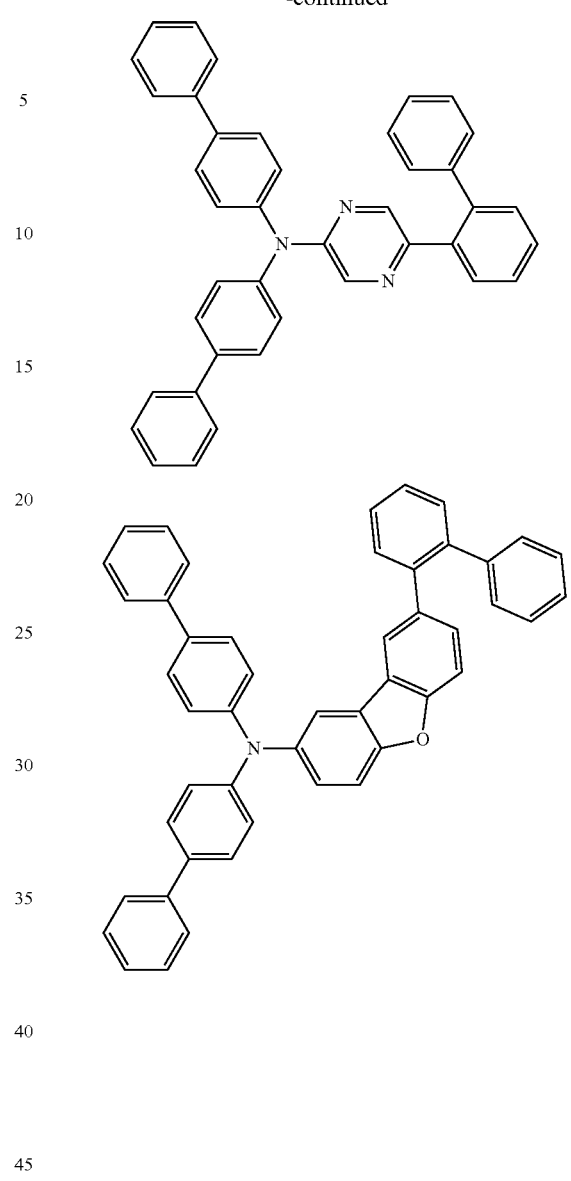

77
-continued
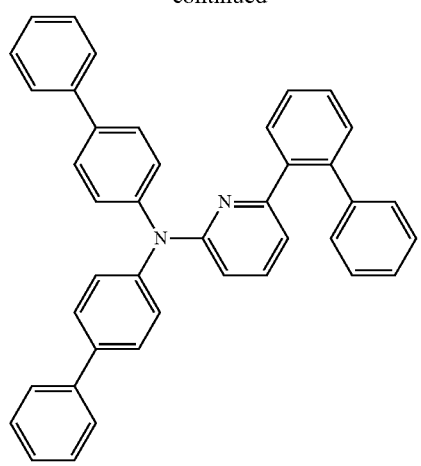
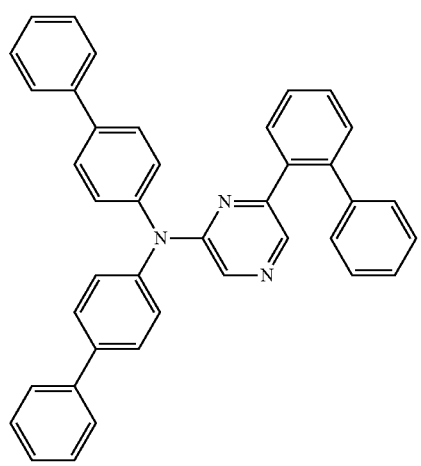
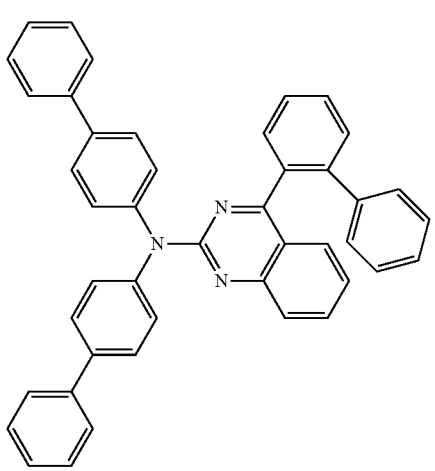
78
-continued
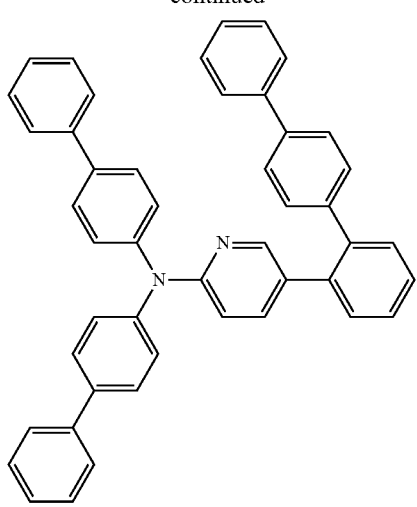
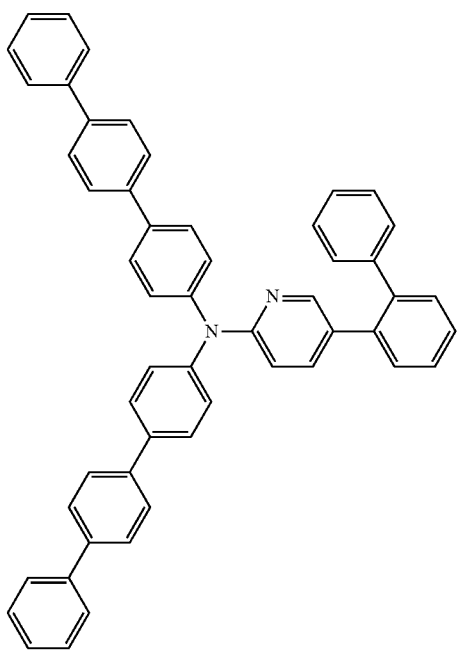

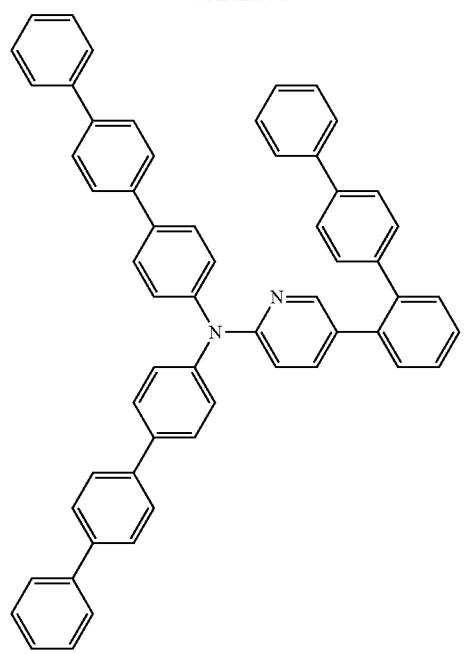
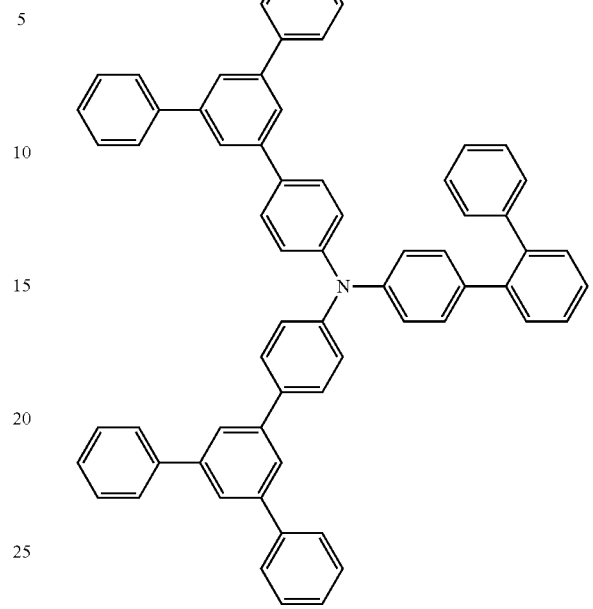
[Chemical Formula 29]
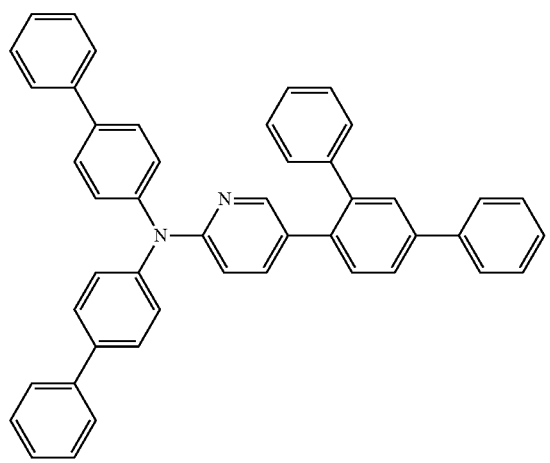
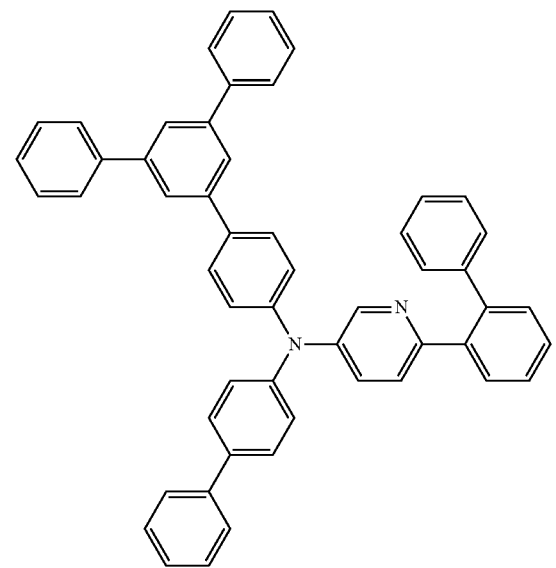

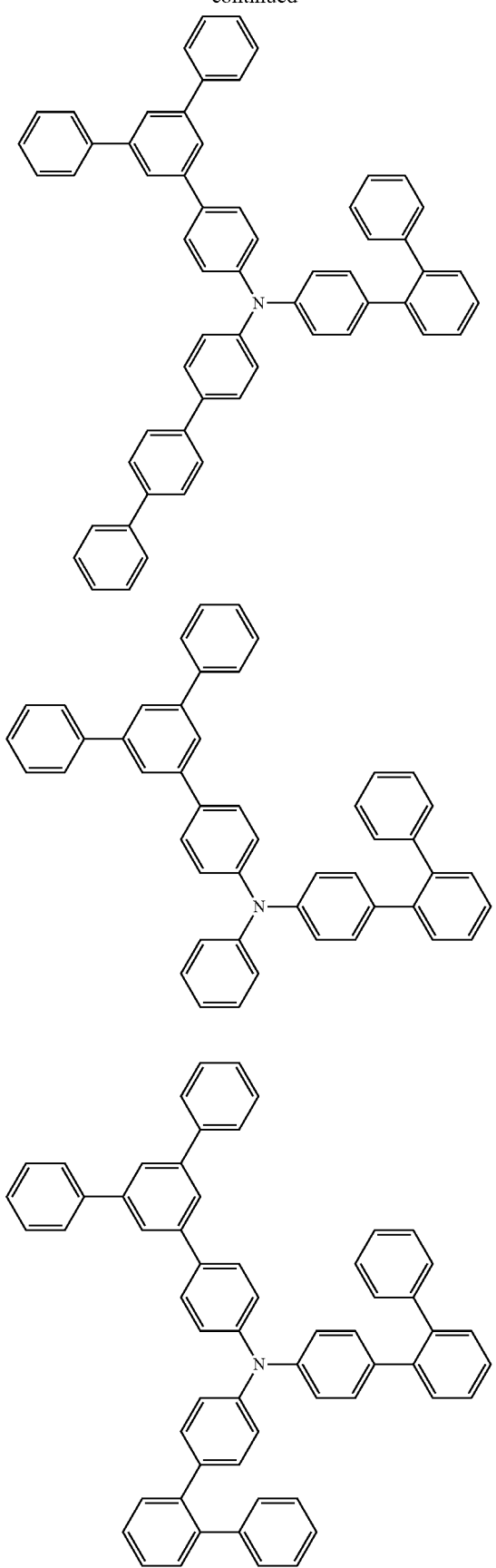
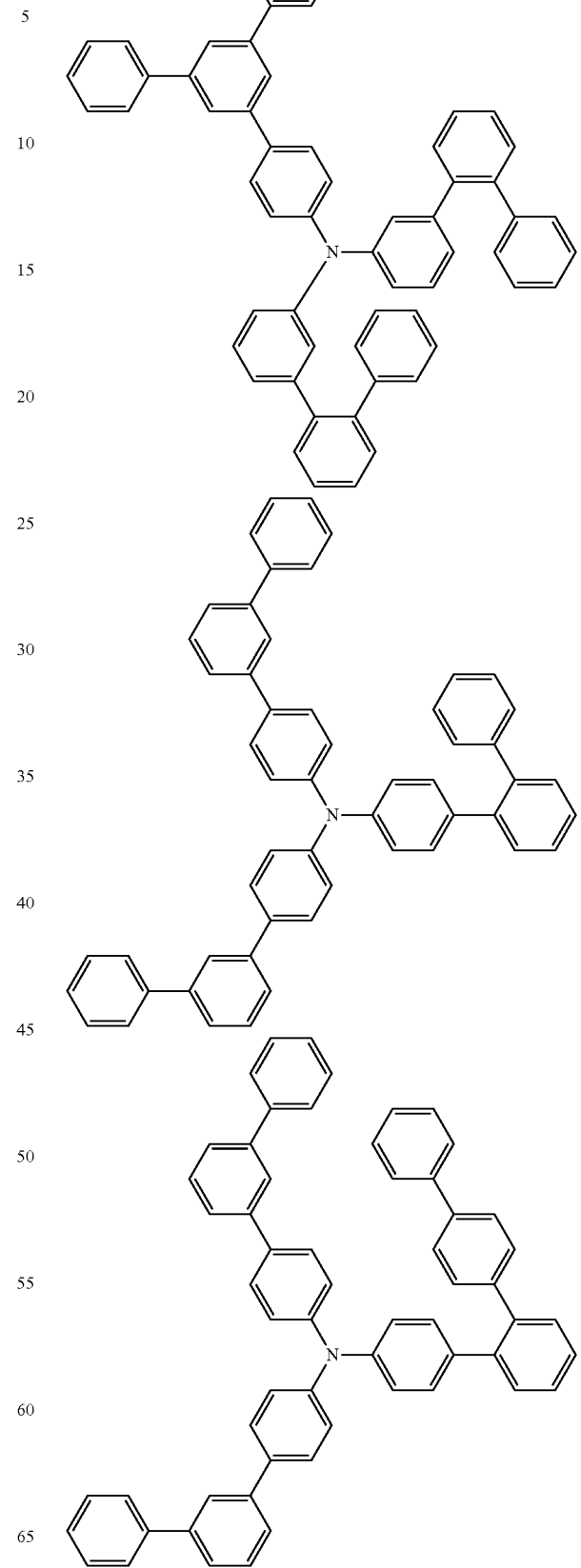

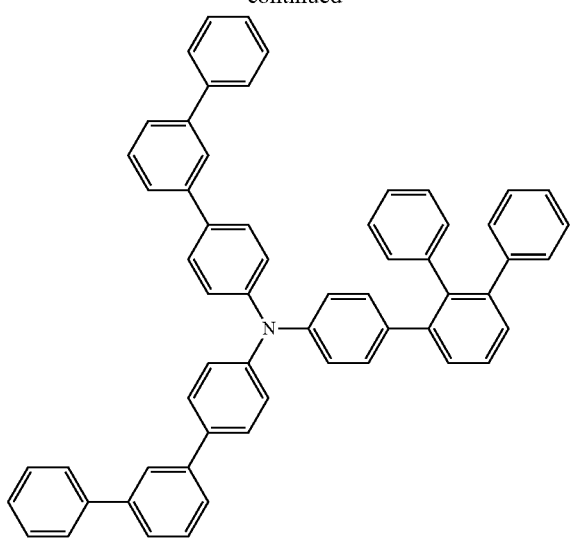
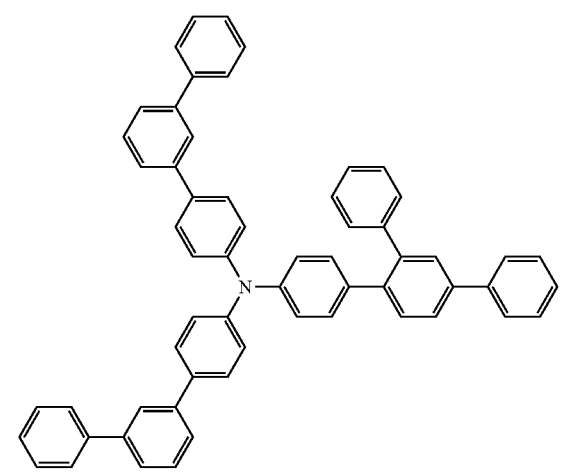
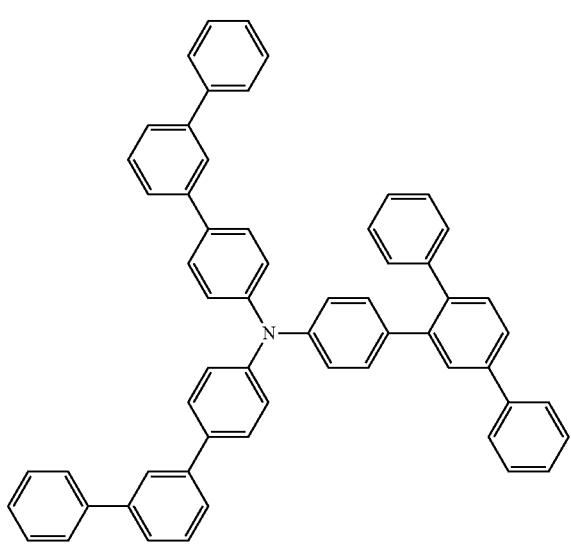

The compound having a monoamine skeleton as described above can be synthesized by a publicly known method. Examples of the synthesis method include a method based on a coupling reaction of a primary or secondary amine derivative with a halide or a triflate using palladium or a copper catalyst, and a coupling reaction of a halogenated amine derivative with an arylboronic acid derivative using palladium, but the method is not limited to these.

(Light-Emitting Element Material)

The compound represented by the general formula (1) is preferably used as a light-emitting element material. The "light-emitting element material" in the present invention refers to a material used in any layer of a light-emitting element. As described later, examples of the light-emitting element material include a material used in a protective film (capping layer) of an electrode in addition to a material used in a hole injection layer, a hole transport layer, a light-emitting layer, and/or an electron transport layer. Use of the compound represented by the general formula (1) in the present invention in any layer of a light-emitting element provides a light-emitting element having high luminous efficiency and excellent durable life.

(Light-Emitting Element) Then, the light-emitting element according to the present invention will be described in detail. An organic thin-film light-emitting element has a positive electrode, a negative electrode, and an organic layer interposed between the positive electrode and the negative electrode, and the organic layer emits light by electric energy.

In such a light-emitting element, examples of laminated structures interposed between the positive electrode and the negative electrode include, in addition to a structure composed only of a light-emitting layer, laminated structures such as 1) light-emitting layer/electron transport layer, 2) hole transport layer/light-emitting layer, 3) hole transport layer/light-emitting layer/electron transport layer, 4) hole injection layer/hole transport layer/light-emitting layer/electron transport layer, 5) hole transport layer/light-emitting layer/electron transport layer/electron injection layer, 6) hole injection layer/hole transport layer/light-emitting layer/electron transport layer/electron injection layer, and 7) hole injection layer/hole transport layer/light-emitting layer/hole blocking layer/electron transport layer/electron injection layer.

Furthermore, the light-emitting element may have a tandem structure in which a plurality of the above-mentioned laminated structures are stacked with an intermediate layer interposed therebetween. The intermediate layer is generally called an intermediate electrode, an intermediate conductive layer, a charge generation layer, an electron extraction layer, a connection layer, or an intermediate insulating layer, and can have a publicly known material constitution. Specific examples of the tandem structure include laminated structures including, as an intermediate layer, a charge generation layer between the positive electrode and the negative electrode, such as 8) hole transport layer/light-emitting layer/electron transport layer/charge generation layer/hole transport layer/light-emitting layer/electron transport layer, and 9) hole injection layer/hole transport layer/light-emitting layer/electron transport layer/electron injection layer/charge generation layer/hole injection layer/hole transport layer/light-emitting layer/electron transport layer/electron injection layer. Specific examples of a material preferably used to constitute the intermediate layer include pyridine derivatives and phenanthroline derivatives.

Each of the above-mentioned layers may be either a single layer or a plurality of layers, and may be doped. Further, each of the above-mentioned layers includes a positive electrode, at least one organic layer including a light-emitting layer, and a negative electrode. Moreover, it is also possible to mention an element constitution including a layer containing a capping material for improving the luminous efficiency due to an optical interference effect.

The light-emitting element according to the present invention includes a positive electrode, a negative electrode, and an organic layer present between the positive electrode and the negative electrode, emits light by electric energy, and contains the compound according to the present invention in at least one organic layer between the positive electrode and the negative electrode.

In the light-emitting element according to the present invention, it is preferable that, in the organic layer, at least a hole transport layer and a light-emitting layer be present, and that the hole transport layer contain the compound according to the present invention.

In the light-emitting element according to the present invention, the positive electrode and the negative electrode play a role of supplying a sufficient current for light emission of the element, and at least one of the positive electrode and the negative electrode is desirably transparent or translucent for extraction of light. Usually, the positive electrode formed on a substrate is a transparent electrode.

(Substrate)

It is preferable to form the light-emitting element on a substrate in order to maintain the mechanical strength of the light-emitting element. The substrate used is suitably a glass substrate made from soda glass or alkali-free glass. A thickness of a glass substrate of 0.5 mm or more is sufficient for maintaining the mechanical strength. As for the material of glass, alkali-free glass is more preferable because less elution of ions from the glass is preferable. In addition, soda lime glass with a barrier coat of $SiO_2$ or the like is commercially available, and such glass can also be used. Moreover, as long as a first electrode formed on a substrate functions stably, the substrate does not have to be made of glass, and may be a plastic substrate, for example.

(Positive Electrode)

The material used in the positive electrode is not particularly limited as long as the material can efficiently inject holes into the organic layer. For extraction of light, the material used in the positive electrode is preferably transparent or translucent. Specific examples of the material include conductive metal oxides such as zinc oxide, tin oxide, indium oxide, indium tin oxide (ITO), and indium zinc oxide (IZO), metals such as gold, silver, and chromium, inorganic conductive substances such as copper iodide and copper sulfide, and conductive polymers such as polythiophenes, polypyrroles, and polyanilines. Use of ITO glass or NESA glass is particularly desirable. These electrode materials may be used alone, or a laminate or a mixture of a plurality of materials may be used. The resistance of the transparent electrode is not limited as long as the electrode can supply a sufficient current for light emission of the element. However, from the viewpoint of power consumption of the element, it is desirable that the transparent electrode have low resistance. For example, an ITO substrate having a resistance of 300Ω/□ or less functions as an element electrode. However, use of a low-resistance substrate having a resistance of 20Ω/□ or less is particularly desirable since it is currently possible to supply a substrate having a resistance of about 10Ω/□. The thickness of ITO can be arbitrarily selected according to the resistance value, and is usually in the range of 45 to 300 nm.

(Negative Electrode)

The material used in the negative electrode is not particularly limited as long as the material is a substance that can efficiently inject electrons into the light-emitting layer. In general, metals such as platinum, gold, silver, copper, iron, tin, aluminum, and indium, and alloys and multilayer laminates of these metals with low work function metals such as lithium, sodium, potassium, calcium, and magnesium are preferable. Among them, aluminum, silver, or magnesium is preferable for a main component of the material from the viewpoint of electric resistance, ease of film formation, film stability, luminous efficiency, and the like. In particular, a negative electrode containing magnesium and silver is preferable because electron injection into the electron transport layer and the electron injection layer in the present invention is facilitated, and the element can be driven at a low voltage.

(Protective Film Layer)

In order to protect the negative electrode, a protective film layer (capping layer) is preferably stacked on the negative electrode. Although the material that constitutes the protective film layer is not particularly limited, examples of the material include metals such as platinum, gold, silver, copper, iron, tin, aluminum, and indium, alloys containing these metals, inorganic substances such as silica, titania, and silicon nitride, and organic polymer compounds such as polyvinyl alcohol, polyvinyl chloride, and hydrocarbon polymer compounds. Further, the compound represented by the general formula (1) can also be used in the protective film layer. However, in the case where the light-emitting element has an element structure in which light is extracted from the negative electrode side (such a structure is referred to as "top emission structure"), the material used in the protective film layer is selected from materials that transmit light in the visible light region.

(Hole Injection Layer)

The hole injection layer is a layer inserted between the positive electrode and the hole transport layer. The hole injection layer may be either a single layer or a laminate of a plurality of layers. Presence of the hole injection layer between the hole transport layer and the positive electrode is preferable because not only the element can be driven at a lower voltage and the durable life is easily improved, but also the carrier balance in the element is improved and the luminous efficiency is easily improved.

The material used in the hole injection layer is not particularly limited, and examples of the used material include benzidine derivatives such as 4,4'-bis(N-(3-methylphenyl)-N-phenylamino)biphenyl (TPD), 4,4'-bis(N-(1-naphthyl)-N-phenylamino)biphenyl (NPD), 4,4'-bis(N,N-bis(4-biphenylyl)amino)biphenyl (TBDB), and bis(N,N'-diphenyl-4-aminophenyl)-N,N-diphenyl-4,4'-diamino-1,1'-biphenyl (TPD232), a material group called starburst arylamines such as 4,4',4"-tris(3-methylphenyl(phenyl)amino)triphenylamine (m-MTDATA) and 4,4',4"-tris(1-naphthyl(phenyl)amino)triphenylamine (1-TNATA), biscarbazole derivatives such as bis(N-arylcarbazole) and bis(N-alkylcarbazole), heterocyclic compounds such as pyrazoline derivatives, stilbene compounds, hydrazone compounds, benzofuran derivatives, thiophene derivatives, oxadiazole derivatives, phthalocyanine derivatives, and porphyrin derivatives, and polymers having the above-mentioned monomers in a side chain, such as polycarbonates, styrene derivatives, polythiophenes, polyanilines, polyfluorenes, polyvinylcarbazoles, and polysilanes. Further, the compound represented by the general formula (1) (monoamine derivative) can also be used. Among them, the benzidine derivatives and the material group of starburst arylamines are more preferably used from the viewpoint that they have a shallower HOMO level than the compound represented by the general formula (1) does, and that they smoothly inject and transport holes from the positive electrode to the hole transport layer.

These materials may be used alone, or a mixture of two or more materials may be used. Alternatively, a plurality of materials may be stacked to form the hole injection layer. Further, it is more preferable that the hole injection layer be composed only of an acceptor compound or contain the hole injection material as described above doped with an acceptor compound, because the above-mentioned effects can be achieved more remarkably. An acceptor compound is a material that forms a charge transfer complex with a hole transport layer in contact with the acceptor compound when used as a single-layer film, and forms a charge transfer complex with a material that constitutes a hole injection layer when used as a dopant. Use of such a material improves the conductivity of the hole injection layer, further contributes to lowering of the driving voltage of the element, and easily provides the effects of improving the luminous efficiency and the durable life.

Examples of the acceptor compound include metal chlorides such as iron(III) chloride, aluminum chloride, gallium chloride, indium chloride, and antimony chloride, metal oxides such as molybdenum oxide, vanadium oxide, tungsten oxide, and ruthenium oxide, and charge transfer complexes such as tris(4-bromophenyl)aminium hexachloroantimonate (TBPAH). In addition, organic compounds having a nitro group, a cyano group, a halogen, or a trifluoromethyl group in the molecule, quinone compounds, acid anhydride compounds, fullerenes, and the like are also suitably used. Specific examples of these compounds include hexacyanobutadiene, hexacyanobenzene, tetracyanoethylene, tetracyanoquinodimethane (TCNQ), tetrafluorotetracyanoquinodimethane (F4-TCNQ), radialene derivatives, p-fluoranil, p-chloranil, p-bromanyl, p-benzoquinone, 2,6-dichlorobenzoquinone, 2,5-dichlorobenzoquinone, tetramethylbenzoquinone, 1,2,4,5-tetracyanobenzene, o-dicyanobenzene, p-dicyanobenzene, 1,4-dicyanotetrafluorobenzene, 2,3-dichloro-5,6-dicyanobenzoquinone, p-dinitrobenzene, m-dinitrobenzene, o-dinitrobenzene, p-cyanonitrobenzene, m-cyanonitrobenzene, o-cyanonitrobenzene, 1,4-naphthoquinone, 2,3-dichloronaphthoquinone, 1-nitronaphthalene, 2-nitronaphthalene, 1,3-dinitronaphthalene, 1,5-dinitronaphthalene, 9-cyanoanthracene, 9-nitroanthracene, 9,10-anthraquinone, 1,3,6,8-tetranitrocarbazole, 2,4,7-trinitro-9-fluorenone, 2,3,5,6-tetracyanopyridine, maleic anhydrides, phthalic anhydrides, C60, and C70.

Among them, metal oxides and cyano group-containing compounds are preferable because they are easy to handle and easy to deposit, so that they easily provide the above-mentioned effects. In both the case where the hole injection layer is composed only of an acceptor compound and the case where the hole injection layer is doped with an acceptor compound, the hole injection layer may be a single layer or a laminate of a plurality of layers.

(Hole Transport Layer)

The hole transport layer is a layer that transports holes injected from the positive electrode to the light-emitting layer. The hole transport layer may be either a single layer or a laminate of a plurality of layers.

The compound represented by the general formula (1) is preferably used in the hole injection layer and the hole transport layer of the light-emitting element, because the compound has an ionization potential (a measured value of a deposited film with AC-2 (RIKEN KEIKI CO., LTD.)) of 5.1 to 6.0 eV, high triplet energy level, good hole transport properties, and thin film stability. Moreover, since the compound represented by the general formula (1) is a monoamine derivative and has a large energy gap, the compound has a shallow LUMO level and excellent electron-blocking properties. Therefore, the compound can prevent entering of electrons flowing out of the light-emitting layer.

When the hole transport layer includes a plurality of layers, a hole transport layer containing the compound represented by the general formula (1) is preferably in direct contact with the light-emitting layer. This is because the compound represented by the general formula (1) has good electron-blocking properties, is hardly decomposed even in an excited state, and has an excellent durable life. Furthermore, since the compound represented by the general formula (1) has a high triplet level, the compound also has an effect of confining the excitation energy of a triplet light-emitting material. Therefore, even when the light-emitting layer contains a triplet light-emitting material, a hole transport layer containing the compound represented by the general formula (1) is preferably in direct contact with the light-emitting layer.

The hole transport layer may be composed only of the compound represented by the general formula (1), or other materials may be mixed in the hole transport layer as long as the effects of the present invention are not impaired. In this case, examples of such other materials used include benzidine derivatives such as 4,4'-bis(N-(3-methylphenyl)-N-phenylamino)biphenyl (TPD), 4,4'-bis(N-(1-naphthyl)-N-phenylamino)biphenyl (NPD), 4,4'-bis(N,N-bis(4-biphenylyl)amino)biphenyl (TBDB), and bis(N,N'-diphenyl-4-aminophenyl)-N,N-diphenyl-4,4'-diamino-1,1'-biphenyl (TPD232), a material group called starburst arylamines such as 4,4',4"-tris(3-methylphenyl(phenyl)amino)triphenylamine (m-MTDATA) and 4,4',4"-tris(1-naphthyl(phenyl)amino)triphenylamine (1-TNATA), biscarbazole derivatives such as bis(N-arylcarbazole) and bis(N-alkylcarbazole), heterocyclic compounds such as pyrazoline derivatives, stilbene compounds, hydrazone compounds, benzofuran derivatives, thiophene derivatives, oxadiazole derivatives, phthalocyanine derivatives, and porphyrin derivatives, and polymers having the above-mentioned monomers in a side chain, such as polycarbonates, styrene derivatives, polythiophenes, polyanilines, polyfluorenes, polyvinylcarbazoles, and polysilanes.

(Light-Emitting Layer)

The light-emitting layer may be either a single layer or a plurality of layers, and is each formed from a light-emitting material (a host material and/or a dopant material). Each light-emitting layer may be any of a mixture of a host material and a dopant material, a host material alone, or a mixture of two host materials and one dopant material. That is, in each light-emitting layer of the light-emitting element according to the present invention, only the host material or the dopant material may emit light, or both the host material and the dopant material may emit light. From the viewpoint of efficiently utilizing electric energy and achieving light emission with high color purity, the light-emitting layer is preferably formed from a mixture of the host material and the dopant material. Further, each of the host material and the dopant material may be either one material or a combination of a plurality of materials. The dopant material may be either contained in the entire host material or in part of the host material. The dopant material may be either stacked or dispersed. The dopant material can control the emission color. The amount of the dopant material used is preferably 30 wt % or less, more preferably 20 wt % or less based on the host material because too large an amount of the dopant material may cause a concentration quenching phenomenon. As for the doping method, the light-emitting layer can be formed by a co-evaporation method of the dopant material with the host material, but the dopant material may be previously mixed with the host material and simultaneously deposited with the host material.

Examples of usable light-emitting materials include, in addition to the compound represented by the general formula (1), fused ring derivatives such as anthracene and pyrene, which have been previously known as light emitters, metal chelated oxinoid compounds such as tris(8-quinolinolato)aluminum, bis-styryl derivatives such as bisstyrylanthracene derivatives and distyrylbenzene derivatives, tetraphenylbutadiene derivatives, indene derivatives, coumarin derivatives, oxadiazole derivatives, pyrrolopyridine derivatives, perinone derivatives, cyclopentadiene derivatives, oxadiazole derivatives, thiadiazolopyridine derivatives, dibenzofuran derivatives, carbazole derivatives, indolocarbazole derivatives, and polymers such as polyphenylenevinylene derivatives, polyparaphenylene derivatives, and polythiophene derivatives, but are not particularly limited thereto.

The host material contained in the light-emitting material does not have to be limited to a single compound, and it is possible to use a mixture of a plurality of the compounds according to the present invention, or a mixture with at least one other host material. Further, a laminate of host materials may also be used. The host material is not particularly limited, and examples of usable host materials include compounds having a fused aryl ring and derivatives thereof, such as naphthalene, anthracene, phenanthrene, pyrene, chrysene, naphthacene, triphenylene, perylene, fluoranthene, fluorene, and indene, aromatic amine derivatives such as N,N'-dinaphthyl-N,N'-diphenyl-4,4'-diphenyl-1,1'-diamine, metal chelated oxinoid compounds such as tris(8-quinolinolato)aluminum(III), bis-styryl derivatives such as distyrylbenzene derivatives, tetraphenylbutadiene derivatives, indene derivatives, coumarin derivatives, oxadiazole derivatives, pyrrolopyridine derivatives, perinone derivatives, cyclopentadiene derivatives, pyrrolopyrrole derivatives, thiadiazolopyridine derivatives, dibenzofuran derivatives, carbazole derivatives, indolocarbazole derivatives, triazine derivatives, and polymers such as polyphenylenevinylene derivatives, polyparaphenylene derivatives, polyfluorene derivatives, polyvinylcarbazole derivatives, and polythiophene derivatives. Among them, metal chelated oxinoid compounds, dibenzofuran derivatives, dibenzothiophene derivatives, carbazole derivatives, indolocarbazole derivatives, triazine derivatives, triphenylene derivatives and the like are suitably used as the host when the light-emitting layer performs triplet emission (phosphorescence emission).

Conventionally, a light-emitting layer containing an anthracene compound as a host is widely used as a blue light-emitting layer. In the present invention, an "anthracene compound" means a compound having an anthracene skeleton. A host containing an anthracene compound has a shallower LUMO level, that is, a shallower electron conduction level than that of a host material used in a red or green light-emitting layer, and easily leaks electrons into an adjacent hole transport layer. Therefore, a blue light-emitting element containing an anthracene compound as a host material has an insufficient durable life compared to a red light-emitting element and a green light-emitting element. However, since the compound represented by the general formula (1) has excellent electron-blocking properties and is hardly decomposed even in an excited state, when the compound is used in a hole transport layer of a light-emitting element having a light-emitting layer containing an anthracene compound as a host, the durable life is easily greatly improved. Therefore, in the light-emitting element according to the present invention, the light-emitting layer preferably contains an anthracene compound.

The dopant material contained in the light-emitting material is not particularly limited, and examples thereof include compounds having an aryl ring, such as naphthalene, anthracene, phenanthrene, pyrene, fluoranthene, triphenylene, perylene, fluorene, and indene, and derivatives thereof (for example, 2-(benzothiazole-2-yl)-9,10-diphenylanthracene and 5,6,11,12-tetraphenylnaphthacene), compounds having a heteroaryl ring and derivatives thereof, such as furan, pyrrole, thiophene, silole, 9-silafluorene, 9,9'-spirobisilafluorene, benzothiophene, benzofuran, indole, dibenzothiophene, dibenzofuran, imidazopyridine, phenanthroline, pyrazine, naphthyridine, quinoxaline, pyrrolopyridine, and thioxanthene, aminostyryl derivatives such as distyrylbenzene derivatives, 4,4'-bis(2-(4-diphenylaminophenyl) ethenyl)biphenyl, and 4,4'-bis(N-(stilben-4-yl)-N-phenylamino)stilbene, aromatic acetylene derivatives, tetraphenylbutadiene derivatives, stilbene derivatives, aldazine derivatives, pyrromethene derivatives, diketopyrrolo[3,4-c]pyrrole derivatives, coumarin derivatives such as 2,3,5,6-1H,4H-tetrahydro-9-(2'-benzothiazolyl)quinolidino[9,9a,1-gh]coumarin, azole derivatives and metal complexes thereof, such as imidazole, triazole, thiadiazole, carbazole, oxazole, oxadiazole, and triazole, and aromatic amine derivatives represented by N,N'-diphenyl-N,N'-di(3-methylphenyl)-4,4'-diphenyl-1,1'-diamine. Among them, use of a dopant containing a diamine skeleton or a dopant containing a fluoranthene skeleton is preferable because high luminous efficiency can be easily obtained. A dopant containing a diamine skeleton has good hole trapping properties, and a dopant containing a fluoranthene skeleton has good electron trapping properties.

The triplet light-emitting material (phosphorescent dopant) used when the light-emitting layer performs triplet emission (phosphorescence emission) is preferably a metal complex compound containing at least one metal selected from the group consisting of iridium (Ir), ruthenium (Ru), palladium (Pd), platinum (Pt), osmium (Os), and rhenium (Re). The ligand preferably has a nitrogen-containing aromatic heterocyclic ring such as a phenylpyridine skeleton, a phenylquinoline skeleton, or a carbene skeleton. However, the complex is not limited to these, and an appropriate complex is selected in view of the required emission color, element performance, and the relationship with the host compound. Specific examples of the complex include a tris(2-phenylpyridyl)iridium complex, a tris{2-(2-thiophenyl)pyridyl}iridium complex, a tris{2-(2-benzothiophenyl)pyridyl}iridium complex, a tris(2-phenylbenzothiazole) iridium complex, a tris(2-phenylbenzoxazole) iridium complex, a trisbenzoquinoline iridium complex, a bis(2-phenylpyridyl) (acetylacetonato)iridium complex, a bis{2-(2-thiophenyl)pyridyl}iridium complex, a bis{2-(2-benzothiophenyl)pyridyl}(acetylacetonato)iridium complex, a bis(2-phenylbenzothiazole) (acetylacetonato)iridium complex, a bis(2-phenylbenzoxazole) (acetylacetonato)iridium complex, a bisbenzoquinoline(acetylacetonato) iridium complex, a bis{2-(2,4-difluorophenyl)pyridyl} (acetylacetonato)iridium complex, a tetraethylporphyrin platinum complex, a {tris(thenoyltrifluoroacetone)mono(1, 10-phenanthroline)}europium complex, a {tris(thenoyltrifluoroacetone)mono(4,7-diphenyl-1,10-phenanthroline)}europium complex, a {tris(1,3-diphenyl-1,3-propanedione) mono(1,10-phenanthroline)}europium complex, and a trisacetylacetone terbium complex. Moreover, the phosphorescent dopant described in Japanese Patent Laid-open Publication No. 2009-130141 can also be suitably used. Although the complex is not limited to these, an iridium complex or a platinum complex is preferably used because high luminous efficiency can be easily obtained.

As for the triplet light-emitting material used as a dopant material, each light-emitting layer may contain only one triplet light-emitting material or a mixture of two or more triplet light-emitting materials. When two or more triplet light-emitting materials are used, the total weight of the dopant material is preferably 30 wt % or less, more preferably 20 wt % or less based on the host material.

In addition to the host material and the triplet light-emitting material, the light-emitting layer may further contain a third component for adjusting the carrier balance in the light-emitting layer or stabilizing the layer structure of the light-emitting layer. Herein, the third component selected is a material that does not cause any interaction with the host material containing the compound represented by the general formula (1) that is a monoamine derivative or with the dopant material containing the triplet light-emitting material.

A preferable host and a preferable dopant in the triplet emission system are not particularly limited, and specific examples include the following.

[Chemical Formula 30]

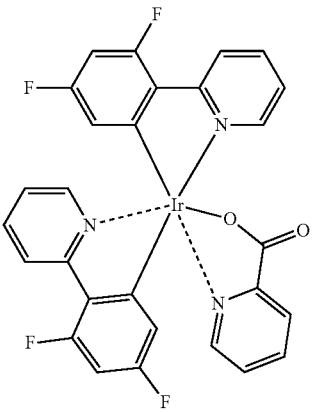

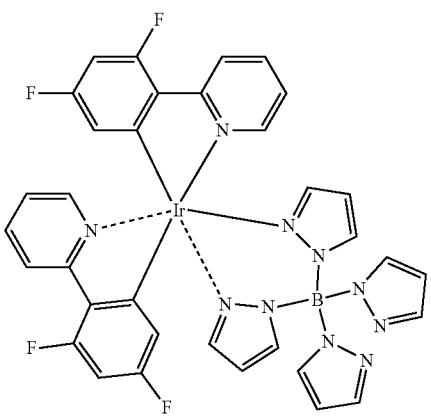

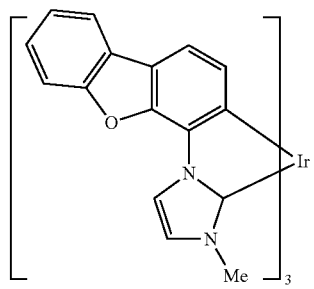

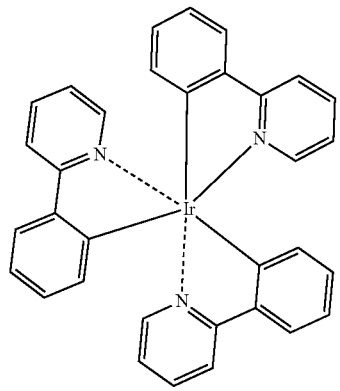

93
-continued
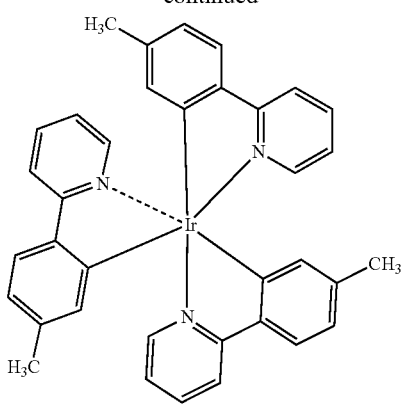
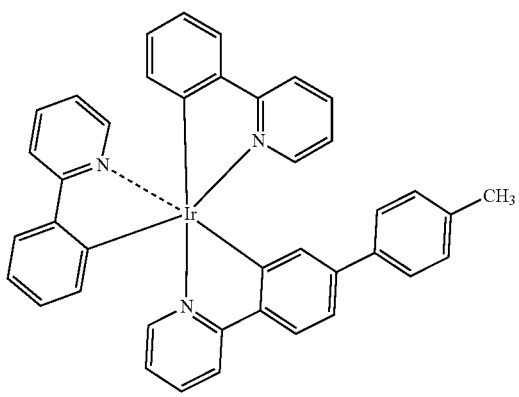
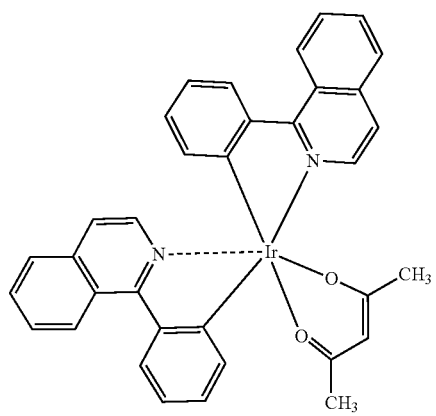
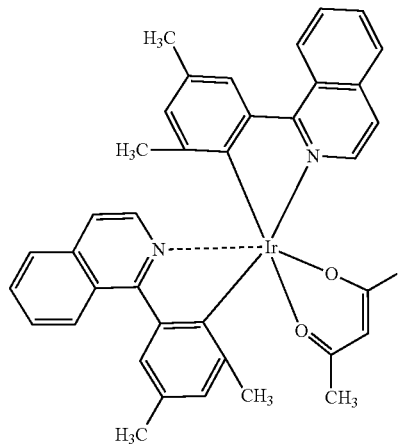
94
-continued
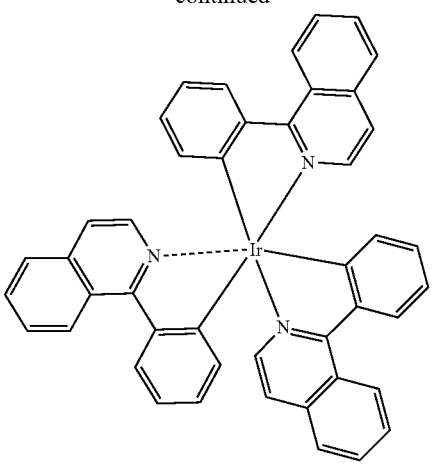
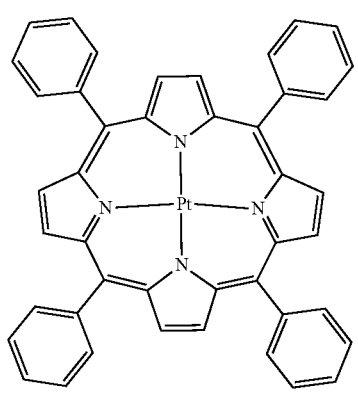
[Chemical Formula 31]
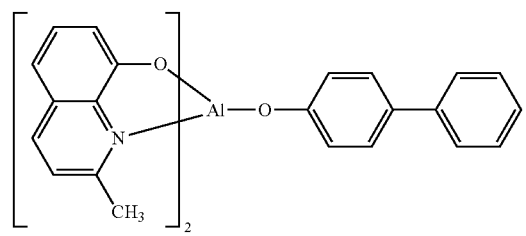
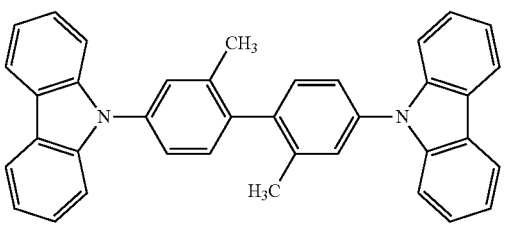
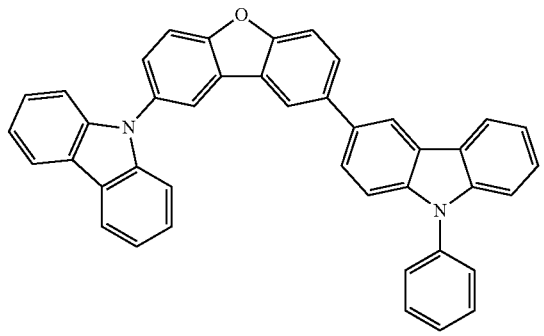

-continued
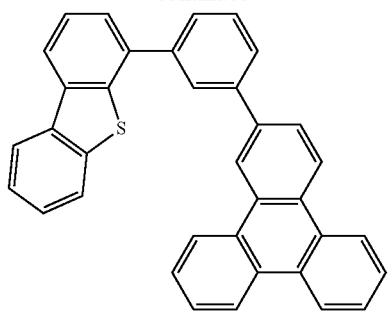
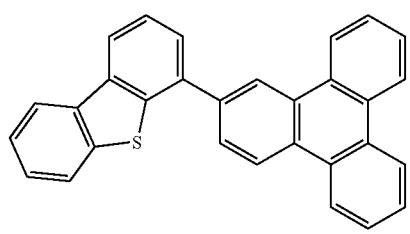
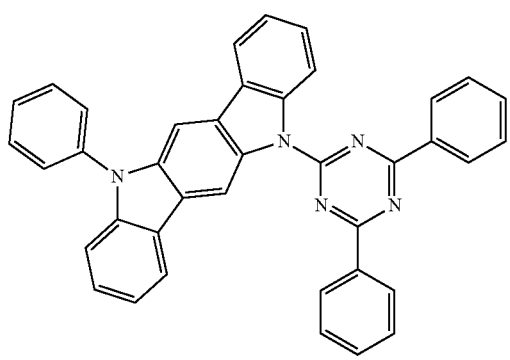
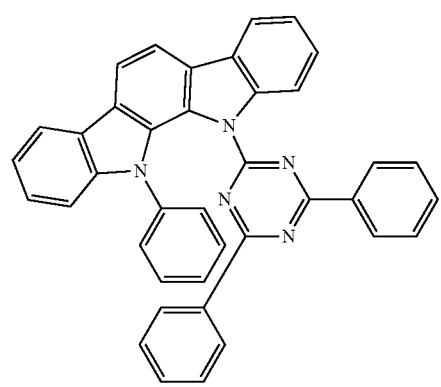
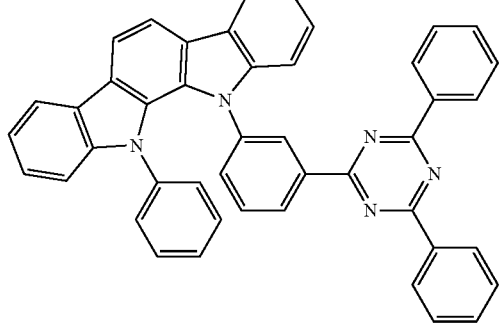
-continued
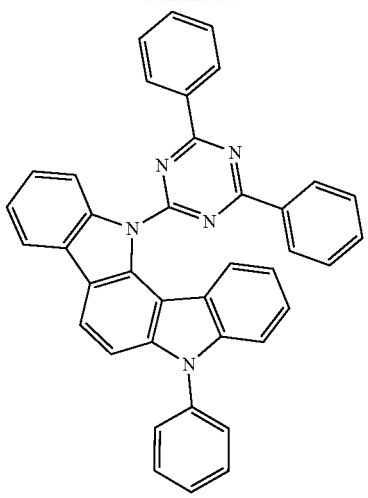
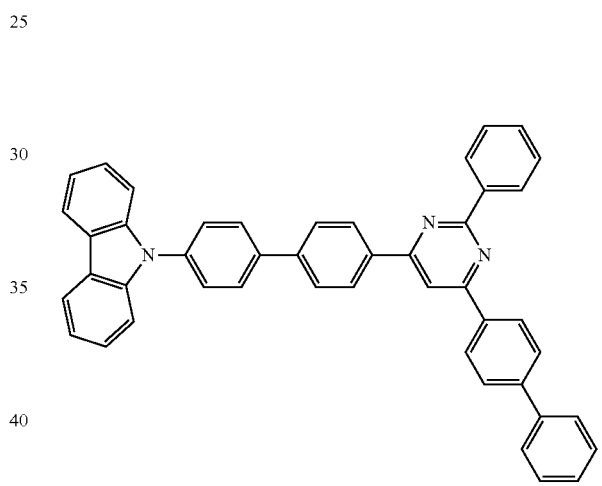
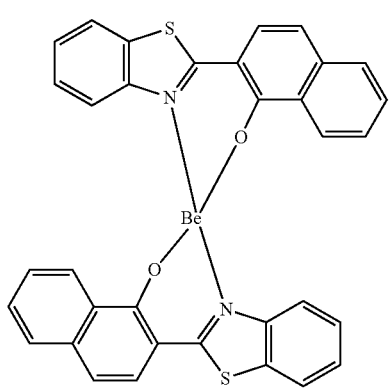

-continued

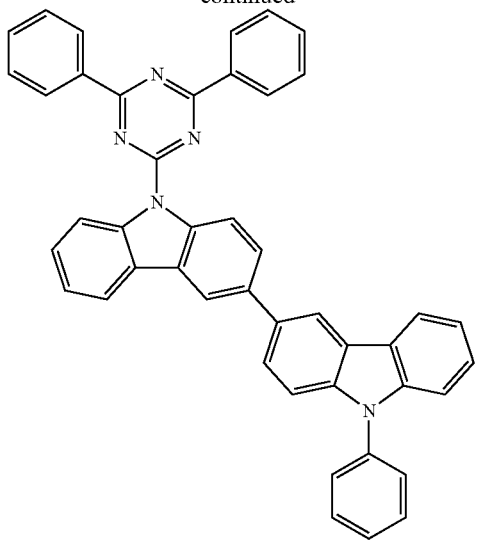

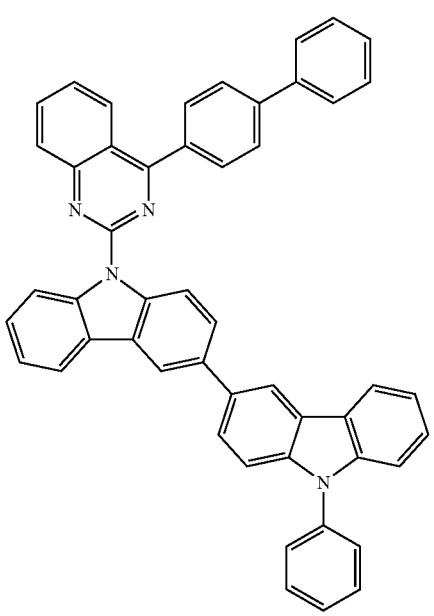

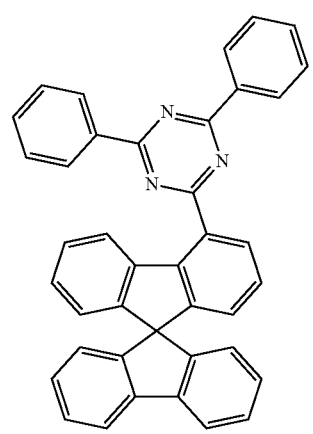

-continued

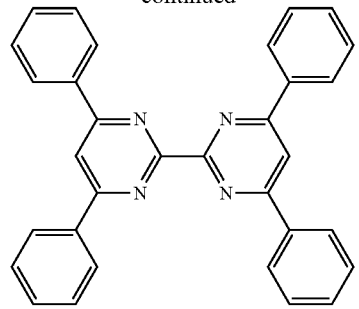

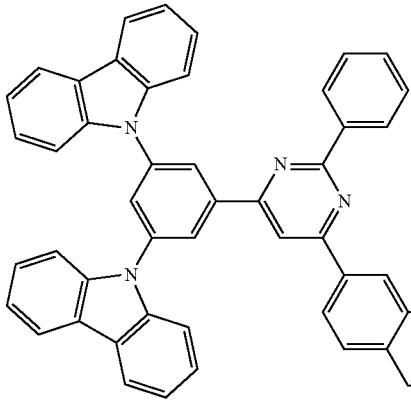

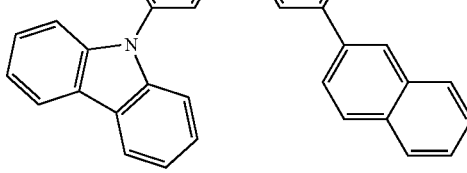

In the light-emitting element according to the present invention, it is preferable that the light-emitting layer contain a triplet light-emitting material. Owing to good electron-blocking properties and a high triplet level, the compound represented by the general formula (1) can easily achieve high luminous efficiency even when combined with a light-emitting layer containing a triplet light-emitting material. Further, for the host material of the above-mentioned light-emitting layer containing the triplet light-emitting material, a material having good electron transport properties, such as triazine or quinazoline is often used. In general, when these materials are used as a host, electrons easily leak from the light-emitting layer to the hole transport layer, and the light-emitting element has shorter durable life. Meanwhile, since the compound represented by the general formula (1) is hardly decomposed even in an excited state, use of the compound in the hole transport layer adjacent to the light-emitting layer can achieve longer life. Therefore, in the light-emitting element including the above-mentioned light-emitting layer containing the triplet light-emitting material, it is also preferable that the compound represented by the general formula (1) be used in the hole transport layer adjacent to the light-emitting layer.

It is also preferable that the light-emitting layer contain a thermally activated delayed fluorescent material. Thermally activated delayed fluorescence is described on pages 87 to 103 of "State-of the Art Organic Light-Emitting Diodes" (edited by Chihaya Adachi and Hiroshi Fujimoto, published by CMC Publishing Co., Ltd.). In the document, it is described that bringing the energy levels of an excited singlet state and an excited triplet state of a fluorescent light-emitting material close to each other causes, with high efficiency, reverse energy transfer from the excited triplet state to the excited singlet state that usually has a low transition probability, leading to Thermally Activated Delayed Fluorescence (TADF). Further, FIG. 5 in the document illustrates a mechanism of generation of delayed fluorescence. The delayed fluorescence emission can be confirmed by transient PL (Photo Luminescence) measurement. In general, thermally activated delayed fluorescent materials are also referred to as TADF materials. Owing to good electron-blocking properties and a high triplet level, the compound represented by the general formula (1) can easily achieve high luminous efficiency even when combined with a light-emitting layer containing a TADF material.

The thermally activated delayed fluorescent material may be a single material that exhibits thermally activated delayed fluorescence or a plurality of materials that together exhibit thermally activated delayed fluorescence. When the thermally activated delayed fluorescent material is a plurality of materials, the materials may be used as a mixture or as a laminate of layers each made from one of the materials. The thermally activated delayed fluorescent material used can be a publicly known material. Specific examples of the material include benzonitrile derivatives, triazine derivatives, disulfoxide derivatives, carbazole derivatives, indolocarbazole derivatives, dihydrophenazine derivatives, thiazole derivatives, and oxadiazole derivatives, but are not particularly limited thereto.

In an element in which the light-emitting layer contains the TADF material, it is preferable that the light-emitting layer further contain a fluorescent dopant. This is because the TADF material converts triplet excitons into singlet excitons, and the fluorescent dopant receives the singlet excitons, whereby high luminous efficiency and a long element life can be easily achieved. A compound represented by a general formula (5) is preferably used as the fluorescent dopant because the compound exhibits high fluorescence quantum yield and has a small Stokes shift and a small peak half-value width of an emission spectrum.

[Chemical Formula 32]

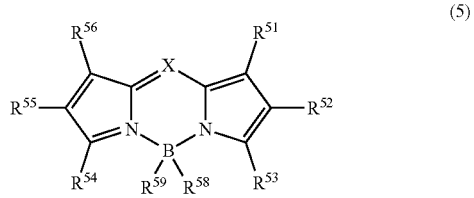

(5)

In the general formula (5), X represents C—$R^{57}$ or N. $R^{51}$ to $R^{59}$ may be identical or different, and are each selected from a hydrogen atom, an alkyl group, a cycloalkyl group, a heterocyclic group, an alkenyl group, a cycloalkenyl group, an alkynyl group, a hydroxyl group, a thiol group, an alkoxy group, an alkylthio group, an aryl ether group, an aryl thioether group, an aryl group, a heteroaryl group, a halogen, a cyano group, an aldehyde group, a carbonyl group, a carboxyl group, an ester group, a carbamoyl group, an amino group, a nitro group, a silyl group, a siloxanyl group, a boryl group, —P(=O)$R^{60}R^{61}$, and a fused ring and an aliphatic ring formed between the group and an adjacent substituent. $R^{60}$ and $R^{61}$ are each an aryl group or a heteroaryl group.

(Electron Transport Layer)

In the present invention, the electron transport layer is a layer in which electrons are injected from the negative electrode, and which further transports electrons. The electron transport layer is desired to have high electron injection efficiency and to efficiently transport the injected electrons. Therefore, the electron transport layer is required to be made from a substance that has high electron affinity, high electron mobility, and excellent stability, and that is unlikely to generate impurities serving as a trap during manufacture and use. In particular, in the case where a thick film of the electron transport layer is stacked, a compound having a molecular weight of 400 or more that maintains a stable film quality is preferable because a low-molecular weight compound is easily crystallized to deteriorate the film quality. However, in consideration of the transport balance between holes and electrons, if the electron transport layer mainly plays a role of efficiently preventing holes from the positive electrode from flowing to the negative electrode side instead of being recombined with electrons, an electron transport layer made from a material that does not have so high an electron transport capability has an effect of easily improving the luminous efficiency equivalent to that of an electron transport layer made from a material that has a high electron transport capability. Therefore, the electron transport layer in the present invention encompasses a hole blocking layer that can efficiently block the movement of holes as a layer having the same meaning, and the hole blocking layer and the electron transport layer may each be a single layer or a laminate of a plurality of materials.

Examples of the electron transport material used in the electron transport layer include fused polycyclic aromatic derivatives such as naphthalene and anthracene, styryl aromatic ring derivatives represented by 4,4'-bis(diphenylethenyl)biphenyl, quinone derivatives such as anthraquinone and diphenoquinone, phosphorus oxide derivatives, quinolinol complexes such as tris(8-quinolinolato)aluminum(III), benzoquinolinol complexes, hydroxyazole complexes, azomethine complexes, and various metal complexes such as tropolone metal complexes and flavonol metal complexes. The electron transport material used is preferably a compound having a heteroaryl ring structure that contains an element selected from carbon, hydrogen, nitrogen, oxygen, silicon, and phosphorus, and contains electron-accepting nitrogen because the driving voltage is lowered and high luminous efficiency is easily obtained.

Herein, the "electron-accepting nitrogen" means a nitrogen atom that forms a multiple bond with an adjacent atom. Since the nitrogen atom has high electronegativity, the multiple bond has electron-accepting properties. Therefore, an aromatic heterocyclic ring containing electron-accepting nitrogen has high electron affinity. An electron transport material having electron-accepting nitrogen makes it easier to receive electrons from a negative electrode having high electron affinity, and enables lower voltage driving of the element. In addition, since the supply of electrons to the light-emitting layer increases and the recombination probability increases, the luminous efficiency is easily improved.

Examples of the heteroaryl ring containing electron-accepting nitrogen include a triazine ring, a pyridine ring, a pyrazine ring, a pyrimidine ring, a quinoline ring, a quinoxaline ring, a quinazoline ring, a naphthyridine ring, a pyrimidopyrimidine ring, a benzoquinoline ring, a phenanthroline ring, an imidazole ring, an oxazole ring, an oxadiazole ring, a triazole ring, a triazole ring, a thiadiazole ring, a benzoxazole ring, a benzothiazole ring, a benzimidazole ring, and a phenanthroimidazole ring.

Preferable examples of a compound having the above-mentioned heteroaryl ring structure include pyridine derivatives, triazine derivatives, quinazoline derivatives, pyrimidine derivatives, benzimidazole derivatives, benzoxazole derivatives, benzthiazole derivatives, oxadiazole derivatives, thiadiazole derivatives, triazole derivatives, pyrazine derivatives, phenanthroline derivatives, quinoxaline derivatives, quinoline derivatives, benzoquinoline derivatives, oligopyridine derivatives such as bipyridine and terpyridine, quinoxaline derivatives, and naphthyridine derivatives. Among them, the following compounds are preferably used from the viewpoint of electron transport capability: imidazole derivatives such as tris(N-phenylbenzimidazol-2-yl) benzene, oxadiazole derivatives such as 1,3-bis[(4-tert-butylphenyl)1,3,4-oxadiazolyl]phenylene, triazole derivatives such as N-naphthyl-2,5-diphenyl-1,3,4-triazole, phenanthroline derivatives such as bathocuproine and 1,3-bis(1,10-phenanthroline-9-yl)benzene, benzoquinoline derivatives such as 2,2'-bis(benzo[h]quinolin-2-yl)-9,9'-spirobifluorene, bipyridine derivatives such as 2,5-bis(6'-(2',2"-bipyridyl))-1,1-dimethyl-3,4-diphenylsilole, terpyridine derivatives such as 1,3-bis(4'-(2,2':6'2"-terpyridinyl))benzene, and naphthyridine derivatives such as bis(1-naphthyl)-4-(1,8-naphthyridin-2-yl)phenylphosphine oxide.

In addition, it is more preferable that these derivatives have a fused polycyclic aromatic skeleton because the derivatives have an increased glass transition temperature and high electron mobility, and the effect of lowering the voltage of the light-emitting element is greater. Furthermore, in consideration of ease of improvement of the durable life of the element, ease of synthesis, and availability of raw materials, the fused polycyclic aromatic skeleton is more preferably a fluoranthene skeleton, an anthracene skeleton, a pyrene skeleton, or a phenanthroline skeleton, and is particularly preferably a fluoranthene skeleton or a phenanthroline skeleton.

It is more preferable that the compound having a fluoranthene skeleton be a compound having a fluoranthene skeleton and an amino group in order to increase the deep LUMO energy of the fluoranthene skeleton.

It is more preferable that the compound having a phenanthroline skeleton have a plurality of phenanthroline skeletons in the molecule in order to disperse the electric charge and accelerate the electron transfer.

Since the compound having a heteroaryl ring structure containing electron-accepting nitrogen has a deep HOMO level, the compound is also preferably used in a hole blocking layer. In the light-emitting element according to the present invention, it is particularly preferable that a hole blocking layer is present between the light-emitting layer and the negative electrode, and that the hole blocking layer contain a triazine derivative, a quinazoline derivative, or a pyrimidine derivative. In the present invention, the triazine derivative, the quinazoline derivative, and the pyrimidine derivative represent a compound having a triazine skeleton, a quinazoline skeleton, or a pyrimidine skeleton, respectively.

Although a preferable electron transport material is not particularly limited, specific examples include the following.

[Chemical Formula 33]

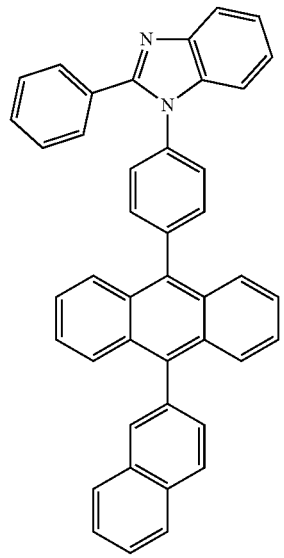

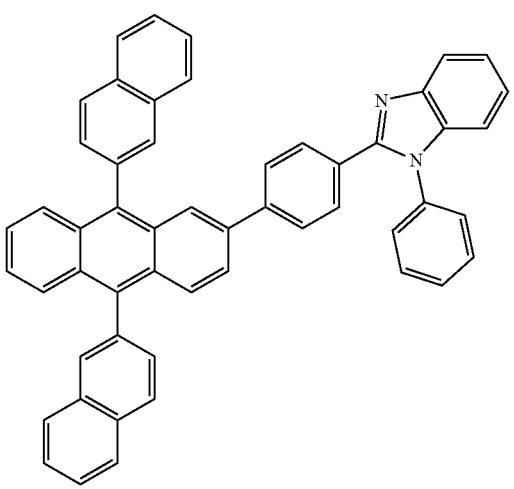

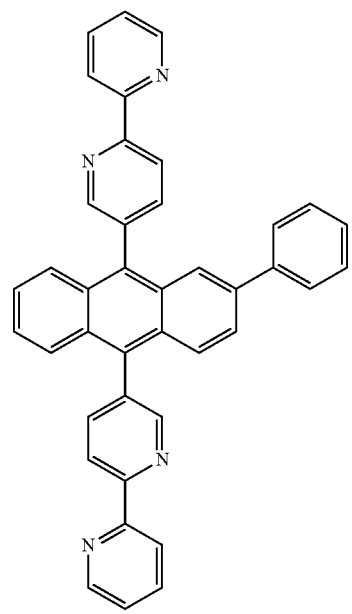

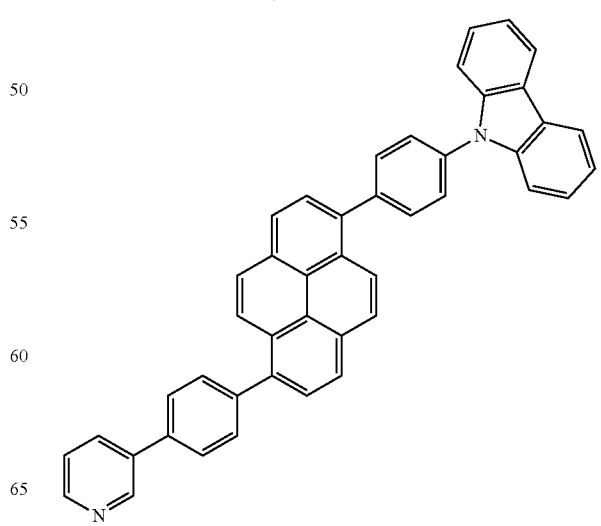

103
-continued
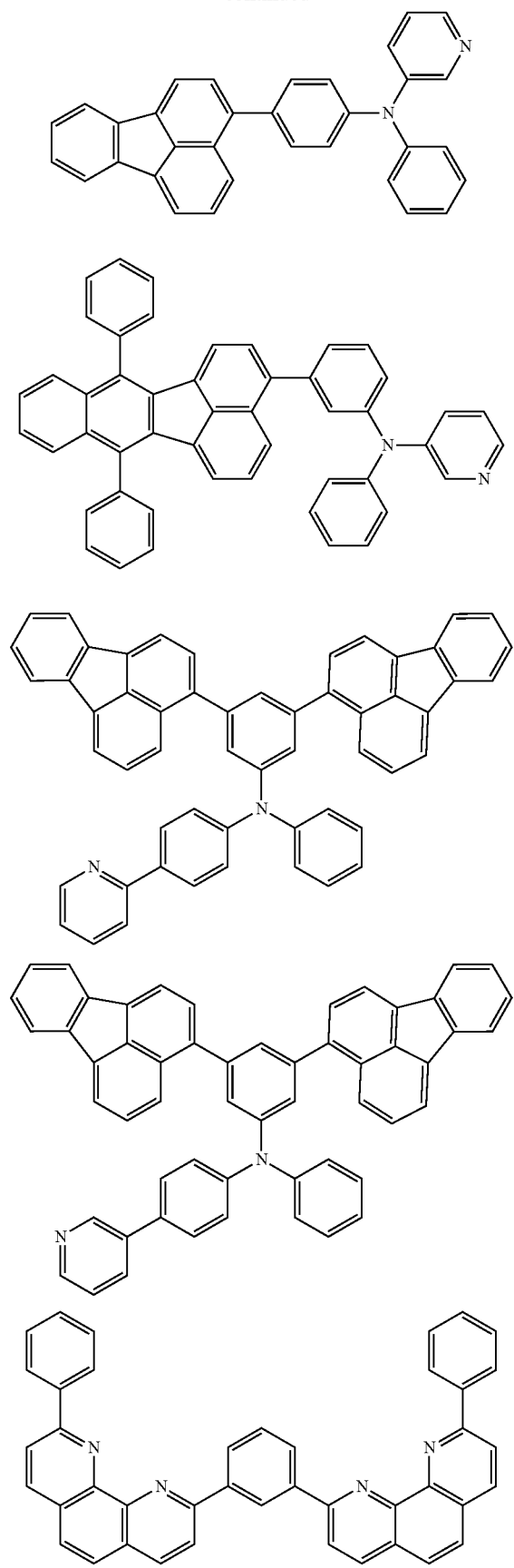
104
-continued
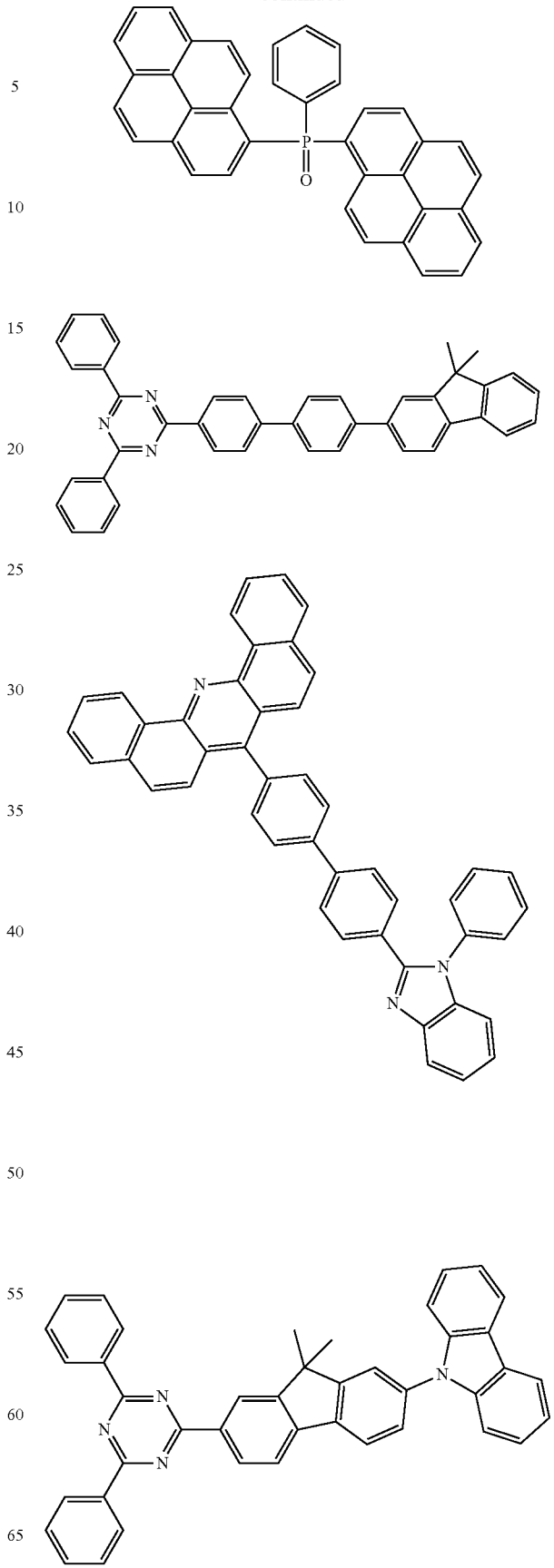

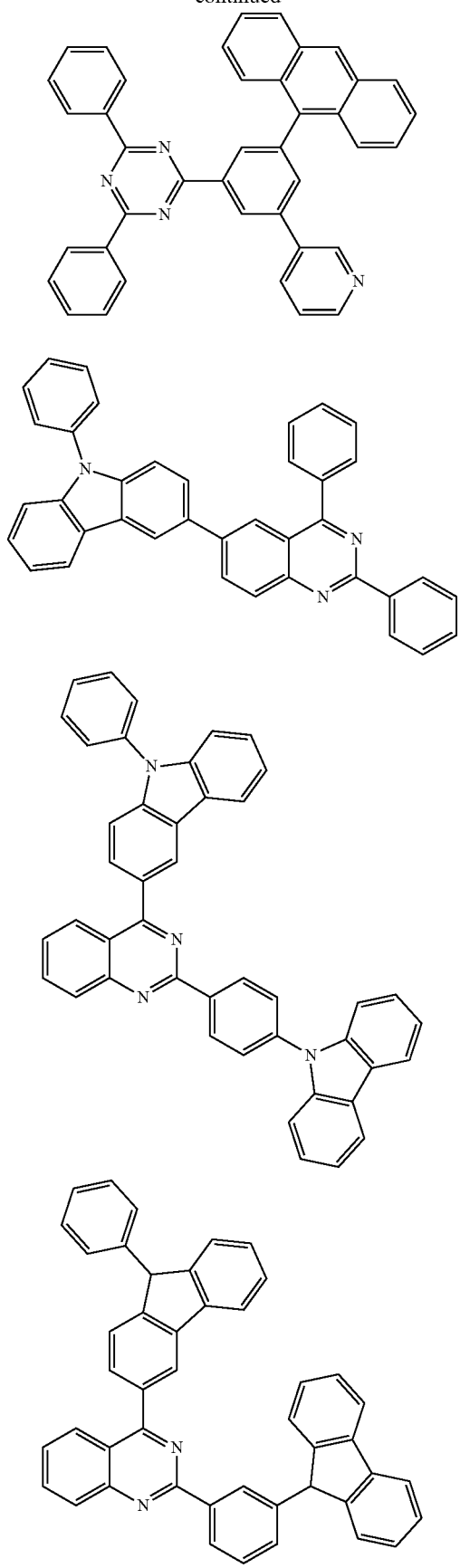

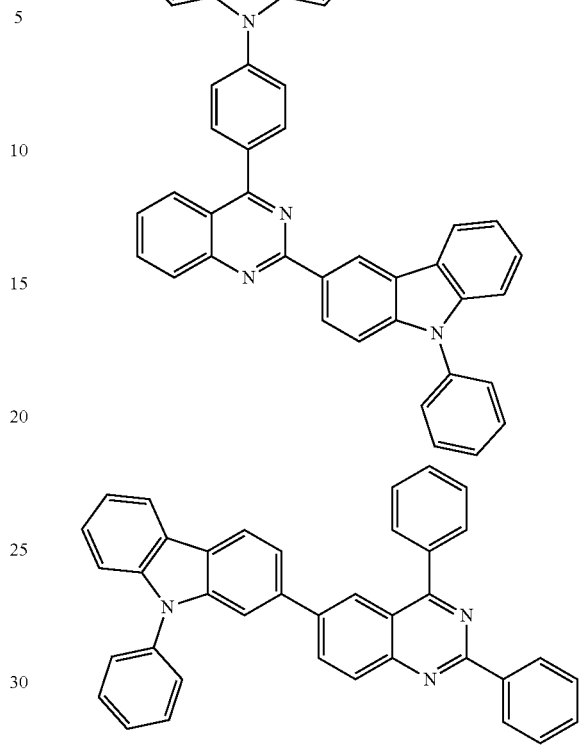

The above-mentioned electron transport materials may be used alone, or a mixture of two or more of the above-mentioned electron transport materials as well as a mixture of the above-mentioned electron transport materials and one or more other electron transport materials may be used. Moreover, the electron transport material may contain a donor compound. Herein, the donor compound is a compound that facilitates electron injection from the negative electrode or the electron injection layer into the electron transport layer by improving the electron injection barrier to further improve the electric conductivity of the electron transport layer.

Preferable examples of the donor compound include alkali metals, inorganic salts containing an alkali metal, complexes of an alkali metal and an organic substance, alkaline earth metals, inorganic salts containing an alkaline earth metal, and complexes of an alkaline earth metal and an organic substance. Preferable types of alkali metals and alkaline earth metals include alkali metals such as lithium, sodium, potassium, rubidium, and cesium, and alkaline earth metals such as magnesium, calcium, cerium, and barium, which have a low work function and a great effect of improving the electron transport capability.

In addition, due to ease of deposition in a vacuum and excellence in handleability, an inorganic salt or a complex of a metal with an organic substance is preferable rather than a single metal. Furthermore, in view of ease of handling in the atmosphere and ease of control of the addition concentration, a complex of a metal with an organic substance is more preferable. Examples of the inorganic salt include oxides such as LiO and $Li_2O$, nitrides, fluorides such as LiF, NaF, and KF, and carbonates such as $Li_2CO_3$, $Na_2CO_3$, $K_2CO_3$, $Rb_2CO_3$, and $Cs_2CO_3$. Further, preferable examples of the alkali metal and alkaline earth metal include lithium and cesium from the viewpoint that a great low voltage driving effect is achieved. In addition, in the complex of a metal with an organic substance, preferable examples of the organic substance include quinolinol, benzoquinolinol, pyridylphenol, flavonol, hydroxyimidazopyridine, hydroxybenzazole, and hydroxytriazole. Among them, a complex of an alkali metal and an organic substance is preferable from the viewpoint that the effect of lowering the voltage of the light-emitting element is greater, a complex of lithium and an organic substance is more preferable from the viewpoint of ease of synthesis and thermal stability, and lithium quinolinol (Liq), which can be obtained at relatively low cost, is particularly preferable.

The ionization potential of the electron transport layer is not particularly limited, but is preferably 5.6 eV or more and 8.0 eV or less, more preferably 5.6 eV or more and 7.0 eV or less.

The method for forming each of the above-mentioned layers that constitute the light-emitting element may be resistance heating deposition, electron beam deposition, sputtering, a molecular lamination method, or a coating method, and is not particularly limited. Usually, resistance heating deposition or electron beam deposition is preferable from the viewpoint of element characteristics.

The thickness of the organic layer is not limited because it depends on the resistance value of the luminescent material, but is preferably 1 to 1000 nm. The film thicknesses of the light-emitting layer, the electron transport layer, and the hole transport layer are each preferably 1 nm or more and 200 nm or less, more preferably 5 nm or more and 100 nm or less.

The display device according to the present invention includes the light-emitting element according to the present invention. The light-emitting element according to the present invention has a function of converting electric energy into light. Herein, the electric energy mainly used is a direct current, but a pulse current or an alternating current can also be used. The current value and voltage value are not particularly limited, but should be selected so that the maximum luminance can be obtained with as low energy as possible in consideration of the power consumption and life of the element.

The light-emitting element according to the present invention is suitably used in a display device such as a display that performs matrix system and/or segment system display, for example.

In the matrix system, pixels for display are two-dimensionally arranged in a lattice shape, a mosaic shape or the like, and a character or an image is displayed by a set of pixels. The shape and size of the pixels are determined according to the application. For example, square pixels with a side of 300 μm or less are usually used for displaying images and characters on personal computers, monitors, and television sets. Alternatively, for large displays such as display panels, pixels with a side on the order of mm are used. In monochrome display, pixels of the same color are arranged. Meanwhile, in color display, red, green, and blue pixels are displayed side by side. In this case, there are typically delta display and stripe display. The matrix driving method may be either a line sequential driving method or an active matrix driving method. Although the line sequential driving has a simple structure, the active matrix driving may be better in consideration of the operation characteristics. Therefore, it is necessary to select one of the two methods depending on the application.

The segment system in the present invention is a system in which a pattern is formed so as to display predetermined information, and a fixed region is caused to emit light based on the arrangement of the pattern. Examples of the segment system include the time and temperature display in a digital clock or a thermometer, the operation state display of an audio device or an electromagnetic cooker, and the panel display of an automobile. The matrix display and the segment display may coexist in one panel.

The light-emitting element according to the present invention is also preferably used as a backlight for various devices. The backlight is used mainly for the purpose of improving the visibility of a display device that does not emit light, such as a display, and is used in liquid crystal displays, clocks, audio devices, automobile panels, display boards, signs, and the like. In particular, the light-emitting element according to the present invention is preferably used in a backlight for liquid crystal displays, especially for personal computers for which thickness reduction is being considered, and can provide a backlight that is thinner and lighter than conventional backlights.

The lighting device according to the present invention includes the light-emitting element according to the present invention. The light-emitting element according to the present invention is also preferably used in various lighting devices. The light-emitting element according to the present invention easily achieves both high luminous efficiency and high color purity, and is easily made thinner and lighter. Therefore, it is possible to realize a lighting device that has all of low power consumption, bright emission color, and high designability.

EXAMPLES

Hereinafter, the present invention will be described with reference to examples, but the present invention is not limited by these examples.

Synthesis Example 1

Synthesis of compound HT-2

[Chemical Formula 34]

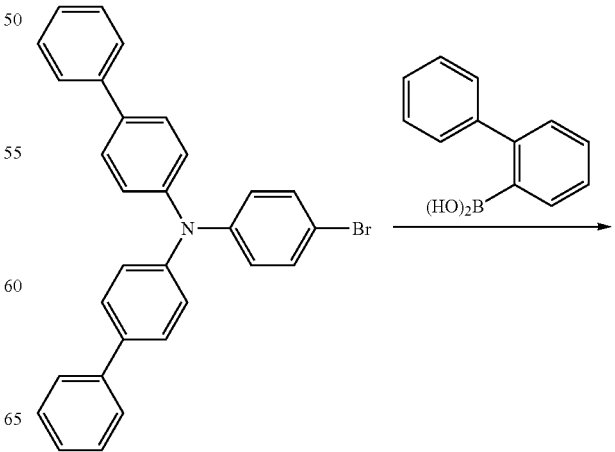

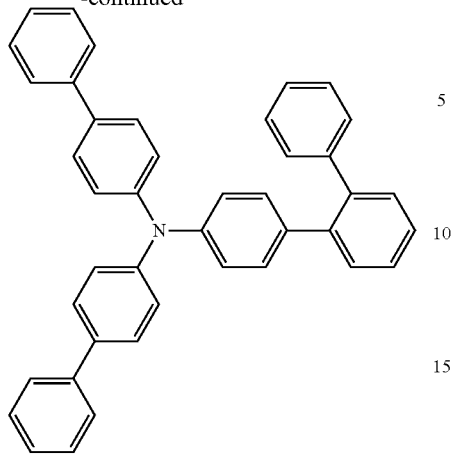

HT-2

A mixed solution of 3.34 g of N,N-bis(4-biphenylyl)-N-(4-bromophenyl)amine, 1.53 g of 2-biphenylboronic acid, 211 mg of dichlorobis(triphenylphosphine palladium)dichloride, 8 ml of a 1.5 M aqueous sodium carbonate solution, and 70 ml of dimethoxyethane was stirred with heating under reflux for 3 hours in a nitrogen stream. After the mixed solution was cooled to room temperature, water was added to the mixed solution, and the resulting mixture was filtered. The resulting residue was washed with methanol and vacuum-dried. The obtained solid was purified by silica gel column chromatography and subjected to evaporation to remove the solvent, and the obtained solid was vacuum-dried to produce 2.95 g of the compound HT-2.

The compound HT-2 was subjected to sublimation purification at about 290° C. under a pressure of $1\times10^{-3}$ Pa using an oil diffusion pump, and then used as a light-emitting element material. The HPLC purity (area % at a measurement wavelength of 254 nm) was 99.9% before sublimation purification and 99.9% after sublimation purification.

Synthesis Example 2

Synthesis of Compound HT-3

[Chemical Formula 35]

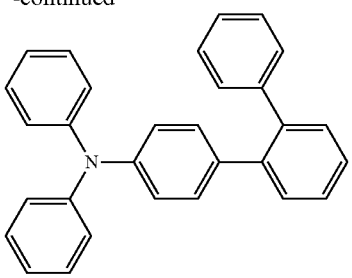

F

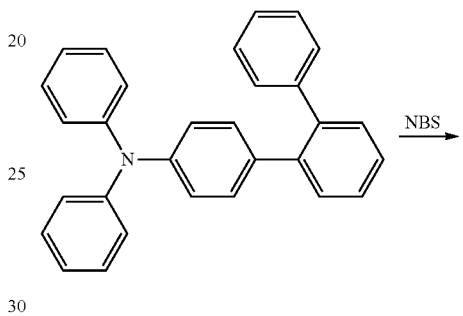

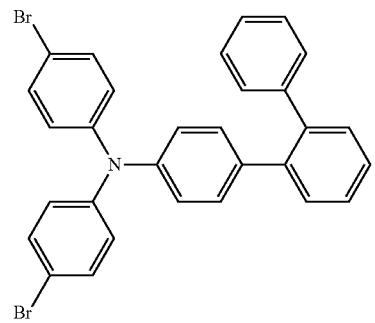

G

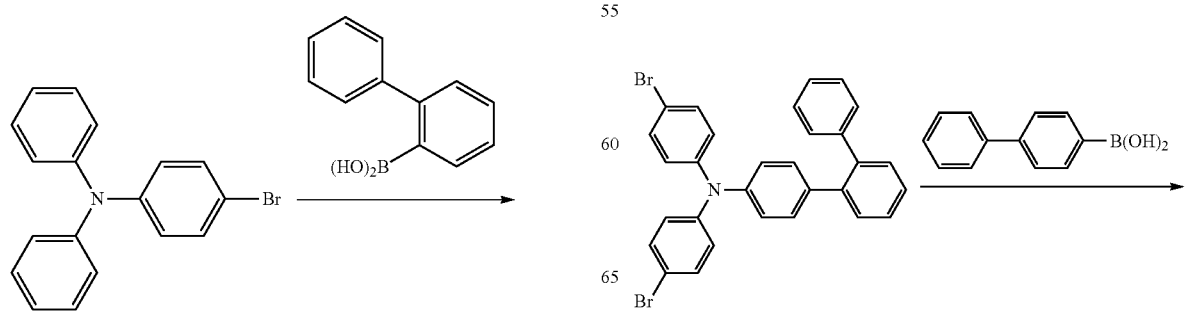

-continued

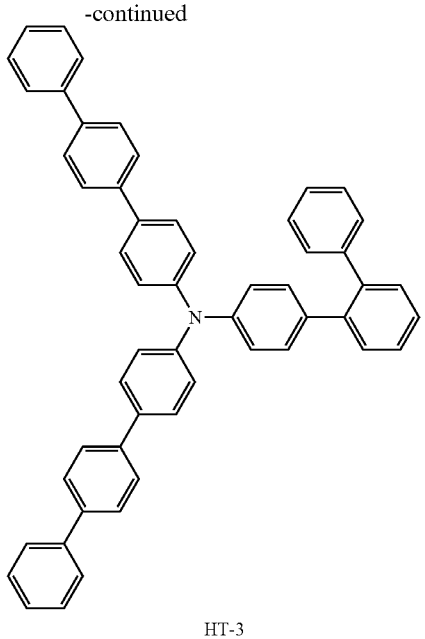

HT-3

A mixed solution of 6.21 g of 4-bromotriphenylamine, 4.19 g of 2-biphenylboronic acid, 135 mg of dichlorobis(triphenylphosphine palladium)dichloride, 20 ml of a 1.5 M aqueous sodium carbonate solution, and 190 ml of dimethoxyethane was stirred with heating under reflux for 3 hours in a nitrogen stream. After the mixed solution was cooled to room temperature, water was added to the mixed solution, and the resulting mixture was filtered. The resulting residue was washed with methanol and vacuum-dried. The obtained solid was purified by silica gel column chromatography and subjected to evaporation to remove the solvent, and the obtained solid was vacuum-dried to produce 6.58 g of an intermediate F.

Then, a mixed solution of 6.58 g of the intermediate F, 5.87 g of N-bromosuccinimide (NBS), and 166 ml of tetrahydrofuran was stirred at room temperature for 4 hours in a nitrogen stream. Water and toluene were added to the mixed solution to extract an organic layer, and the collected organic layer was dried over magnesium sulfate and then subjected to evaporation to remove the solvent. Methanol was added to the resulting concentrate, and the resulting mixture was filtered. The obtained solid was vacuum-dried to produce 8.56 g of an intermediate G.

Then, a mixed solution of 3.21 g of the intermediate G, 2.41 g of 4-biphenylboronic acid, 81 mg of dichlorobis(triphenylphosphine palladium)dichloride, 10 ml of a 1.5 M aqueous sodium carbonate solution, and 58 ml of dimethoxyethane was stirred with heating under reflux for 3 hours in a nitrogen stream. After the mixed solution was cooled to room temperature, water was added to the mixed solution, and the resulting mixture was filtered. The resulting residue was washed with methanol and vacuum-dried. The obtained solid was purified by silica gel column chromatography and subjected to evaporation to remove the solvent, and the obtained solid was vacuum-dried to produce 3.28 g of the compound HT-3.

The compound HT-3 was subjected to sublimation purification at about 340° C. under a pressure of $1\times10^{-3}$ Pa using an oil diffusion pump, and then used as a light-emitting element material. The HPLC purity (area % at a measurement wavelength of 254 nm) was 99.9% before sublimation purification and 99.9% after sublimation purification.

Example 1

A glass substrate on which 165 nm of an ITO transparent conductive film was deposited (manufactured by GEO-MATEC Co., Ltd., 11Ω/□, a sputtering product) was cut into 38×46 mm and etched. The obtained substrate was ultrasonically cleaned with "Semicoclean 56" (trade name, manufactured by Furuuchi Chemical Corporation) for 15 minutes, and then cleaned with ultrapure water. The substrate was subjected to UV-ozone treatment for 1 hour immediately before the production of the element, and placed in a vacuum deposition apparatus, and the apparatus was evacuated until the degree of vacuum in the apparatus reached $5\times10^{-4}$ Pa or less. As a hole injection layer, 10 nm of $HAT\text{-}CN_6$ was deposited by a resistance heating method. As a first hole transport layer, 40 nm of the compound HT-1 was deposited. Then, as a second hole transport layer, 10 nm of the compound HT-2 was deposited. As a light-emitting layer, a compound H-1 as a host material and a compound D-1 as a dopant material were used, and the materials were deposited to a thickness of 20 nm so that the doping concentration of the dopant material would be 3 wt %. Then, as an electron transport layer, a compound ET-1 as an electron transport material and a compound 2E-1 as a donor material were used, and the materials were deposited to a thickness of 30 nm so that the deposition rate ratio of ET-1 to 2E-1 would be ET-1:2E-1=1:1.

Then, 1 nm of the compound 2E-1 was deposited, and then 60 nm of a co-deposited film of magnesium and silver was deposited at a deposition rate ratio of magnesium to silver of magnesium:silver=10:1 (=0.5 nm/s:0.05 nm/s) to form a negative electrode, and a 5×5 mm square element was produced. The film thickness herein is a value displayed by a crystal oscillator type film thickness monitor. When the light-emitting element was DC driven at 10 mA/cm², blue light emission with an external quantum efficiency of 7.5% was obtained. For the external quantum efficiency (%), a value calculated from the front luminance (cd/m²) obtained using a spectroradiometer (CS-1000 manufactured by KONICA MINOLTA JAPAN, INC.) and an EL spectrum was used. The external quantum efficiency was calculated assuming that the obtained EL spectrum was a spectrum of a Lambertian surface (perfectly diffusing surface). When the light-emitting element was continuously driven at a direct current of 10 mA/cm², the luminance decayed to half in 2320 hours. It is to be noted that $HAT\text{-}CN_6$, HT-1, and compounds HT-2, H-1, D-1, ET-1, and 2E-1 are the compounds shown below. In the present invention, the luminous efficiency is evaluated by the external quantum efficiency or the luminous efficiency described in Example 31. The durable life is evaluated by the half-decay time of luminance.

[Chemical Formula 36]
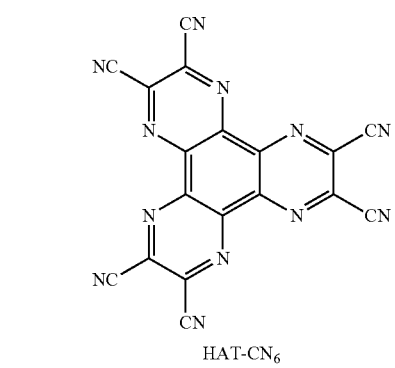
HAT-CN₆
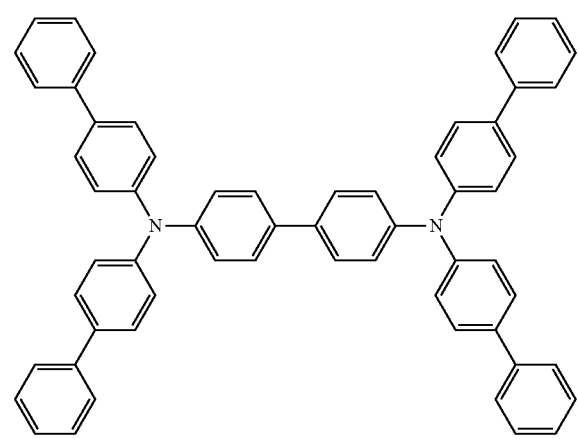
HT-1
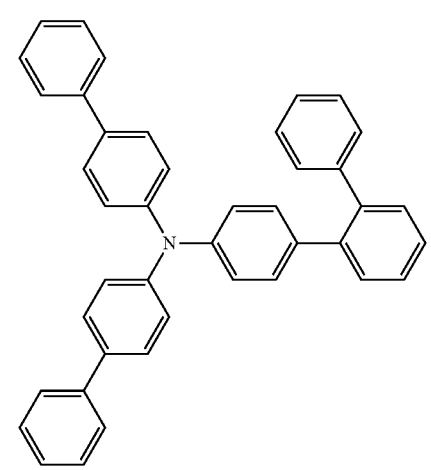
HT-2
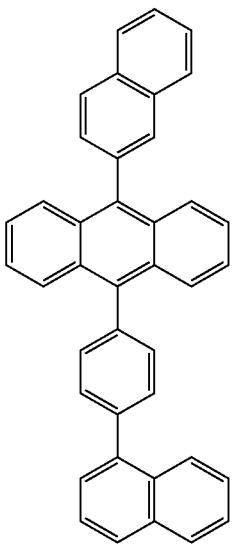
H-1
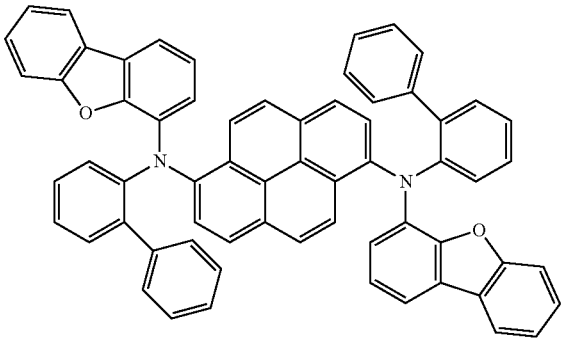
D-1
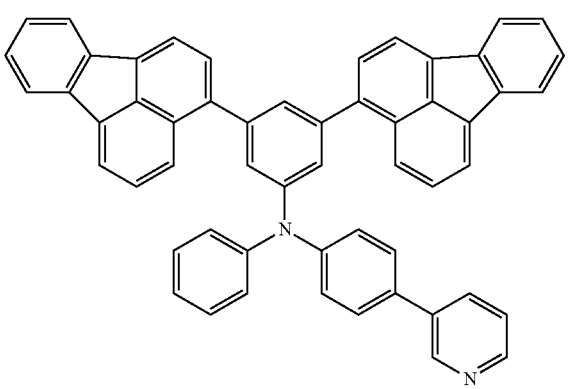
ET-1
2E-1
Examples 2 to 12 and Comparative Examples 1 to 6
A light-emitting element was produced in the same manner as in Example 1 except that the materials shown in Tables 1 and 2 were used for the second hole transport layer. The results of the examples and comparative examples are shown in Tables 1 and 2. HT-3 to HT-19 are compounds shown below.
[Chemical Formula 37]
HT-3
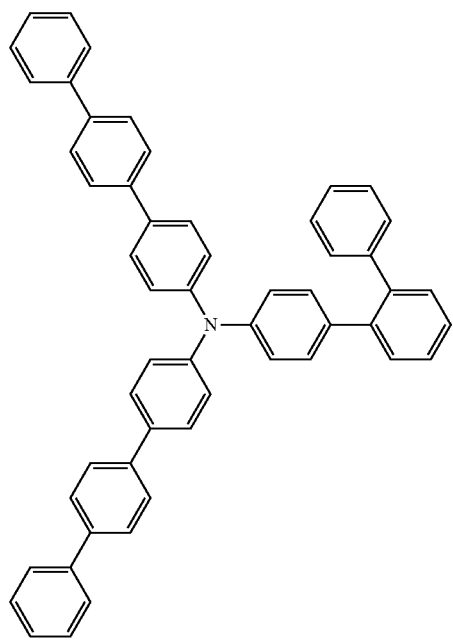
HT-5
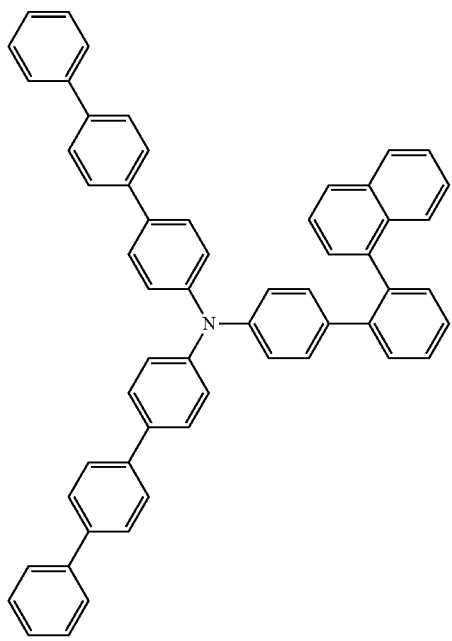
HT-4
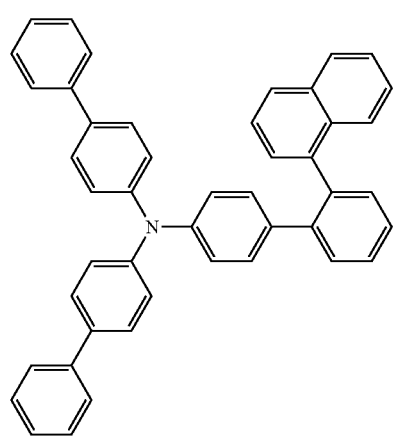
HT-6
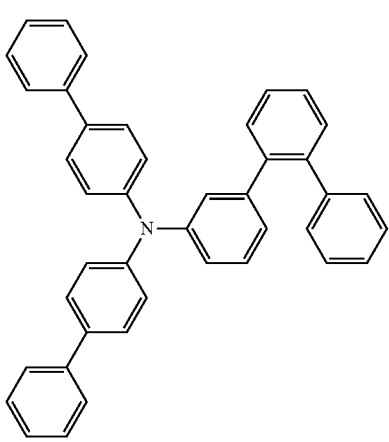

HT-7
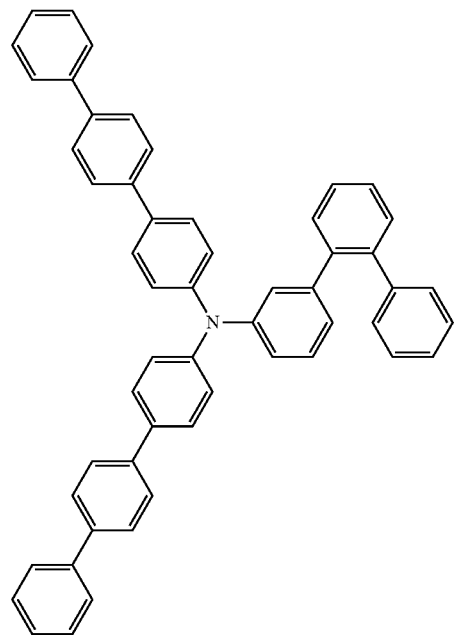
HT-9
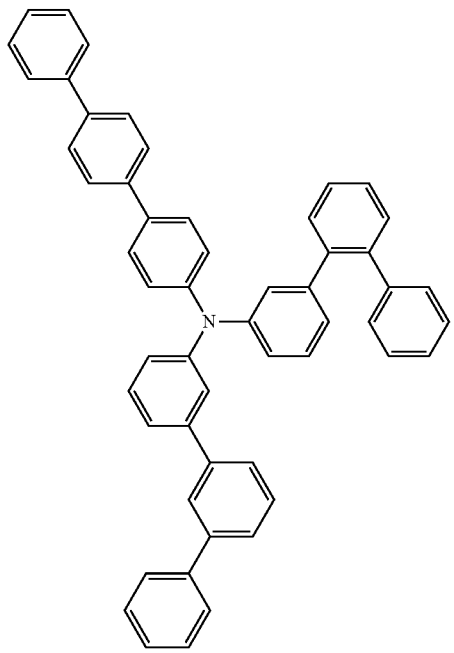
HT-8
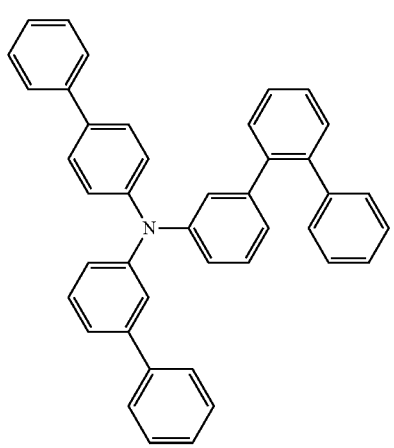
HT-10

[Chemical Formula 38]
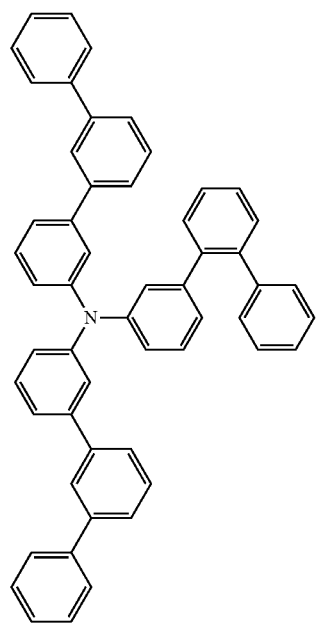
HT-11
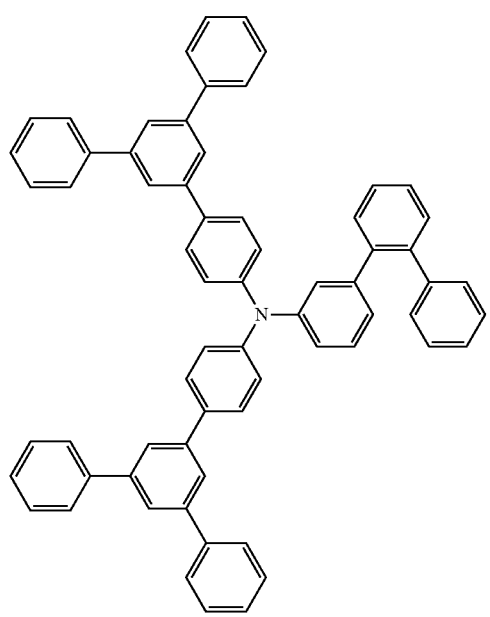
HT-12
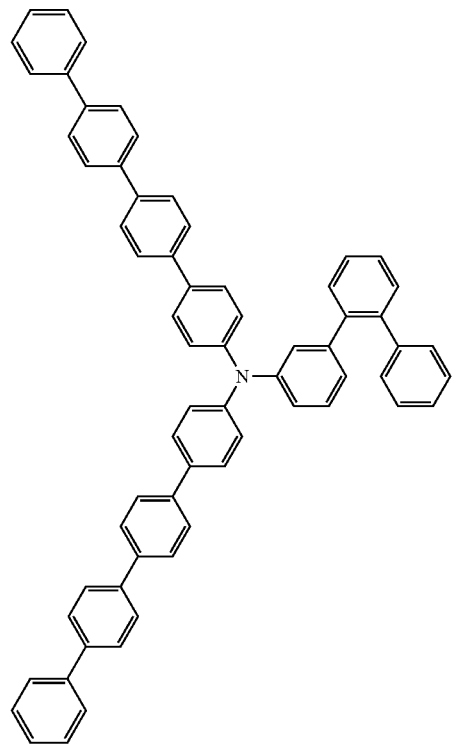
HT-13
HT-14

HT-15
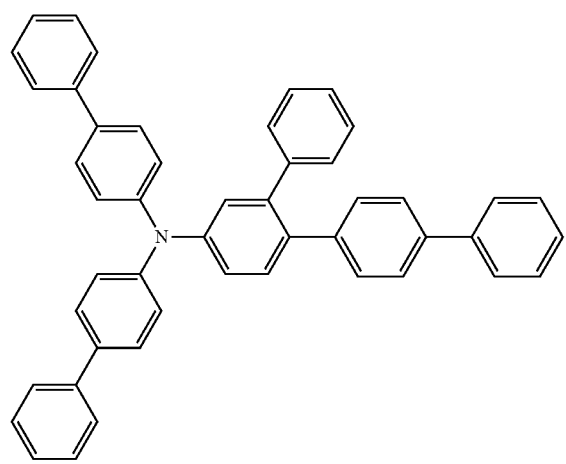
HT-18
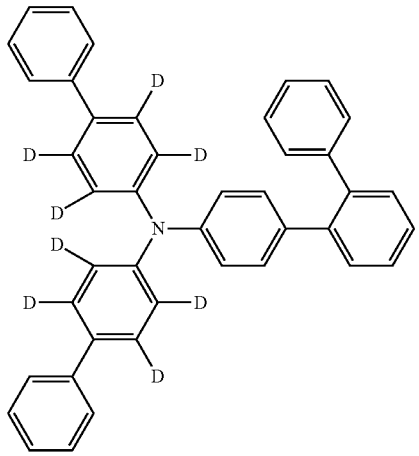
HT-19
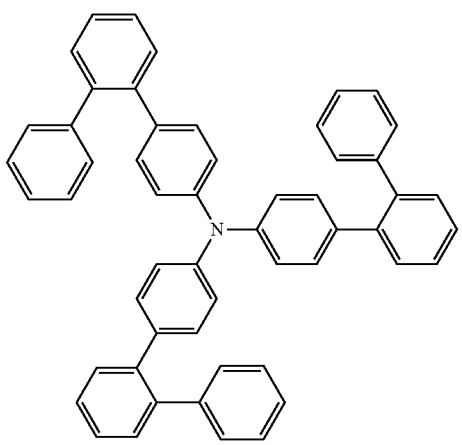
HT-16
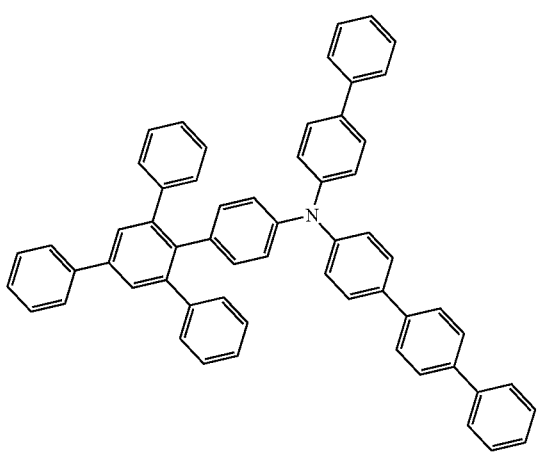
Examples 13 to 20
A light-emitting element was produced in the same manner as in Example 1 except that the materials shown in Table 2 were used for the hole transport layers and the light-emitting layer. The results of the examples are shown in Table 2. H-2 and H-3 are compounds shown below.
[Chemical Formula 39]
HT-17
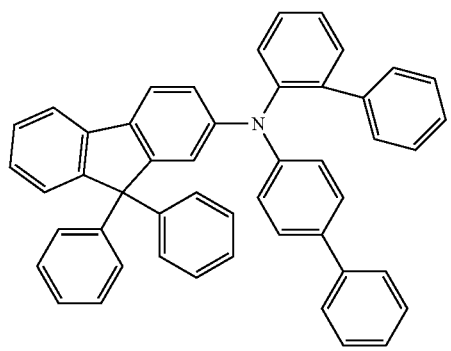
H-2
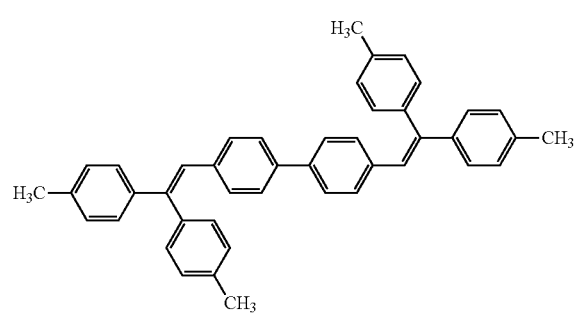

-continued

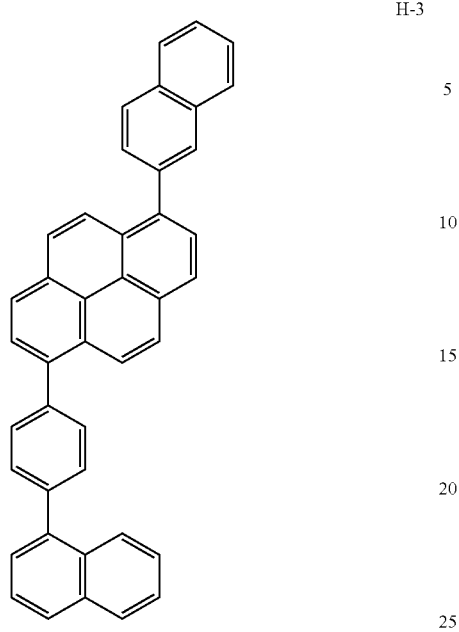

H-3

TABLE 1

|  | Hole injection layer | First hole transport layer | Second hole transport layer | Host material | Dopant material | Electron transport layer | Emission color | External quantum efficiency (%) | Half-decay time of luminance (h) |
|---|---|---|---|---|---|---|---|---|---|
| Example 1 | HAT-CN$_6$ | HT-1 | HT-2 | H-1 | D-1 | ET-1:2E-1 | Blue | 7.5 | 2320 |
| Example 2 | HAT-CN$_6$ | HT-1 | HT-3 | H-1 | D-1 | ET-1:2E-1 | Blue | 7.4 | 2330 |
| Example 3 | HAT-CN$_6$ | HT-1 | HT-4 | H-1 | D-1 | ET-1:2E-1 | Blue | 6.8 | 2300 |
| Example 4 | HAT-CN$_6$ | HT-1 | HT-5 | H-1 | D-1 | ET-1:2E-1 | Blue | 6.8 | 2300 |
| Example 5 | HAT-CN$_6$ | HT-1 | HT-6 | H-1 | D-1 | ET-1:2E-1 | Blue | 7.1 | 2030 |
| Example 6 | HAT-CN$_6$ | HT-1 | HT-7 | H-1 | D-1 | ET-1:2E-1 | Blue | 7.0 | 2030 |
| Example 7 | HAT-CN$_6$ | HT-1 | HT-8 | H-1 | D-1 | ET-1:2E-1 | Blue | 7.0 | 2010 |
| Example 8 | HAT-CN$_6$ | HT-1 | HT-9 | H-1 | D-1 | ET-1:2E-1 | Blue | 6.8 | 2020 |
| Example 9 | HAT-CN$_6$ | HT-1 | HT-10 | H-1 | D-1 | ET-1:2E-1 | Blue | 6.6 | 1810 |
| Example 10 | HAT-CN$_6$ | HT-1 | HT-11 | H-1 | D-1 | ET-1:2E-1 | Blue | 6.5 | 1810 |
| Example 11 | HAT-CN$_6$ | HT-1 | HT-12 | H-1 | D-1 | ET-1:2E-1 | Blue | 6.5 | 1850 |
| Example 12 | HAT-CN$_6$ | HT-1 | HT-13 | H-1 | D-1 | ET-1:2E-1 | Blue | 5.6 | 1600 |

TABLE 2

|  | Hole injection layer | First hole transport layer | Second hole transport layer | Host material | Dopant material | Electron transport layer | Emission color | External quantum efficiency (%) | Half-decay time of luminance (h) |
|---|---|---|---|---|---|---|---|---|---|
| Example 13 | HAT-CN$_6$ | HT-1 | HT-2 | H-2 | D-1 | ET-1:2E-1 | Blue | 7.1 | 1950 |
| Example 14 | HAT-CN$_6$ | HT-1 | HT-3 | H-2 | D-1 | ET-1:2E-1 | Blue | 7.2 | 1980 |
| Example 15 | HAT-CN$_6$ | HT-1 | HT-4 | H-2 | D-1 | ET-1:2E-1 | Blue | 6.5 | 1910 |
| Example 16 | HAT-CN$_6$ | HT-1 | HT-5 | H-2 | D-1 | ET-1:2E-1 | Blue | 6.4 | 1920 |
| Example 17 | HAT-CN$_6$ | HT-1 | HT-2 | H-3 | D-1 | ET-1:2E-1 | Blue | 7.0 | 1880 |
| Example 18 | HAT-CN$_6$ | HT-1 | HT-3 | H-3 | D-1 | ET-1:2E-1 | Blue | 7.0 | 1870 |
| Example 19 | HAT-CN$_6$ | HT-1 | HT-4 | H-3 | D-1 | ET-1:2E-1 | Blue | 6.3 | 1790 |
| Example 20 | HAT-CN$_6$ | HT-1 | HT-5 | H-3 | D-1 | ET-1:2E-1 | Blue | 6.1 | 1720 |
| Comparative Example 1 | HAT-CN$_6$ | HT-1 | HT-14 | H-1 | D-1 | ET-1:2E-1 | Blue | 4.1 | 1080 |
| Comparative Example 2 | HAT-CN$_6$ | HT-1 | HT-15 | H-1 | D-1 | ET-1:2E-1 | Blue | 3.6 | 1040 |
| Comparative Example 3 | HAT-CN$_6$ | HT-1 | HT-16 | H-1 | D-1 | ET-1:2E-1 | Blue | 4.3 | 970 |
| Comparative Example 4 | HAT-CN$_6$ | HT-1 | HT-17 | H-1 | D-1 | ET-1:2E-1 | Blue | 3.8 | 1230 |

TABLE 2-continued

| | Hole injection layer | First hole transport layer | Second hole transport layer | Host material | Dopant material | Electron transport layer | Emission color | External quantum efficiency (%) | Half-decay time of luminance (h) |
|---|---|---|---|---|---|---|---|---|---|
| Comparative Example 5 | HAT-CN$_6$ | HT-1 | HT-18 | H-1 | D-1 | ET-1:2E-1 | Blue | 4.2 | 1160 |
| Comparative Example 6 | HAT-CN$_6$ | HT-1 | HT-19 | H-1 | D-1 | ET-1:2E-1 | Blue | 4.0 | 990 |

Example 21

A glass substrate on which 165 nm of an ITO transparent conductive film was deposited (manufactured by GEO-MATEC Co., Ltd., 11Ω/□, a sputtering product) was cut into 38×46 mm and etched. The obtained substrate was ultrasonically cleaned with "Semicoclean 56" (trade name, manufactured by Furuuchi Chemical Corporation) for 15 minutes, and then cleaned with ultrapure water. The substrate was subjected to UV-ozone treatment for 1 hour immediately before the production of the element, and placed in a vacuum deposition apparatus, and the apparatus was evacuated until the degree of vacuum in the apparatus reached $5 \times 10^{-4}$ Pa or less. As a hole injection layer, 10 nm of HAT-CN$_6$ was deposited by a resistance heating method. Then, as a first hole transport layer, 40 nm of the compound HT-1 was deposited. Then, as a second hole transport layer, 10 nm of the compound HT-2 was deposited. Then, as a light-emitting layer, the compound H-1 as a host material and the compound D-1 as a dopant material were used, and the materials were deposited to a thickness of 20 nm so that the doping concentration of the dopant material would be 3 wt %. Then, as a hole blocking layer, a compound ET-2 was stacked to a thickness of 10 nm. Further, as an electron transport layer, the compound ET-1, and the compound 2E-1 as a donor material were used, and the materials were deposited to a thickness of 30 nm so that the deposition rate ratio of ET-1 to 2E-1 would be ET-1:2E-1=1:1.

Then, 1 nm of the compound 2E-1 was deposited, and then 60 nm of a co-deposited film of magnesium and silver was deposited at a deposition rate ratio of magnesium to silver of magnesium:silver=10:1 (=0.5 nm/s:0.05 nm/s) to form a negative electrode, and a 5×5 mm square element was produced. The film thickness herein is a value displayed by a crystal oscillator type film thickness monitor. When the light-emitting element was DC driven at 10 mA/cm², blue light emission with an external quantum efficiency of 8.1% was obtained. When the light-emitting element was continuously driven at a direct current of 10 mA/cm², the luminance decayed to half in 2750 hours. ET-2 is a compound shown below.

[Chemical Formula 40]

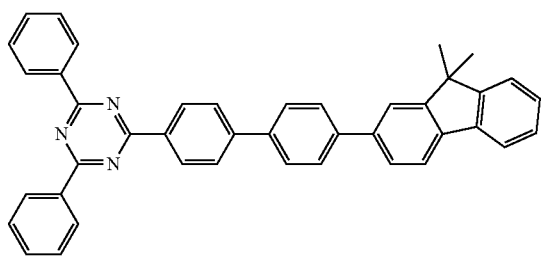

ET-2

Examples 22 to 30 and Comparative Examples 7 to 12

A light-emitting element was produced in the same manner as in Example 21 except that the materials shown in Table 3 were used for the first hole transport layer, the second hole transport layer, and the hole blocking layer. The results of the examples are shown in Table 3. ET-3 to ET-6 are compounds shown below.

[Chemical Formula 41]

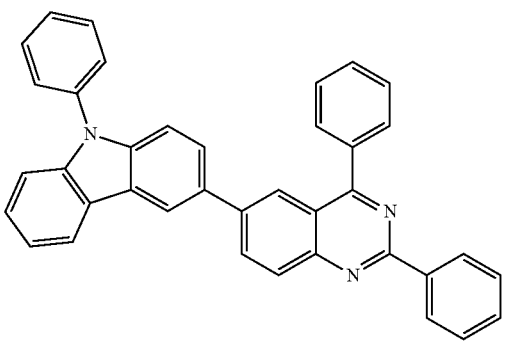

ET-3

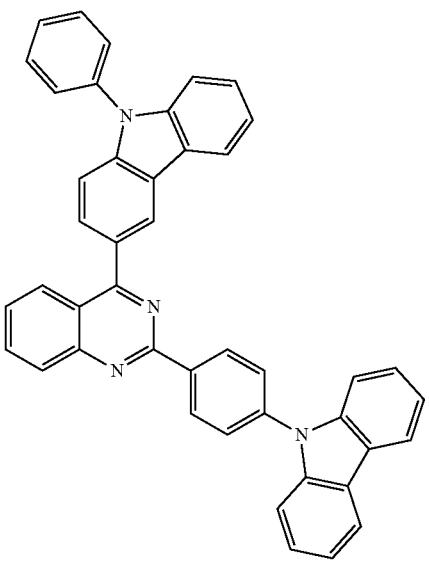

ET-4

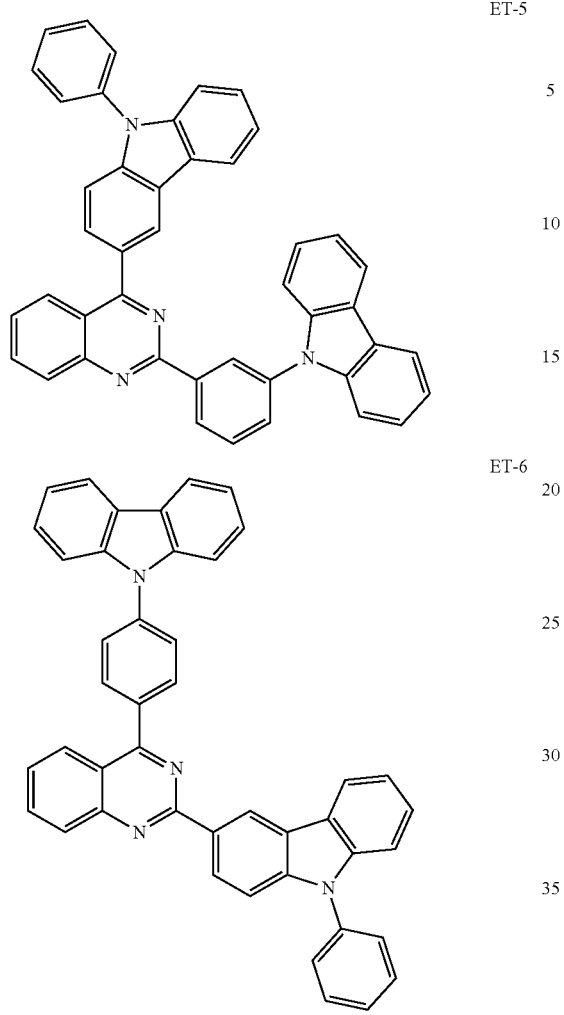

ET-5

ET-6

TABLE 3

| | Hole injection layer | First hole transport layer | Second hole transport layer | Host material | Dopant material | Hole blocking layer | Electron transport layer | Emission color | External quantum efficiency (%) | Half-decay time of luminance (h) |
|---|---|---|---|---|---|---|---|---|---|---|
| Example 21 | HAT-CN$_6$ | HT-1 | HT-2 | H-1 | D-1 | ET-2 | ET-1:2E-1 | Blue | 8.1 | 2750 |
| Example 22 | HAT-CN$_6$ | HT-1 | HT-2 | H-1 | D-1 | ET-3 | ET-1:2E-1 | Blue | 7.9 | 2740 |
| Example 23 | HAT-CN$_6$ | HT-1 | HT-2 | H-1 | D-1 | ET-4 | ET-1:2E-1 | Blue | 8.0 | 2830 |
| Example 24 | HAT-CN$_6$ | HT-1 | HT-2 | H-1 | D-1 | ET-5 | ET-1:2E-1 | Blue | 7.9 | 2810 |
| Example 25 | HAT-CN$_6$ | HT-1 | HT-2 | H-1 | D-1 | ET-6 | ET-1:2E-1 | Blue | 7.9 | 2790 |
| Example 26 | HAT-CN$_6$ | HT-1 | HT-3 | H-1 | D-1 | ET-2 | ET-1:2E-1 | Blue | 7.8 | 2950 |
| Example 27 | HAT-CN$_6$ | HT-1 | HT-3 | H-1 | D-1 | ET-3 | ET-1:2E-1 | Blue | 7.8 | 2850 |
| Example 28 | HAT-CN$_6$ | HT-1 | HT-3 | H-1 | D-1 | ET-4 | ET-1:2E-1 | Blue | 7.9 | 2880 |
| Example 29 | HAT-CN$_6$ | HT-1 | HT-3 | H-1 | D-1 | ET-5 | ET-1:2E-1 | Blue | 8.0 | 2930 |
| Example 30 | HAT-CN$_6$ | HT-1 | HT-3 | H-1 | D-1 | ET-6 | ET-1:2E-1 | Blue | 7.8 | 2850 |
| Comparative Example 7 | HAT-CN$_6$ | HT-1 | HT-14 | H-1 | D-1 | ET-2 | ET-1:2E-1 | Blue | 4.3 | 1110 |
| Comparative Example 8 | HAT-CN$_6$ | HT-1 | HT-15 | H-1 | D-1 | ET-2 | ET-1:2E-1 | Blue | 3.8 | 1080 |
| Comparative Example 9 | HAT-CN$_6$ | HT-1 | HT-16 | H-1 | D-1 | ET-2 | ET-1:2E-1 | Blue | 4.4 | 1020 |
| Comparative Example 10 | HAT-CN$_6$ | HT-1 | HT-17 | H-1 | D-1 | ET-2 | ET-1:2E-1 | Blue | 4.0 | 1260 |
| Comparative Example 11 | HAT-CN$_6$ | HT-1 | HT-18 | H-1 | D-1 | ET-2 | ET-1:2E-1 | Blue | 4.3 | 1210 |
| Comparative Example 12 | HAT-CN$_6$ | HT-1 | HT-19 | H-1 | D-1 | ET-2 | ET-1:2E-1 | Blue | 4.2 | 1050 |

Example 31

A glass substrate on which 90 nm of an ITO transparent conductive film was deposited (manufactured by GEO-MATEC Co., Ltd., 11Ω/□, a sputtering product) was cut into 38×46 mm and etched. The obtained substrate was ultrasonically cleaned with "Semicoclean 56" (trade name, manufactured by Furuuchi Chemical Corporation) for 15 minutes, and then cleaned with ultrapure water. The substrate was subjected to UV-ozone treatment for 1 hour immediately before the production of the element, and placed in a vacuum deposition apparatus, and the apparatus was evacuated until the degree of vacuum in the apparatus reached $5×10^{-4}$ Pa or less. As a hole injection layer, 10 nm of $HAT-CN_6$ was deposited by a resistance heating method. Then, as a first hole transport layer, 110 nm of the compound HT-1 was deposited. Then, as a second hole transport layer, 20 nm of the compound HT-2 was deposited. Then, as a light-emitting layer, a compound H-4 as a host material and a compound D-2 as a dopant material were used, and the materials were deposited to a thickness of 40 nm so that the doping concentration of the dopant material would be 10 wt %. Then, as an electron transport layer, the compound ET-1, and the compound 2E-1 as a donor material were used, and the materials were stacked to a thickness of 20 nm so that the deposition rate ratio of ET-1 to 2E-1 would be ET-1:2E-1=1:1.

Then, 1 nm of the compound 2E-1 was deposited, and then 60 nm of a co-deposited film of magnesium and silver was deposited at a deposition rate ratio of magnesium to silver of magnesium:silver=10:1 (=0.5 nm/s:0.05 nm/s) to form a negative electrode, and a 5×5 mm square element was produced. The film thickness herein is a value displayed by a crystal oscillator type film thickness monitor. When the light-emitting element was DC driven at 10 $mA/cm^2$, green light emission with a luminous efficiency of 45.3 m/W was obtained. The luminous efficiency (lm/W) was calculated from the front luminance ($cd/cm^2$) obtained by measurement with a spectroradiometer (CS-1000 manufactured by KONICA MINOLTA JAPAN, INC.), the power density ($W/cm^2$) input to the element, and the emission angle (sr, steradian). When the light-emitting element was continuously driven at a direct current of 10 $mA/cm^2$, the luminance decayed to half in 5430 hours. H-4 and D-2 are compounds shown below.

[Chemical Formula 42]

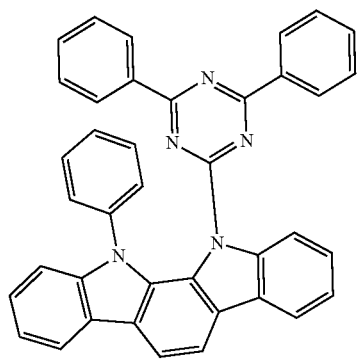
H-4

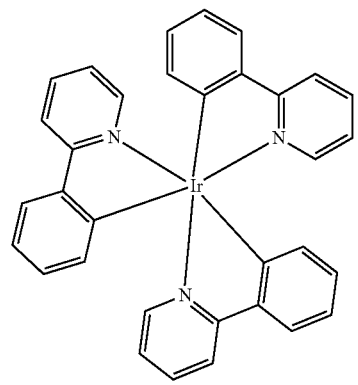
D-2

Examples 32 and 33 and Comparative Examples 13 to 18

A light-emitting element was produced in the same manner as in Example 31 except that the materials shown in Table 4 were used for the hole transport layers, and the light-emitting element was evaluated. The results are shown in Table 4.

TABLE 4

| | Hole injection layer | First hole transport layer | Second hole transport layer | Host material | Dopant material | Electron transport layer | Emission color | Luminous efficiency (lm/W) | Half-decay time of luminance (h) |
|---|---|---|---|---|---|---|---|---|---|
| Example 31 | $HAT-CN_6$ | HT-1 | HT-2 | H-4 | D-2 | ET-1:2E-1 | Green | 45.3 | 5430 |
| Example 32 | $HAT-CN_6$ | HT-1 | HT-3 | H-4 | D-2 | ET-1:2E-1 | Green | 45.1 | 5570 |
| Example 33 | $HAT-CN_6$ | HT-1 | HT-4 | H-4 | D-2 | ET-1:2E-1 | Green | 43.5 | 5280 |
| Comparative Example 13 | $HAT-CN_6$ | HT-1 | HT-14 | H-4 | D-2 | ET-1:2E-1 | Green | 28.5 | 2720 |
| Comparative Example 14 | $HAT-CN_6$ | HT-1 | HT-15 | H-4 | D-2 | ET-1:2E-1 | Green | 25.4 | 2700 |
| Comparative Example 15 | $HAT-CN_6$ | HT-1 | HT-16 | H-4 | D-2 | ET-1:2E-1 | Green | 27.5 | 2580 |
| Comparative Example 16 | $HAT-CN_6$ | HT-1 | HT-17 | H-4 | D-2 | ET-1:2E-1 | Green | 24.6 | 2630 |
| Comparative Example 17 | $HAT-CN_6$ | HT-1 | HT-18 | H-4 | D-2 | ET-1:2E-1 | Green | 23.4 | 2590 |
| Comparative Example 18 | $HAT-CN_6$ | HT-1 | HT-19 | H-4 | D-2 | ET-1:2E-1 | Green | 25.5 | 2670 |

Examples 34 to 36 and Comparative Examples 19 to 24

A light-emitting element was produced in the same manner as in Example 1 except that the materials shown in Table 5 were used for the second hole transport layer. The half-decay time of luminance when these light-emitting elements were continuously driven at 80° C. at a direct current of 10 mA/cm² is shown in Table 5. HT-20 is a compound shown below.

[Chemical Formula 43]

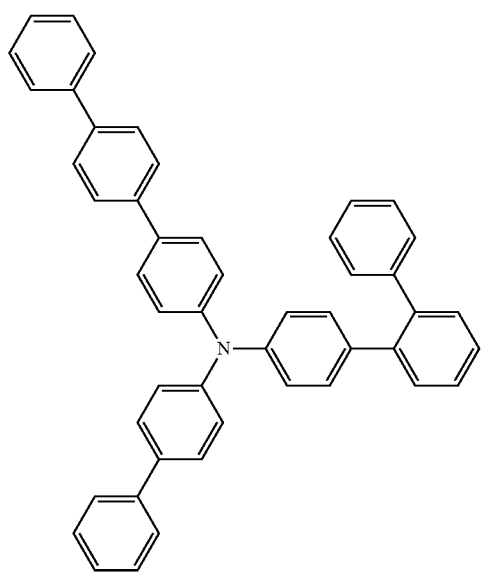

HT-20

Example 37

A glass substrate on which 165 nm of an ITO transparent conductive film was deposited (manufactured by GEO-MATEC Co., Ltd., 11Ω/□, a sputtering product) was cut into 38×46 mm and etched. The obtained substrate was ultrasonically cleaned with "Semicoclean 56" (trade name, manufactured by Furuuchi Chemical Corporation) for 15 minutes, and then cleaned with ultrapure water. The substrate was subjected to UV-ozone treatment for 1 hour immediately before the production of the element, and placed in a vacuum deposition apparatus, and the apparatus was evacuated until the degree of vacuum in the apparatus reached $5 \times 10^{-4}$ Pa or less. As a hole injection layer, 10 nm of HAT-CN₆ was deposited by a resistance heating method. Then, as a first hole transport layer, 40 nm of the compound HT-1 was deposited. Then, as a second hole transport layer, 10 nm of the compound HT-3 was deposited. Then, as a light-emitting layer, a compound H-5, a compound D-3, and a compound B-1 were deposited to a thickness of 20 nm so that the weight ratio among the compounds would be 80:1:20. Then, as a hole blocking layer, the compound ET-2 was stacked to a thickness of 10 nm. Further, as an electron transport layer, the compound ET-1, and the compound 2E-1 as a donor material were used, and the materials were deposited to a thickness of 30 nm so that the deposition rate ratio of ET-1 to 2E-1 would be ET-1:2E-1=1:1.

Then, 1 nm of the compound 2E-1 was deposited, and then 60 nm of a co-deposited film of magnesium and silver was deposited at a deposition rate ratio of magnesium to silver of magnesium:silver=10:1 (=0.5 nm/s:0.05 nm/s) to form a negative electrode, and a 5×5 mm square element was produced. The film thickness herein is a value displayed by a crystal oscillator type film thickness monitor. When the light-emitting element was DC driven at 10 mA/cm², red light emission with an external quantum efficiency of 7.5% was obtained. H-5, D-3, and B-1 are compounds shown below.

TABLE 5

| | Hole injection layer | First hole transport layer | Second hole transport layer | Host material | Dopant material | Electron transport layer | Emission color | Half-decay time of luminance (h) |
|---|---|---|---|---|---|---|---|---|
| Example 34 | HAT-CN₆ | HT-1 | HT-2 | H-1 | D-1 | ET-1:2E-1 | Blue | 1850 |
| Example 35 | HAT-CN₆ | HT-1 | HT-3 | H-1 | D-1 | ET-1:2E-1 | Blue | 2240 |
| Example 36 | HAT-CN₆ | HT-1 | HT-20 | H-1 | D-1 | ET-1:2E-1 | Blue | 2180 |
| Comparative Example 19 | HAT-CN₆ | HT-1 | HT-14 | H-1 | D-1 | ET-1:2E-1 | Blue | 450 |
| Comparative Example 20 | HAT-CN₆ | HT-1 | HT-15 | H-1 | D-1 | ET-1:2E-1 | Blue | 680 |
| Comparative Example 21 | HAT-CN₆ | HT-1 | HT-16 | H-1 | D-1 | ET-1:2E-1 | Blue | 750 |
| Comparative Example 22 | HAT-CN₆ | HT-1 | HT-17 | H-1 | D-1 | ET-1:2E-1 | Blue | 880 |
| Comparative Example 23 | HAT-CN₆ | HT-1 | HT-18 | H-1 | D-1 | ET-1:2E-1 | Blue | 730 |
| Comparative Example 24 | HAT-CN₆ | HT-1 | HT-19 | H-1 | D-1 | ET-1:2E-1 | Blue | 640 |

[Chemical Formula 44]
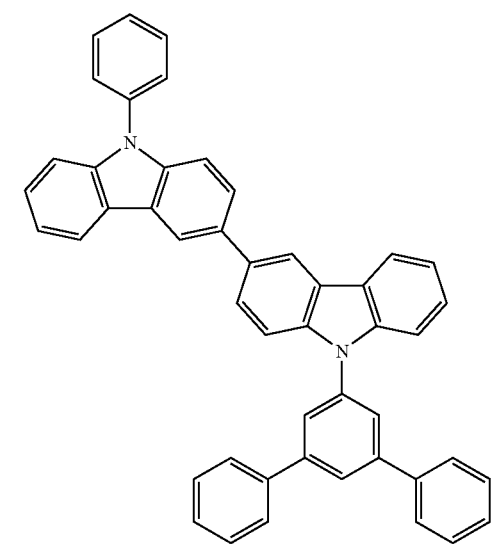
H-5
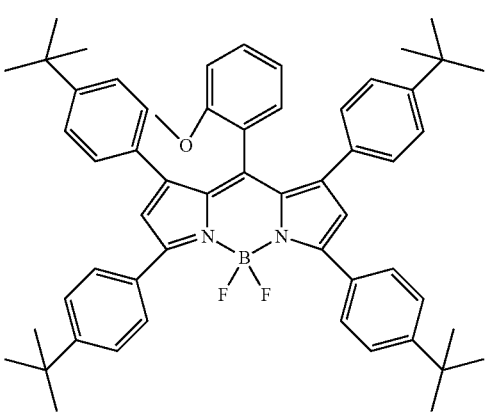
D-3
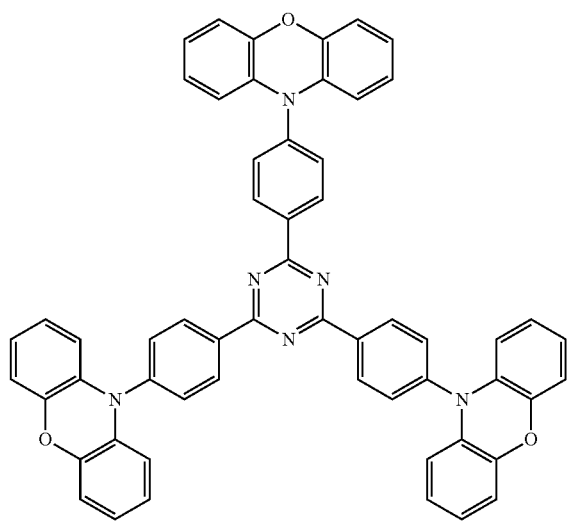
B-1
Table 6 were used as materials of the light-emitting layer, and the light-emitting element was evaluated. The results are shown in Table 6. D-4 to D-6 and B-2 are compounds shown below.
[Chemical Formula 45]
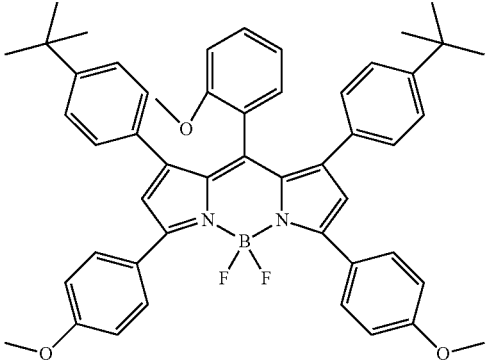
D-4
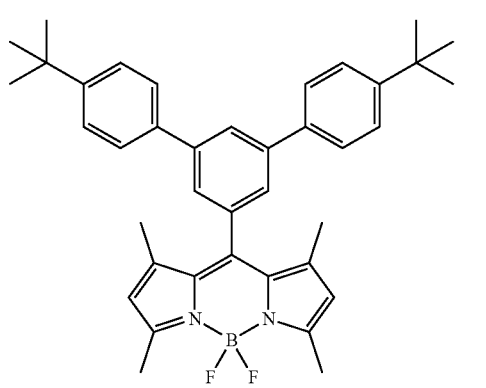
D-5
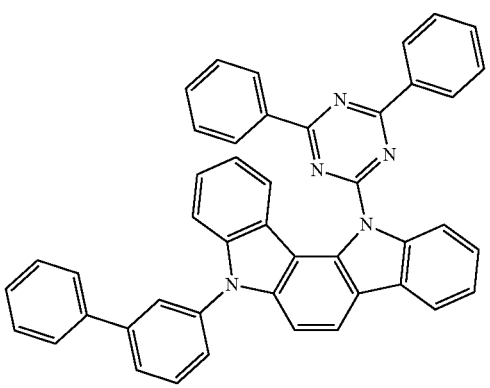
B-2
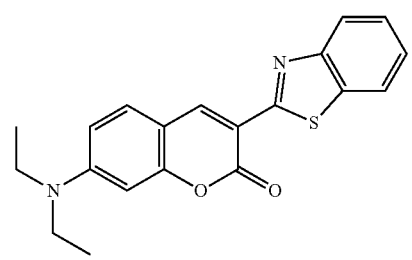
D-6
Examples 38 to 40 and Comparative Examples 25 to 30
A light-emitting element was produced in the same manner as in Example 37 except that the compounds shown in

TABLE 6

| | Hole injection layer | First hole transport layer | Second hole transport layer | Light-emitting layer | | | Electron transport layer | Emission color | External quantum efficiency (%) |
|---|---|---|---|---|---|---|---|---|---|
| | | | | Host material | Dopant material | TADF material | | | |
| Example 37 | HAT-CN$_6$ | HT-1 | HT-3 | H-5 | D-3 | B-1 | ET-1:2E-1 | Red | 7.5 |
| Example 38 | HAT-CN$_6$ | HT-1 | HT-3 | H-5 | D-4 | B-1 | ET-1:2E-1 | Red | 7.1 |
| Example 39 | HAT-CN$_6$ | HT-1 | HT-3 | H-5 | D-5 | B-2 | ET-1:2E-1 | Green | 6.6 |
| Example 40 | HAT-CN$_6$ | HT-1 | HT-3 | H-5 | D-6 | B-2 | ET-1:2E-1 | Green | 4.1 |
| Comparative Example 25 | HAT-CN$_6$ | HT-1 | HT-14 | H-5 | D-3 | B-1 | ET-1:2E-1 | Red | 2.3 |
| Comparative Example 26 | HAT-CN$_6$ | HT-1 | HT-15 | H-5 | D-3 | B-1 | ET-1:2E-1 | Red | 2.1 |
| Comparative Example 27 | HAT-CN$_6$ | HT-1 | HT-16 | H-5 | D-4 | B-1 | ET-1:2E-1 | Red | 1.5 |
| Comparative Example 28 | HAT-CN$_6$ | HT-1 | HT-17 | H-5 | D-4 | B-1 | ET-1:2E-1 | Red | 1.6 |
| Comparative Example 29 | HAT-CN$_6$ | HT-1 | HT-18 | H-5 | D-5 | B-2 | ET-1:2E-1 | Green | 1.4 |
| Comparative Example 30 | HAT-CN$_6$ | HT-1 | HT-19 | H-5 | D-5 | B-2 | ET-1:2E-1 | Green | 1.4 |

The invention claimed is:

1. A compound represented by a general formula (1) shown below:

[Chemical Formula 1]

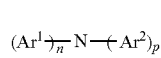
(1)

wherein Ar$^1$ is a group represented by a general formula (2) shown below, Ar$^2$ is a group represented by a general formula (3) shown below, n is an integer of 1 or 2, p is an integer of 1 or 2, where n+p=3, and when n is 2, the groups Ar$^1$ may be identical or different, when p is 2, the groups Ar$^2$ may be identical or different, and Ar$^1$ and Ar$^2$ are not an identical group;

[Chemical Formula 2]

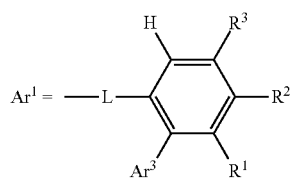
(2)

wherein H represents a hydrogen atom, Ar$^3$ represents a substituted or unsubstituted aryl group or a substituted or unsubstituted heteroaryl group, L represents a linking group, and represents an unsubstituted arylene group or a heteroarylene group, R$^1$ to R$^3$ may be identical or different, and are each a hydrogen atom, a substituted or unsubstituted alkyl group, a substituted or unsubstituted alkoxy group, a substituted or unsubstituted phenyl group, a substituted or unsubstituted biphenyl group, or a substituted or unsubstituted terphenyl group, and substituents when the groups R$^1$- to R$^3$ are substituted are each an alkyl group or an alkoxy group;

[Chemical Formula 3]

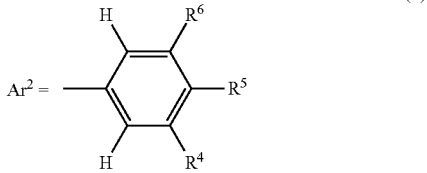
(3)

wherein H represents a hydrogen atom, R$^4$ to R$^6$ may be identical or different, and are each a hydrogen atom, a substituted or unsubstituted phenyl group, a substituted or unsubstituted biphenyl group, a substituted or unsubstituted terphenyl group, or a substituted or unsubstituted quaterphenyl group, and substituents when the groups R$^4$ to R$^6$ are substituted are each an alkyl group or an alkoxy group; and wherein, in the general formula (1), at least one of Ar$^2$ is a substituted or unsubstituted p-terphenyl group.

2. The compound according to claim 1, wherein, in the general formula (1), at least one of Ar$^2$ is a substituted or unsubstituted phenyl group, a substituted or unsubstituted biphenyl group, a substituted or unsubstituted terphenyl group, or a substituted or unsubstituted quaterphenyl group excluding a group shown below:

[Chemical Formula 4]

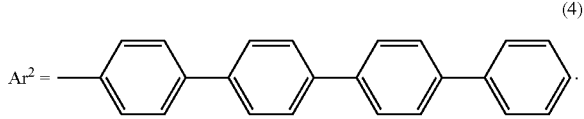
(4)

3. The compound according to claim 1, wherein, in the general formula (2), L is a 1,4-phenylene group.

4. The compound according to claim 1, wherein, in the general formula (2), Ar$^3$ is a substituted or unsubstituted phenyl group, a substituted or unsubstituted biphenyl group, or a substituted or unsubstituted terphenyl group.

5. A light-emitting element that emits light by electric energy, the light-emitting element comprising a positive electrode, a negative electrode, and an organic layer present between the positive electrode and the negative electrode, and comprising a compound represented by a general formula (1) in at least one organic layer between the positive electrode and the negative electrode, wherein, in the organic layer, at least a hole transport layer and a light-emitting layer are present, and the hole transport layer contains the compound represented by the general formula (1); and wherein a hole blocking layer is present between the light-emitting layer and the negative electrode, and the hole blocking layer contains a triazine derivative, a quinazoline derivative, or a pyrimidine derivative;

wherein the compound represented by the general formula (1) is shown below:

[Chemical Formula 1]

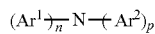
(1)

wherein $Ar^1$ is a group represented by a general formula (2) shown below, $Ar^2$ is a group represented by a general formula (3) shown below, n is an integer of 1 or 2, p is an integer of 1 or 2, where n+p=3, and when n is 2, the groups $Ar^1$ may be identical or different, when p is 2, the groups $Ar^2$ may be identical or different, and $Ar^1$ and $Ar^2$ are not an identical group;

[Chemical Formula 2]

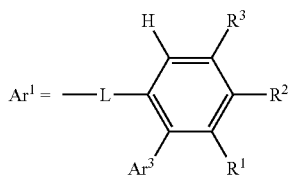
(2)

wherein H represents a hydrogen atom, $Ar^3$ represents a substituted or unsubstituted aryl group or a substituted or unsubstituted heteroaryl group, L represents a linking group, and represents an unsubstituted arylene group or a heteroarylene group $R^1$ to $R^3$ may be identical or different, and are each a hydrogen atom, a substituted or unsubstituted alkyl group, a substituted or unsubstituted alkoxy group, a substituted or unsubstituted phenyl group, a substituted or unsubstituted biphenyl group, or a substituted or unsubstituted terphenyl group, and substituents when the groups $R^1$ to $R^3$ are substituted are each an alkyl group or an alkoxy group;

[Chemical Formula 3]

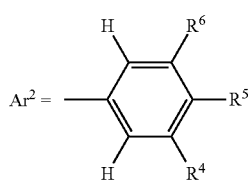
(3)

wherein H represents a hydrogen atom, $R^4$ to $R^6$ may be identical or different, and are each a hydrogen atom, a substituted or unsubstituted phenyl group, a substituted or unsubstituted biphenyl group, a substituted or unsubstituted terphenyl group, or a substituted or unsubstituted quaterphenyl group, and substituents when the groups $R^4$ to $R^6$ are substituted are each an alkyl group or an alkoxy group; and wherein, in the general formula (1), at least one of $Ar^2$ is a substituted or unsubstituted p-biphenyl group or a substituted or unsubstituted p-terphenyl group.

6. The light-emitting element according to claim 5, wherein the hole transport layer comprises a plurality of layers, and a hole transport layer containing the compound represented by the general formula (1) is in direct contact with the light-emitting layer.

7. The light-emitting element according to claim 5, wherein the light-emitting layer contains an anthracene compound.

8. The light-emitting element according to claim 5, wherein the light-emitting layer contains a triplet light-emitting material.

9. The light-emitting element according to claim 5, wherein the light-emitting layer contains a thermally activated delayed fluorescent compound.

10. A light-emitting element that emits light by electric energy, the light-emitting element comprising a positive electrode, a negative electrode, and an organic layer present between the positive electrode and the negative electrode, and comprising a compound represented by a general formula (1) in at least one organic layer between the positive electrode and the negative electrode, wherein, in the organic layer, at least a hole transport layer and a light-emitting layer are present, and the hole transport layer contains the compound represented by the general formula (1);

wherein the light-emitting layer contains a thermally activated delayed fluorescent compound;

wherein the light-emitting layer further contains a fluorescent dopant;

wherein the compound represented by the general formula (1) is shown below:

[Chemical Formula 1]

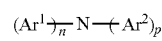
(1)

wherein $Ar^1$ is a group represented by a general formula (2) shown below, $Ar^2$ is a group represented by a general formula (3) shown below, n is an integer of 1 or 2, p is an integer of 1 or 2, where n+p=3, and when n is 2, the groups $Ar^1$ may be identical or different, when p is 2, the groups $Ar^2$ may be identical or different, and $Ar^1$ and $Ar^2$ are not an identical group;

[Chemical Formula 2]

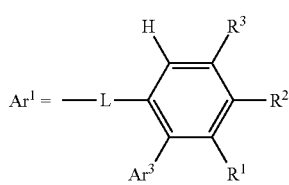
(2)

wherein H represents a hydrogen atom, $Ar^3$ represents a substituted or unsubstituted aryl group or a substituted or unsubstituted heteroaryl group, L represents a linking group, and represents an unsubstituted arylene group or a heteroarylene group, $R^1$ to $R^3$ may be identical or different, and are each a hydrogen atom, a substituted or unsubstituted alkyl group, a substituted or unsubstituted alkoxy group, a substituted or unsubstituted phenyl group, a substituted or unsubstituted biphenyl group, or a substituted or unsubstituted terphenyl group, and substituents when the groups $R^1$ to $R^3$ are substituted are each an alkyl group or an alkoxy group; and

[Chemical Formula 3]

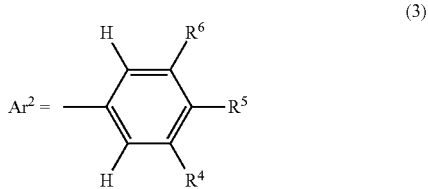

(3)

wherein H represents a hydrogen atom, $R^4$ to $R^6$ may be identical or different, and are each a hydrogen atom, a substituted or unsubstituted phenyl group, a substituted or unsubstituted biphenyl group, a substituted or unsubstituted terphenyl group, or a substituted or unsubstituted quaterphenyl group, and substituents when the groups $R^4$ to $R^6$ are substituted are each an alkyl group or an alkoxy group.

11. The light-emitting element according to claim 10, wherein the fluorescent dopant contained in the light-emitting layer is represented by a general formula (5) shown below:

[Chemical Formula 5]

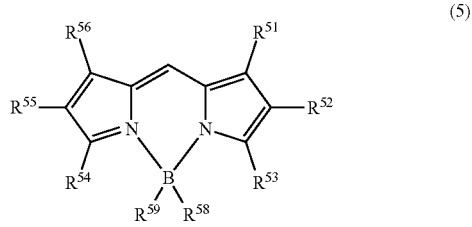

(5)

wherein X represents C—$R^{57}$ or N, $R^{51}$ to $R^{59}$ may be identical or different, and are each selected from a hydrogen atom, an alkyl group, a cycloalkyl group, a heterocyclic group, an alkenyl group, a cycloalkenyl group, an alkynyl group, a hydroxyl group, a thiol group, an alkoxy group, an alkylthio group, an aryl ether group, an aryl thioether group, an aryl group, a heteroaryl group, a halogen, a cyano group, an aldehyde group, a carbonyl group, a carboxyl group, an ester group, a carbamoyl group, an amino group, a nitro group, a silyl group, a siloxanyl group, a boryl group, —P(=O)$R^{60}$ $R^{61}$, and a fused ring and an aliphatic ring formed between the group and an adjacent substituent, and $R^{60}$ and $R^{61}$ are each an aryl group or a heteroaryl group.

12. A display device comprising the light-emitting element according to claim 5.

13. A lighting device comprising the light-emitting element according to claim 5.

14. The light-emitting element according to claim 7, wherein, in the general formula (1), at least one of $Ar^2$ is a substituted or unsubstituted phenyl group, a substituted or unsubstituted biphenyl group, a substituted or unsubstituted terphenyl group, or a substituted or unsubstituted quaterphenyl group excluding a group shown below:

[Chemical Formula 4]

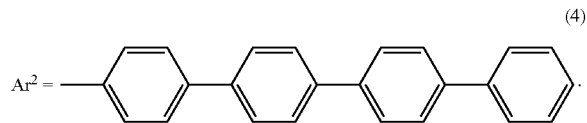

(4)

15. The light-emitting element according to claim 5, wherein, in the general formula (1), at least one of $Ar^2$ is a substituted or unsubstituted p-terphenyl group.

16. The light-emitting element according to claim 5, wherein, in the general formula (2), L is a 1,4-phenylene group.

17. The light-emitting element according to claim 5, wherein, in the general formula (2), $Ar^3$ is a substituted or unsubstituted phenyl group, a substituted or unsubstituted biphenyl group, or a substituted or unsubstituted terphenyl group.

18. A display device comprising the light-emitting element according to claim 10.

19. A lighting device comprising the light-emitting element according to claim 10.

* * * * *

UNITED STATES PATENT AND TRADEMARK OFFICE
CERTIFICATE OF CORRECTION

PATENT NO. : 11,605,780 B2  
APPLICATION NO. : 16/636994  
DATED : March 14, 2023  
INVENTOR(S) : Takashi Tokuda Page 1 of 1

It is certified that error appears in the above-identified patent and that said Letters Patent is hereby corrected as shown below:

In the Claims

In Claim 1, Column 135, Lines 65-66 "$R^1$ – to $R^3$ are substituted" should read -- $R^1$ to $R^3$ are substituted --.

In Claim 11, Column 139, [Chemical Formula 5] " 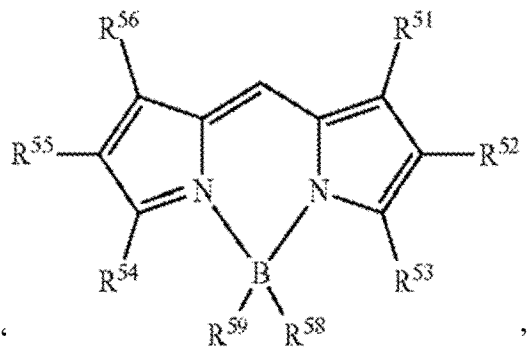 " should read -- 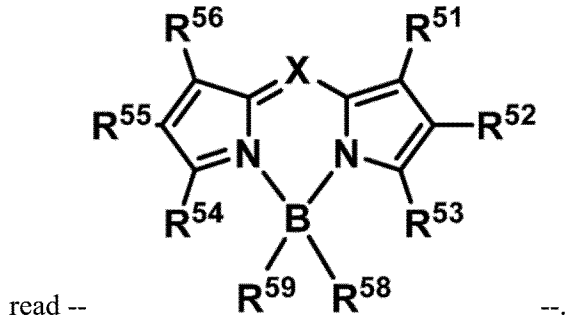 --.

Signed and Sealed this  
Thirtieth Day of May, 2023

Katherine Kelly Vidal  
*Director of the United States Patent and Trademark Office*